(12) United States Patent
Loulmet et al.

(10) Patent No.: US 9,125,632 B2
(45) Date of Patent: Sep. 8, 2015

(54) SYSTEMS AND METHODS FOR CARDIAC REMODELING

(75) Inventors: Didier Loulmet, New York, NY (US); Niel F. Starksen, Los Altos Hills, CA (US); Mariel Fabro, San Jose, CA (US); Eugene Serina, Union City, CA (US)

(73) Assignee: Guided Delivery Systems, Inc., Santa Clara, CA (US)

( * ) Notice: Subject to any disclaimer, the term of this patent is extended or adjusted under 35 U.S.C. 154(b) by 1638 days.

(21) Appl. No.: 12/253,792

(22) Filed: Oct. 17, 2008

(65) Prior Publication Data

US 2009/0234318 A1    Sep. 17, 2009

Related U.S. Application Data

(60) Provisional application No. 60/981,423, filed on Oct. 19, 2007.

(51) Int. Cl.
  *A61F 2/24* (2006.01)
  *A61B 17/00* (2006.01)
  *A61B 17/04* (2006.01)
  *A61B 17/064* (2006.01)

(52) U.S. Cl.
  CPC ....... *A61B 17/00234* (2013.01); *A61B 17/0401* (2013.01); *A61B 17/064* (2013.01); *A61F 2/2487* (2013.01); *A61B 17/0644* (2013.01); *A61B 2017/00243* (2013.01); *A61B 2017/00783* (2013.01); *A61B 2017/0414* (2013.01); *A61B 2017/0496* (2013.01); *A61F 2/2445* (2013.01); *A61F 2/2481* (2013.01)

(58) Field of Classification Search
  CPC ........................................ A61F 2/24
  USPC ............................................. 623/2.36
  See application file for complete search history.

(56) References Cited

U.S. PATENT DOCUMENTS

| | | |
|---|---|---|
| 3,656,185 A | 4/1972 | Carpentier |
| 3,727,614 A | 4/1973 | Kniazuk |
| 4,042,979 A | 8/1977 | Angell |
| 4,290,151 A | 9/1981 | Massana |
| 4,489,446 A | 12/1984 | Reed |

(Continued)

FOREIGN PATENT DOCUMENTS

| | | |
|---|---|---|
| WO | WO-95/15715 A1 | 6/1995 |
| WO | WO-96/39081 A1 | 12/1996 |

(Continued)

OTHER PUBLICATIONS

Final Office Action mailed on Feb. 6, 2007, for U.S. Appl. No. 10/656,797, filed Sep. 4, 2003, 8 pages.

(Continued)

Primary Examiner — Thomas J Sweet
Assistant Examiner — Matthew Schall
(74) Attorney, Agent, or Firm — Morrison & Foerster LLP

(57) ABSTRACT

Described herein are devices and methods for improving the hemodynamic function of a patient. In particular, a first device adapted to reshape an atrio-ventricular valve is used in combination with a second device configured to further alter the blood flow through the valve. The first device is typically an implant positioned in the subvalvular space of a ventricle. The second device may be an annuloplasty implant, a non-annulus valve apparatus implant, a ventriculoplasty implant, or a cardiac rhythm management device.

16 Claims, 47 Drawing Sheets

(56) References Cited

U.S. PATENT DOCUMENTS

| | | |
|---|---|---|
| 5,064,431 A | 11/1991 | Gilbertson et al. |
| 5,324,298 A | 6/1994 | Phillips et al. |
| 5,527,232 A | 6/1996 | Seidel et al. |
| 5,527,323 A | 6/1996 | Jervis et al. |
| 5,571,215 A | 11/1996 | Sterman et al. |
| 5,718,725 A | 2/1998 | Sterman et al. |
| 5,735,290 A | 4/1998 | Sterman et al. |
| 5,817,107 A | 10/1998 | Schaller |
| 5,961,440 A | 10/1999 | Schweich, Jr. et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,110,100 A | 8/2000 | Talpade |
| 6,125,852 A | 10/2000 | Stevens et al. |
| 6,162,168 A | 12/2000 | Schweich, Jr. et al. |
| 6,183,469 B1 | 2/2001 | Thapliyal et al. |
| 6,190,408 B1 | 2/2001 | Melvin |
| 6,260,552 B1 | 7/2001 | Mortier et al. |
| 6,332,893 B1 | 12/2001 | Mortier et al. |
| 6,402,781 B1 | 6/2002 | Langberg et al. |
| 6,406,420 B1 | 6/2002 | McCarthy et al. |
| 6,409,760 B1 | 6/2002 | Melvin |
| 6,514,194 B2 | 2/2003 | Schweich, Jr. et al. |
| 6,537,198 B1 | 3/2003 | Vidlund et al. |
| 6,575,971 B2 | 6/2003 | Hauck et al. |
| 6,589,160 B2 | 7/2003 | Schweich, Jr. et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,685,627 B2 | 2/2004 | Jayaraman |
| 6,723,038 B1 | 4/2004 | Schroeder et al. |
| 6,746,471 B2 | 6/2004 | Mortier et al. |
| 6,755,777 B2 | 6/2004 | Schweich, Jr. et al. |
| 6,764,510 B2 | 7/2004 | Vidlund et al. |
| 6,776,754 B1 | 8/2004 | Wilk |
| 6,793,618 B2 | 9/2004 | Schweich, Jr. et al. |
| 6,856,076 B2 | 2/2005 | Kim et al. |
| 6,908,424 B2 | 6/2005 | Mortier et al. |
| 6,931,272 B2 | 8/2005 | Burnes |
| 6,970,742 B2 | 11/2005 | Mann et al. |
| 7,044,905 B2 | 5/2006 | Vidlund et al. |
| 7,056,280 B2 | 6/2006 | Buckberg et al. |
| 7,101,395 B2 | 9/2006 | Tremulis et al. |
| 7,125,421 B2 | 10/2006 | Tremulis et al. |
| 7,144,363 B2 | 12/2006 | Pai et al. |
| 7,189,199 B2 | 3/2007 | McCarthy et al. |
| 7,278,964 B2 | 10/2007 | Alferness |
| 7,326,231 B2 | 2/2008 | Phillips et al. |
| 7,452,325 B2 | 11/2008 | Schaller |
| 7,588,582 B2 | 9/2009 | Starksen et al. |
| 7,618,449 B2 | 11/2009 | Tremulis et al. |
| 7,666,193 B2 | 2/2010 | Starksen et al. |
| 7,722,523 B2 | 5/2010 | Mortier et al. |
| 7,753,922 B2 | 7/2010 | Starksen |
| 7,758,637 B2 | 7/2010 | Starksen et al. |
| 7,766,812 B2 | 8/2010 | Schroeder et al. |
| 7,883,538 B2 | 2/2011 | To et al. |
| 8,287,555 B2 | 10/2012 | Starksen et al. |
| 2002/0077524 A1 | 6/2002 | Schweich, Jr. et al. |
| 2002/0183835 A1 | 12/2002 | Taylor et al. |
| 2003/0032979 A1 | 2/2003 | Mortier et al. |
| 2003/0233105 A1 | 12/2003 | Gayton |
| 2004/0152947 A1 | 8/2004 | Schroeder et al. |
| 2004/0193191 A1 | 9/2004 | Starksen et al. |
| 2004/0243227 A1 | 12/2004 | Starksen et al. |
| 2005/0075723 A1 | 4/2005 | Schroeder et al. |
| 2005/0107811 A1 | 5/2005 | Starksen et al. |
| 2005/0137689 A1 | 6/2005 | Salahieh et al. |
| 2005/0209690 A1 | 9/2005 | Mathis et al. |
| 2005/0273138 A1 | 12/2005 | To et al. |
| 2006/0025784 A1 | 2/2006 | Starksen et al. |
| 2006/0122633 A1 | 6/2006 | To et al. |
| 2006/0161040 A1 | 7/2006 | McCarthy et al. |
| 2006/0190030 A1 | 8/2006 | To et al. |
| 2006/0229708 A1 | 10/2006 | Powell et al. |
| 2006/0229717 A1 | 10/2006 | Cohn et al. |
| 2006/0241340 A1 | 10/2006 | Schroeder et al. |
| 2006/0247491 A1 | 11/2006 | Vidlund et al. |
| 2007/0055206 A1 | 3/2007 | To et al. |
| 2007/0100350 A1 | 5/2007 | Deffenbaugh et al. |
| 2007/0112244 A1 | 5/2007 | McCarthy et al. |
| 2007/0112422 A1 | 5/2007 | Dehasdashtian |
| 2007/0112424 A1 | 5/2007 | Spence et al. |
| 2007/0112425 A1 | 5/2007 | Schaller et al. |
| 2007/0118213 A1 | 5/2007 | Loulmet |
| 2008/0172035 A1 | 7/2008 | Starksen et al. |
| 2008/0294177 A1 | 11/2008 | To et al. |
| 2009/0177266 A1 | 7/2009 | Powell et al. |
| 2009/0182417 A1 | 7/2009 | Tremulis et al. |
| 2009/0276038 A1 | 11/2009 | Tremulis et al. |
| 2010/0023056 A1 | 1/2010 | Johansson et al. |
| 2010/0076548 A1 | 3/2010 | Konno |

FOREIGN PATENT DOCUMENTS

| | | |
|---|---|---|
| WO | WO-96/39942 A1 | 12/1996 |
| WO | WO-97/27799 A1 | 8/1997 |
| WO | WO-97/27807 A1 | 8/1997 |
| WO | WO-03/105667 A2 | 12/2003 |
| WO | WO-03/105667 A3 | 12/2003 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C1 | 11/2006 |
| WO | WO-2007/021564 A1 | 2/2007 |
| WO | WO-2008/028135 A2 | 3/2008 |
| WO | WO-2008-028135 A3 | 3/2008 |
| WO | WO-2008/048626 A2 | 4/2008 |
| WO | WO-2008-048626 A3 | 4/2008 |
| WO | WO-2009/052427 A1 | 4/2009 |

OTHER PUBLICATIONS

Final Office Action mailed on Jul. 12, 2007, for U.S. Appl. No. 11/202,474, filed Aug. 11, 2005, 10 pages.
Final Office Action mailed on Jul. 24, 2007, for U.S. Appl. No. 10/741,130, filed Dec. 19, 2003, 10 pages.
Final Office Action mailed on Aug. 13, 2007, for U.S. Appl. No. 10/900,980, filed Jul. 27, 2004, 9 pages.
Final Office Action mailed on Aug. 14, 2007, for U.S. Appl. No. 11/255,400, filed Oct. 20, 2005, 8 pages.
Final Office Action mailed on Aug. 30, 2007, for U.S. Appl. No. 11/232,190, filed Sep. 20, 2005, 9 pages.
Final Office Action mailed on Oct. 30, 2007, for U.S. Appl. No. 10/656,797, filed Sep. 4, 2003, 6 pages.
Final Office Action mailed on Apr. 2, 2008, for U.S. Appl. No. 10/792,681, filed Mar. 2, 2004, 15 pages.
Final Office Action mailed on May 28, 2008, for U.S. Appl. No. 11/270,034, filed Nov. 8, 2005, 10 pages.
Final Office Action mailed on Jun. 4, 2008, for U.S. Appl. No. 11/202,474, filed Aug. 11, 2005, 10 pages.
Final Office Action mailed on Aug. 1, 2008, for U.S. Appl. No. 11/232,190, filed Sep. 20, 2005, 8 pages.
Final Office Action mailed on Sep. 30, 2008, for U.S. Appl. No. 10/900,980, filed Jul. 27, 2004, 7 pages.
Final Office Action mailed on Oct. 14, 2008, for U.S. Appl. No. 10/741,130, filed Dec. 19, 2003, 9 pages.
Final Office Action mailed on Jan. 22, 2009, for U.S. Appl. No. 11/255,400, filed Oct. 20, 2005, 9 pages.
Final Office Action mailed on Mar. 11, 2009, for U.S. Appl. No. 10/656,797, filed Sep. 4, 2003, 10 pages.
Final Office Action mailed on Apr. 10, 2009, for U.S. Appl. No. 11/255,400, filed Oct. 20, 2005, 8 pages.
Final Office Action mailed on May 8, 2009, for U.S. Appl. No. 11/201,949, filed Aug. 30, 2005, 10 pages.
Final Office Action mailed on Jul. 21, 2009, for U.S. Appl. No. 11/270,034, filed Nov. 8, 2005, 8 pages.

(56) References Cited

OTHER PUBLICATIONS

Final Office Action mailed on Sep. 2, 2009, for U.S. Appl. No. 11/232,190, filed Sep. 20, 2005, 8 pages.
Final Office Action mailed on Sep. 28, 2009, for U.S. Appl. No. 11/202,474, filed Aug. 11, 2005, 10 pages.
Final Office Action mailed on Nov. 10, 2009, for U.S. Appl. No. 10/741,130, filed Dec. 19, 2003, 9 pages.
Final Office Action mailed on Mar. 25, 2010, for U.S. Appl. No. 10/900,980, filed Jul. 27, 2004, 8 pages.
Final Office Action mailed on Apr. 15, 2010, for U.S. Appl. No. 11/201,949, filed Aug. 10, 2005, 8 pages.
Final Office Action mailed on May 12, 2010, for U.S. Appl. No. 11/583,627, filed Oct. 18, 2006, 18 pages.
Final Office Action mailed on Jun. 8, 2010, for U.S. Appl. No. 10/792,681, filed Mar. 2, 2004, 17 pages.
Final Office Action mailed on Jul. 26, 2010, for U.S. Appl. No. 11/270,034, filed Nov. 8, 2005, 8 pages.
International Search Report mailed on Feb. 4, 2009, for PCT Patent Application No. PCT/US2008/080368, filed Oct. 17, 2008, 2 pages.
Non-Final Office Action mailed on Aug. 9, 2006, for U.S. Appl. No. 10/900,980, filed Jul. 27, 2004, 17 pages.
Non-Final Office Action mailed on Aug. 22, 2006, for U.S. Appl. No. 10/656,797, filed Sep. 4, 2003, 6 pages.
Non-Final Office Action mailed on Dec. 27, 2006, for U.S. Appl. No. 10/741,130, filed Dec. 19, 2003, 9 pages.
Non-Final Office Action mailed on Dec. 27, 2006, for U.S. Appl. No. 11/270,034, filed Nov. 8, 2005, 8 pages.
Non-Final Office Action mailed on Jan. 4, 2007, for U.S. Appl. No. 11/255,400, filed Oct. 20, 2005, 7 pages.
Non-Final Office Action mailed on Feb. 27, 2007, for U.S. Appl. No. 11/202,474, filed Aug. 11, 2005, 8 pages.
Non-Final Office Action mailed on Mar. 12, 2007, for U.S. Appl. No. 11/232,190, filed Sep. 20, 2005, 11 pages.
Non-Final Office Action mailed on Jul. 24, 2007, for U.S. Appl. No. 10/656,797, filed Sep. 4, 2003, 6 pages.
Non-Final Office Action mailed on Aug. 1, 2007, for U.S. Appl. No. 10/792,681, filed Mar. 2, 2004, 16 pages.
Non-Final Office Action mailed on Aug. 30, 2007, for U.S. Appl. No. 11/270,034, filed Nov. 8, 2005, 10 pages.
Non-Final Office Action mailed on Oct. 19, 2007, for U.S. Appl. No. 11/202,474, filed Aug. 11, 2005, 7 pages.
Non-Final Office Action mailed on Nov. 14, 2007, for U.S. Appl. No. 10/741,130, filed Dec. 19, 2003, 8 pages.
Non-Final Office Action mailed Jan. 9, 2008, for U.S. Appl. No. 11/232,190, filed Sep. 20, 2005, 8 pages.
Non-Final Office Action mailed Jan. 31, 2008, for U.S. Appl. No. 11/255,400, filed Oct. 20, 2005, 7 pages.
Non-Final Office Action mailed on Mar. 27, 2008, for U.S. Appl. No. 10/900,980, filed Jul. 27, 2004, 7 pages.
Non-Final Office Action (Supplementary) mailed on May 9, 2008, for U.S. Appl. No. 11/255,400, filed Oct. 20, 2005, 7 pages.
Non-Final Office Action mailed on Jun. 6, 2008, for U.S. Appl. No. 10/656,797, filed Sep. 4, 2003, 5 pages.
Non-Final Office Action mailed on Aug. 29, 2008, for U.S. Appl. No. 10/792,681, filed Mar. 2, 2004, 15 pages.
Non-Final Office Action mailed on Nov. 26, 2008, for U.S. Appl. No. 11/201,949, filed Aug. 30, 2005, 7 pages.
Non-Final Office Action mailed on Jan. 13, 2009, for U.S. Appl. No. 10/901,555, filed Jul. 27, 2004, 11 pages.
Non-Final Office Action mailed on Jan. 23, 2009, for U.S. Appl. No. 11/232,190, filed Sep. 20, 2005, 8 pages.
Non-Final Office Action mailed on Jan. 23, 2009, for U.S. Appl. No. 11/270,034, filed Nov. 8, 2005, 8 pages.
Non-Final Office Action mailed on Jan. 29, 2009, for U.S. Appl. No. 10/900,980, filed Jul. 27, 2004, 6 pages.
Non-Final Office Action mailed on Mar. 5, 2009, for U.S. Appl. No. 11/202,474, filed Aug. 11, 2005, 10 pages.
Non-Final Office Action mailed on Mar. 27, 2009, for U.S. Appl. No. 10/741,130, filed Dec. 19, 2003, 9 pages.
Non-Final Office Action mailed on Mar. 31, 2009, for U.S. Appl. No. 10/792,681, filed Mar. 2, 2004, 15 pages.
Non-Final Office Action mailed on Aug. 19, 2009, for U.S. Appl. No. 11/583,627, filed Oct. 18, 2006, 14 pages.
Non-Final Office Action mailed on Aug. 25, 2009, for U.S. Appl. No. 10/900,980, filed Jul. 27, 2004, 7 pages.
Non-Final Office Action mailed on Sep. 17, 2009, for U.S. Appl. No. 10/656,797, filed Sep. 4, 2003, 13 pages.
Non-Final Office Action mailed on Oct. 1, 2009, for U.S. Appl. No. 11/201,949, filed Aug. 10, 2005, 10 pages.
Non-Final Office Action mailed on Jan. 19, 2010, for U.S. Appl. No. 11/270,034, filed Nov. 8, 2005, 10 pages.
Written Opinion of the International Searching Authority mailed on Feb. 4, 2009, for PCT Patent Application No. PCT/US2008/080368, filed on Oct. 17, 2008, 6 pages.
Final Office Action mailed on Mar. 17, 2011, for U.S. Appl. No. 11/202,474, filed Aug. 11, 2005, 9 pages.
Final Office Action mailed on Aug. 4, 2011, for U.S. Appl. No. 10/900,980, filed Jul. 27, 2004, 9 pages.
Final Office Action mailed on Nov. 10, 2011, for U.S. Appl. No. 10/792,681, filed Mar. 2, 2004, 20 pages.
Non-Final Office Action mailed on Oct. 25, 2010, for U.S. Appl. No. 11/202,474, filed Aug. 11, 2005, 8 pages.
Non-Final Office Action mailed on Nov. 24, 2010, for U.S. Appl. No. 10/900,980, filed Jul. 27, 2004, 8 pages.
Non-Final Office Action mailed on Oct. 18, 2011, for U.S. Appl. No. 10/741,130, filed Dec. 19, 2003, 9 pages.
Non-Final Office Action mailed on Dec. 22, 2011, for U.S. Appl. No. 11/270,034, filed Nov. 8, 2005, 9 pages.
Notice of Allowance mailed on Aug. 4, 2009, for U.S. Appl. No. 10/901,555, filed Jul. 27, 2004, 7 pages.
Notice of Allowance mailed on Feb. 24, 2010, for U.S. Appl. No. 10/656,797, filed Sep. 4, 2003, 10 pages.
Notice of Allowance mailed on Apr. 28, 2010, for U.S. Appl. No. 10/901,019, filed Jul. 27, 2004, 7 pages.
Notice of Allowance mailed on Nov. 17, 2010, for U.S. Appl. No. 11/232,190, filed Sep. 20, 2005, 11 pages.
Notice of Allowance mailed on Jun. 11, 2012, for U.S. Appl. No. 10/741,130, filed Dec. 19, 2003.
Final Office Action mailed on Nov. 28, 2011, for U.S. Appl. No. 11/201,949, filed Aug. 10, 2005, 8 pages.
Final Office Action mailed on Jun. 6, 2011, for U.S. Appl. No. 11/201,949, filed Aug. 10, 2005, 10 pages.
Non-Final Office Action mailed on Sep. 14, 2010, for U.S. Appl. No. 11/201,949, filed Aug. 10, 2005, 10 pages.
Non-Final Office Action mailed on Jun. 21, 2013, for U.S. Appl. No. 11/201,949, filed Aug. 10, 2005, 8 pages.
Non-Final Office Action mailed on Mar. 30, 2012, for U.S. Appl. No. 11/202,474, filed Aug. 11, 2005, 9 pages.
Notice of Allowance mailed on Jul. 14, 2009, for U.S. Appl. No. 11/255,400, filed Oct. 20, 2005, 6 pages.

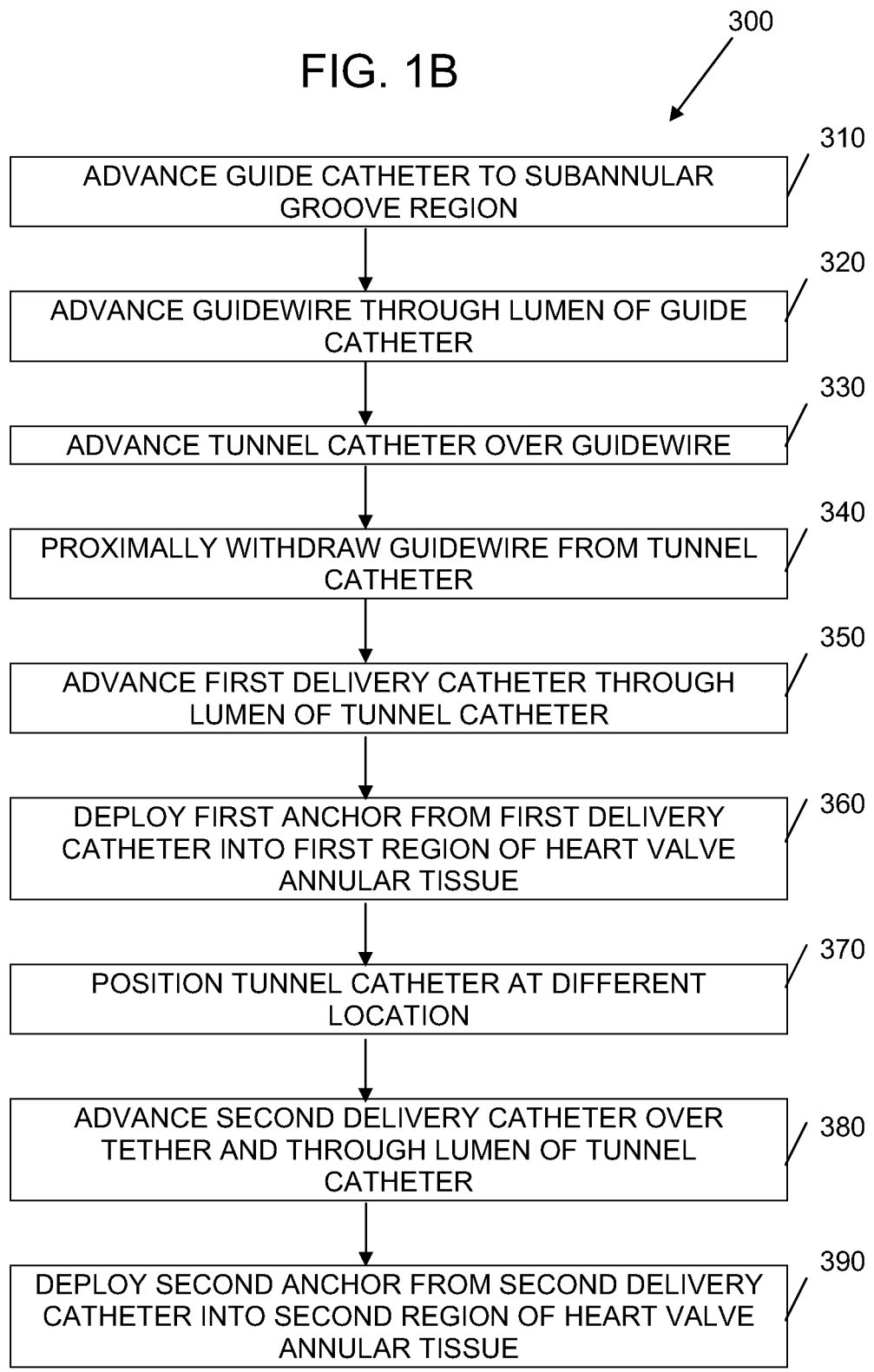

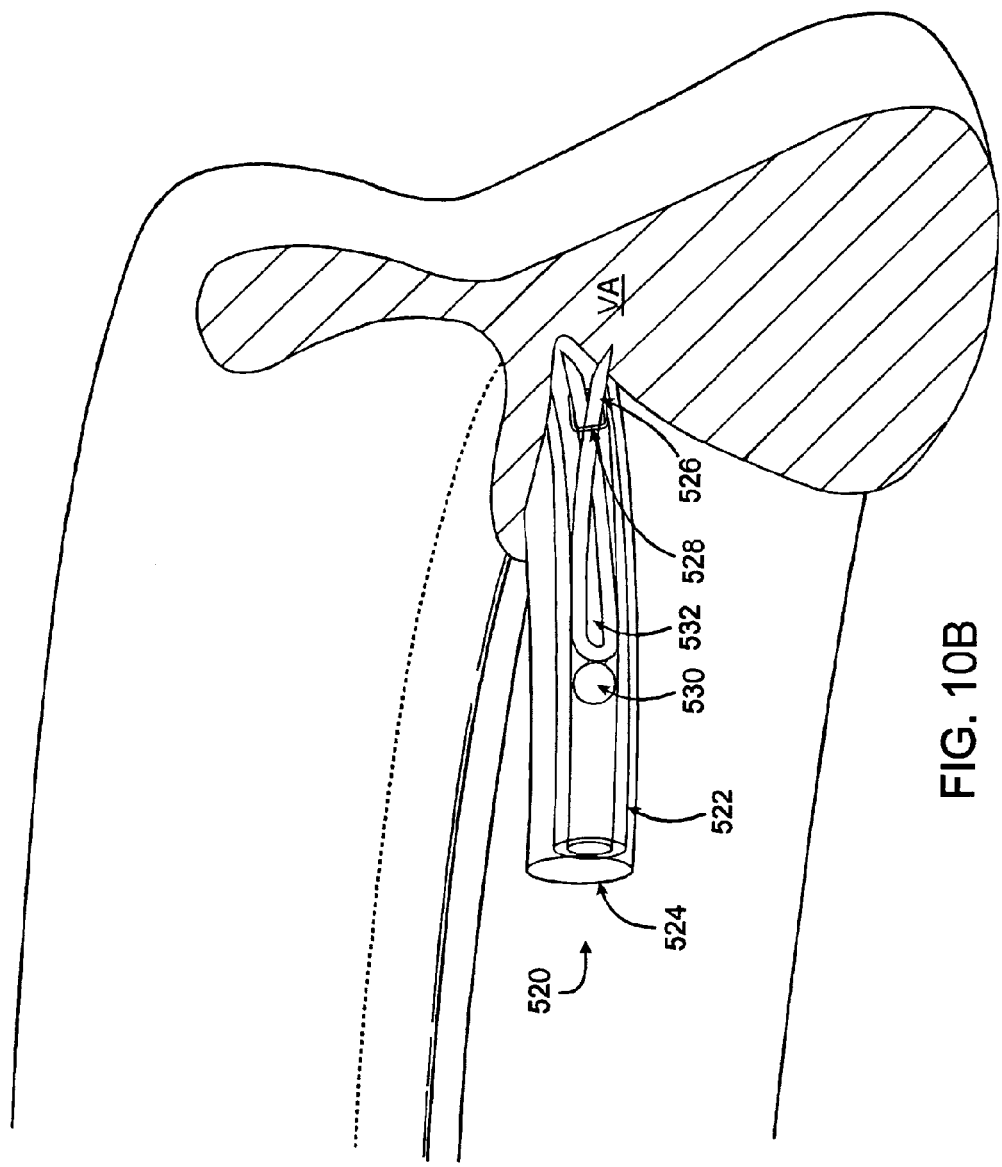

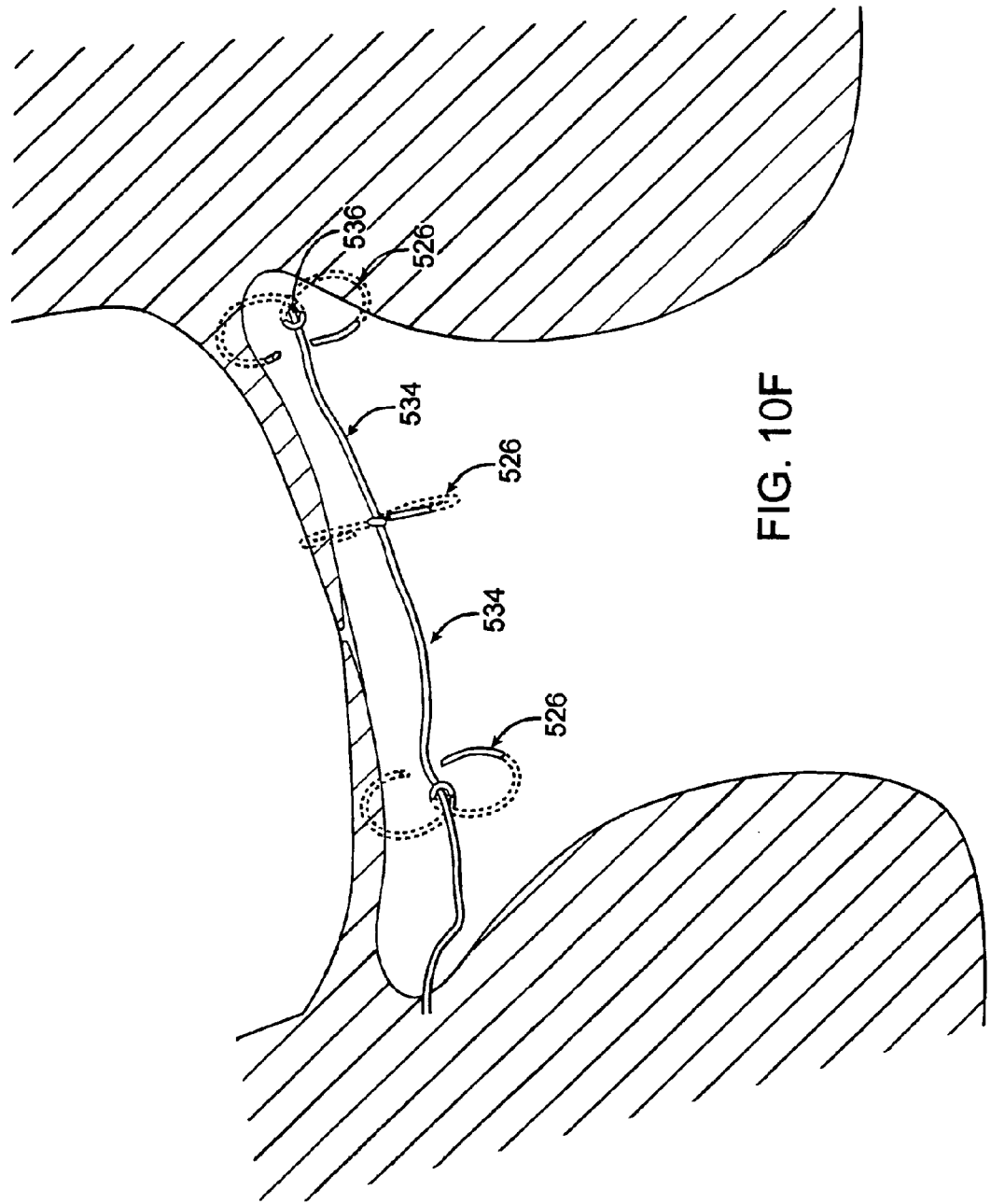

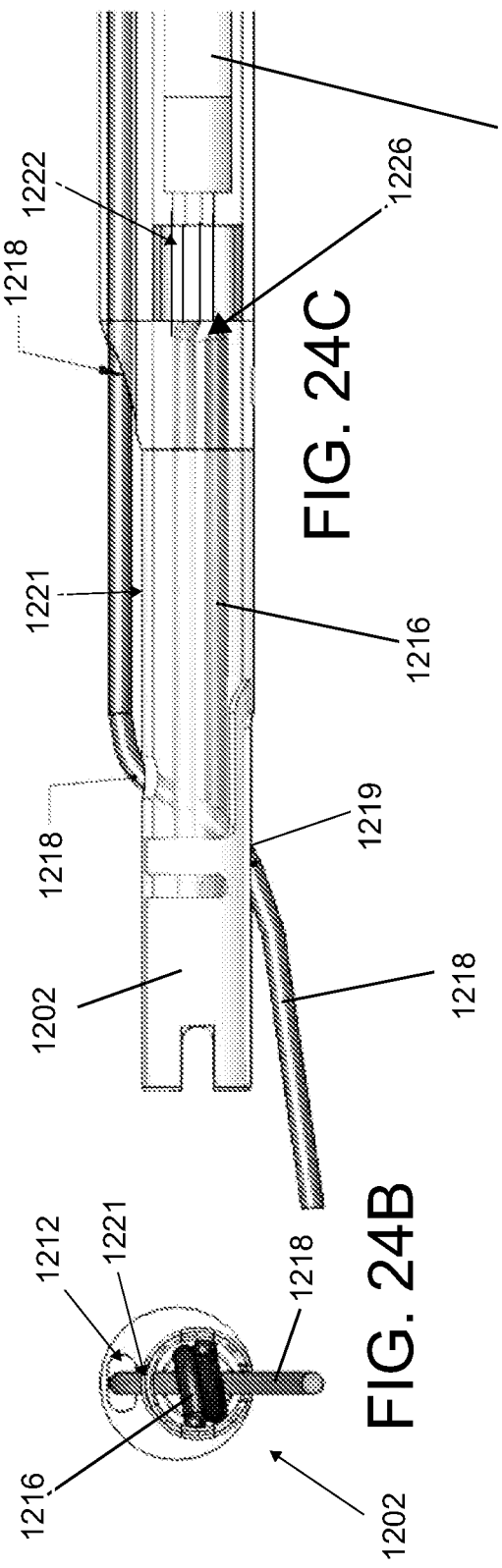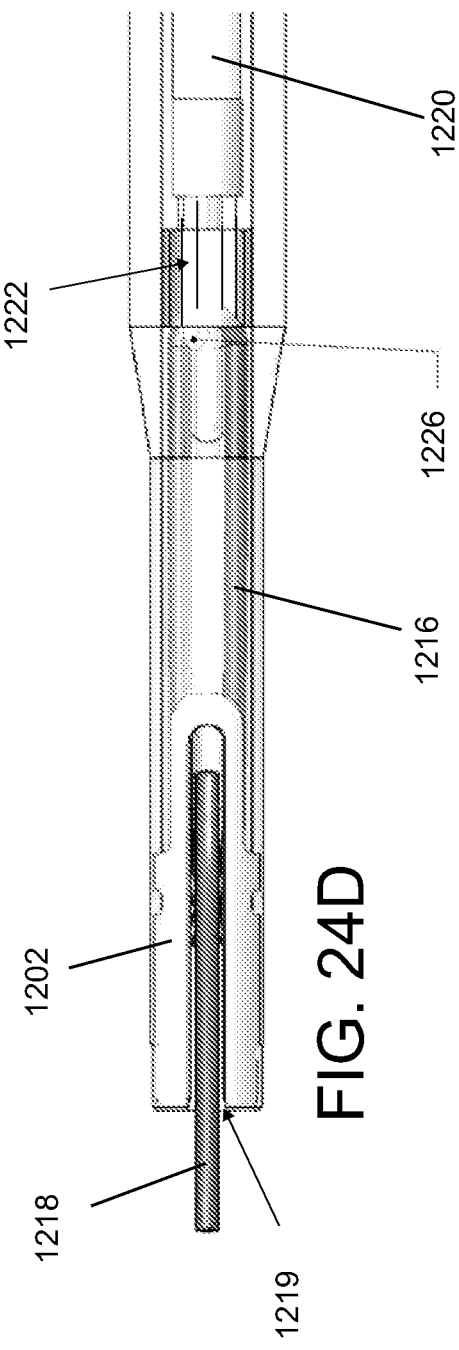

SYSTEMS AND METHODS FOR CARDIAC REMODELING

CROSS-REFERENCE TO RELATED APPLICATIONS

The present application claims priority under 35 U.S.C. 119(e) to U.S. Provisional Application No. 60/981,423 filed on Oct. 19, 2007, which is hereby incorporated by reference in its entirety.

BACKGROUND OF THE INVENTION

Blood returning to the heart from the peripheral circulation and the lungs generally flows into the atrial chambers of the heart and then to the ventricular chambers, which pump the blood back out of the heart. During ventricular contraction, the atrio-ventricular valves between the atria and ventricles, i.e. the tricuspid and mitral valves, close to prevent backflow or regurgitation of blood from the ventricles back to the atria. The closure of these valves, along with the aortic and pulmonary valves, maintains the unidirectional flow of blood through the cardiovascular system. Disease of the valvular apparatus can result in valve dysfunction, where some fraction of the ventricular blood regurgitates back into the atrial chambers.

There are several possible structural causes for atrio-ventricular valve dysfunction, including: loss of pliability of the annulus leading to decreased contractibility; widening of the annulus; thickening, shortening or swelling of the leaflets; dilation of the ventricle; elongation or breaking of the chordae tendineae; and elongation of the attachment of the chordae tendineae with the papillary muscles or ventricular wall. Structural abnormalities at one or more of these anatomical sites may eventually lead to loss of coaptation of the leaflets, loss of competence of the valve and decreased efficiency of the heart as a one-way pumping mechanism. When the latter occurs, various signs and symptoms may be seen in patients, including breathlessness or lack of stamina and heart murmurs.

Traditional treatment of heart valve stenosis or regurgitation, such as mitral or tricuspid regurgitation, involves an open-heart surgical procedure to replace or repair the valve. Currently accepted treatments of the mitral and tricuspid valves include: valvuloplasty, in which the affected leaflets are remodeled to perform normally; repair of the chordae tendineae and/or papillary muscle attachments; and surgical insertion of an "annuloplasty" ring. This requires suturing a flexible support ring over the annulus to constrict the radial dimension. Other surgical techniques to treat heart valve dysfunction involve fastening (or stapling) the valve leaflets to each other or to other regions of the valve annulus to improve valve function (see, e.g., U.S. Pat. No. 6,575,971).

BRIEF SUMMARY OF THE INVENTION

Described herein are devices and methods for improving the hemodynamic function of a patient. In particular, a first device adapted to reshape an atrio-ventricular valve is used with a second device configured to further alter the blood flow through the valve. The first device may be an implant positioned in the subvalvular space of a ventricle. The second device may be an annuloplasty implant, a non-annulus valve apparatus implant, a ventriculoplasty implant, or a cardiac rhythm management device.

In one embodiment, a method for reshaping a heart is provided. The method comprises accessing a first cardiac tissue at a subvalvular space of a ventricle, positioning a first therapy device adjacent the first cardiac tissue using a first delivery tool, reconfiguring the first cardiac tissue using the first therapy device and reconfiguring a second cardiac tissue at a different location from the first cardiac tissue using a second therapy device. Thus, more than one therapy device may be used. In some embodiments, a septolateral dimension of a heart chamber is reduced.

In one embodiment, a method for treating an atrio-ventricular valve is provided. The method comprises accessing a first cardiac tissue at a subvalvular space of an atrio-ventricular valve, wherein the first cardiac tissue is non-leaflet cardiac tissue. Sometimes, the subannular groove region of the left ventricle may be specifically accessed. A first therapy device may be positioned adjacent to the first cardiac tissue using a first delivery tool and the first therapy device may be used to reconfigure the first cardiac tissue. A second therapy device adapted to alter flow through the valve may be also implanted. Occasionally, a third therapy device adapted to alter flow through the valve is also implanted. In some embodiments, the first therapy device comprises a first plurality of tissue anchors slidably coupled to a first tether. Reconfiguring the first cardiac tissue may occur before implanting the second therapy device.

In some further embodiments, implanting the second therapy device may comprise accessing a second cardiac tissue inferior to a third order chordae tendineae, positioning the second therapy device adjacent the second cardiac tissue and reconfiguring the second cardiac tissue using the second therapy device. The second cardiac tissue may be inferior or superior to a papillary muscle, and sometimes may be oriented generally perpendicular to a longitudinal axis of a ventricle, or generally parallel to the base of the ventricle. The second therapy device may be selected from a group consisting of: an annuloplasty device, a myocardial tensioning device, a myocardial compression device, a valve leaflet clip, a chordae tendineae clip device, a left ventricular assist device, a cardiac rhythm management device, and the like.

Sometimes, the method of treatment comprises passing a guide catheter in a retrograde direction through an aorta, passing a first delivery catheter through the guide catheter and toward the first cardiac tissue, withdrawing the first delivery catheter from the guide catheter after reconfiguring the first cardiac tissue using the first device, passing a second delivery catheter through the guide catheter and toward the second cardiac tissue, and manipulating a cinching member of the first therapy device. In some further embodiments, manipulating the cinching member of the first therapy device is performed in the left ventricle. Also, in some particular embodiments, the second therapy device comprises a means for reducing a left ventricle dimension.

In another embodiment, a method for reducing valve regurgitation is provided. The method comprises accessing a ventricle in a patient with a pre-existing annuloplasty implant, positioning a therapy device adjacent a wall of the ventricle, and reconfiguring the wall of the ventricle using the therapy device. The therapy device may comprise a plurality of tissue anchors movably coupled to a tether. At least one tissue anchor may be self-attaching or self-securing. The method may be performed to reduce a distance between a first papillary muscle and a second papillary muscle in the ventricle, or reduce a distance between a valve leaflet and a papillary muscle. The papillary muscle may be attached to the valve leaflet by a chordae tendineae, or may be an unassociated papillary muscle.

In still another embodiment, a kit for altering atrio-ventricular valve flow is provided. The kit comprises a guide catheter, a first delivery catheter configured for insertion into the guide catheter, a first plurality of tissue anchors slidably coupled to a first tether and configured for loading into the first delivery catheter, a second delivery catheter configured for insertion into the guide catheter, and a second plurality of tissue anchors slidably coupled to a second tether and configured for loading into the second delivery catheter. In some embodiments, one or both of the delivery catheters is preloaded with a plurality of tissue anchors.

BRIEF DESCRIPTION OF THE DRAWINGS

The structure and method of using the invention will be better understood with the following detailed description of embodiments of the invention, along with the accompanying illustrations, in which:

FIG. 1B is a flowchart representation of a method for delivering at least two anchors into a region of a heart valve annulus;

FIGS. 10A through 10F demonstrate a method for applying anchors to a valve annulus and cinching the anchors to tighten the annulus, using an anchor delivery device;

FIG. 24B is a front view of the delivery catheter of FIG. 24A, and FIGS. 24C and 24D are side and bottom views, respectively, of a portion of the delivery catheter of FIG. 24A;

DETAILED DESCRIPTION OF THE INVENTION

While existing treatment options, such as the implantation of an annuloplasty ring or edge-to-edge leaflet repair, have been developed to treat structural abnormalities of the disease process, these treatments may fail to return the patient to a normal hemodynamic profile. Furthermore, atrio-ventricular valve regurgitation itself can also cause secondary changes to the cardiac function. For example, compensatory volume overload of the left ventricle may occur over time to maintain the net forward flow from the ventricle. This in turn will cause ventricular dilation, and further worsen mitral valve regurgitation by reducing valve coaptation. Ventricular dilation may also cause non-structural changes to the heart that can cause arrhythmias or electrophysiological conduction delays.

Devices, systems and methods are generally described herein for reshaping or remodeling atrio-ventricular valves. In some variations, procedural efficiencies may be gained by facilitating the delivery of two or more treatment devices to one or more treatment sites using some common delivery components. The implantation procedures may be transvascular, minimally invasive or other "less invasive" surgical procedures, but the procedures can also be performed with open or limited access as well.

When used for treatment of a cardiac valve dysfunction, the methods may generally involve contacting an anchor delivery device, delivering a plurality of slidably coupled anchors from the anchor delivery device, and drawing the anchors together to tighten the annulus or annular tissue. Devices include an elongate catheter with a housing at or near the distal end for releasably housing a plurality of coupled anchors, as well as delivery devices for facilitating advancement and/or positioning of an anchor delivery device. Self-securing anchors having any of a number of different configurations may be used in some embodiments. Additional devices include delivery devices for facilitating delivery and/or placement of an anchor delivery device at a treatment site.

Valve Reshaping

Figure 1A:
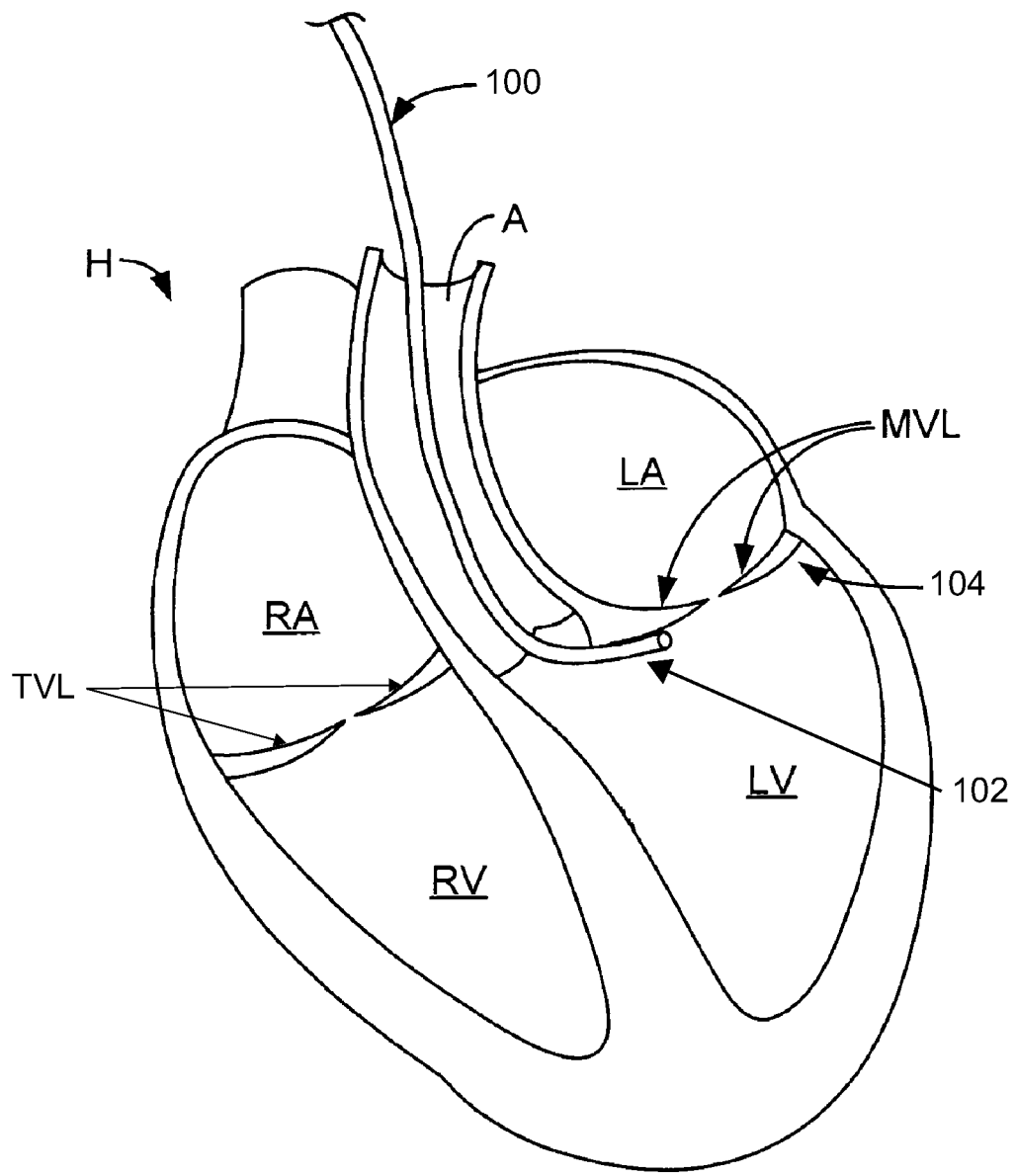
FIG. 1A is a cross-sectional view of a heart with a guide catheter device advanced through the aorta into the left ventricle.

Referring now FIG. 1A, a cross-sectional depiction of a heart H is shown with an anchor delivery device guide catheter 100 advanced in a retrograde direction through the aorta A and into the left ventricle LV. Retrograde, as used herein, generally refers to a direction opposite the expected flow of blood. In one embodiment, this access route is used to reach the subvalvular space 106. Guide catheter 100 is generally a flexible elongate catheter which may have one or more curves or bends toward its distal end to facilitate placement of the distal end 102 of the catheter 100 at the desired location. The distal end 102 of guide catheter 100 may be configured to be positioned at an opening into the subvalvular space 106 or within the subvalvular space 106, such that subsequent delivery devices may be passed through guide catheter 100 into the subvalvular space 106. Although the retrograde aortic access route preferably starts from a percutaneous or peripheral access site, in some embodiments of the invention, aortic access may be achieved by an incision in the ascending aorta, descending aorta, aortic arch or iliac arteries, following surgical, thorascopic or laparoscopic access to a body cavity.

Access to the other chambers of the heart may be performed through percutaneous or venous cut-down access, including but not limited to transjugular, subclavian and femoral vein access routes. When venous access is established, access to the right atrium RA, the right ventricle RV, the tricuspid valve TV and other right-sided cardiac structures can occur. Furthermore, access to left-sided heart structures, such as the left atrium LA, left ventricle LV, mitral valve and the aortic valve, may be subsequently achieved by performing a transseptal puncture procedure, which is discussed in greater detail below.

Access to the heart H may also be transthoracic, with a delivery device being introduced into the heart via an incision or port in the heart wall. Open heart surgical procedures may also be used to provide access for the methods and devices described herein. In some embodiments, hybrid access involving a combination of access methods described herein may be used. In one specific example, dual access to a valve may be achieved with a combination of venous and arterial access sites. User manipulation of both ends of a guidewire placed across a valve may improve positioning and control of the catheter and the implants. In other examples of hybrid access, both minimally invasive and surgical access is used to implant one or more cardiac devices.

Other embodiments of the invention also include treatment of the tricuspid valve annulus, tissue adjacent the tricuspid valve leaflets TVL, or any other cardiac or vascular valve. Thus, although the description herein discloses specific examples of devices and methods of the invention for mitral valve repair, the devices and methods may be used in any suitable procedure, both cardiac and non-cardiac. For example, in other embodiments, the mitral valve reshaping devices and procedures may be used with the tricuspid valves also, and certain embodiments may also be adapted for use with the pulmonary and aortic valves. Likewise, the other examples provided below are directed to the left ventricle, but the devices and methods may also be adapted by one of ordinary skill in the art for use in the right ventricle or either atrium. The devices and methods may also be used with the great vessels of the cardiovascular system, for example, to treat aortic root dilatation.

FIG. 1B is a flowchart of a method 120 for deploying at least two anchors in the region of a heart valve annulus. As shown there, this illustrative method comprises advancing a guide catheter to the subannular groove region 122, advancing a guidewire through a lumen of the guide catheter 124, advancing a tunnel catheter over the guidewire 126, and proximally withdrawing the guidewire from the tunnel catheter 128. After the guidewire has been proximally withdrawn, a first delivery catheter may be advanced through the lumen of the tunnel catheter 130 and a first anchor may be deployed into a first region of the heart valve annular tissue 132. The first anchor may then be fixedly attached or otherwise secured to a guide element, such as a tether. In this way, after the anchor is deployed, the guide element may remain attached to the anchor and the guide element may be used as a track or monorail for the advancement of additional delivery catheters thereover.

The guide element may be made from any suitable or desirable biocompatible material. The guide element may be braided or not braided, woven or not woven, reinforced or impregnated with additional materials, or may be made of a single material or a combination of materials. For example, the guide element may be made from a suture material (e.g., absorbable suture materials such as polyglycolic acid and polydioxanone, natural fibers such as silk, and artificial fibers such as polypropylene, polyester, polyester impregnated with polytetrafluoroethylene, nylon, etc.), may be made from a metal (absorbable or non-absorbable), may be made from a metal alloy (e.g., stainless steel), may be made from a shape memory material, such as a shape memory alloy (e.g., a nickel titanium alloy), may be made from combinations thereof, or may be made from any other biocompatible material. In some variations, when pulled proximally, the guide element will cinch or reduce the circumference of the atrio-ventricular valve annulus or the annular tissue. In certain variations, the guide element may be in the form of a wire. The guide element may include multiple layers, and/or may include one or more coatings. For example, the guide element may be in the form of a polymer-coated wire. In certain variations, the guide element may be formed of a combination of one or more sutures and one or more wires. As an example, the guide element may be formed of a suture that is braided with a wire. In some variations, the guide element may be formed of one or more electrode materials. In certain variations, the guide element may be formed of one or more materials that provide for the telemetry of information (e.g., regarding the condition of the target site).

In some variations, the guide element may include one or more therapeutic agents (e.g., drugs, such as time-release drugs). As an example, the guide element may be partially or entirely coated with one or more therapeutic agents. In certain variations, the guide element may be used to deliver one or more growth factors and/or genetic regenerative factors. In some variations, the guide element may be coated with a material (e.g., a polymer) that encapsulates one or more therapeutic agents, or in which one or more therapeutic agents are embedded. The therapeutic agents may be used, for example, to treat the target site to which the guide element is fixedly attached or otherwise secured. In certain variations, the guide element may include one or more lumens through which a therapeutic agent can be delivered.

After the first anchor has been deployed in the region of the heart valve annular tissue, the first delivery catheter may be withdrawn proximally and the tunnel catheter may then be positioned at a different location about the subannular groove region 134. A second delivery catheter may then be advanced over the guide element through the lumen of the tunnel catheter 136. During advancement of the second delivery catheter over the guide element, the guide element may enter the second delivery catheter through an opening at its distal end, and exit the second delivery catheter through an opening in its side wall that is proximal to its distal end. Alternatively, the guide element may enter the second delivery catheter through an opening at its distal end, and exit the second delivery catheter through an opening at its proximal end. After the second delivery catheter has been advanced over the guide element through the lumen of the tunnel catheter, a second anchor is deployed into a second region of the heart valve annular tissue 138.

Figure 2A:
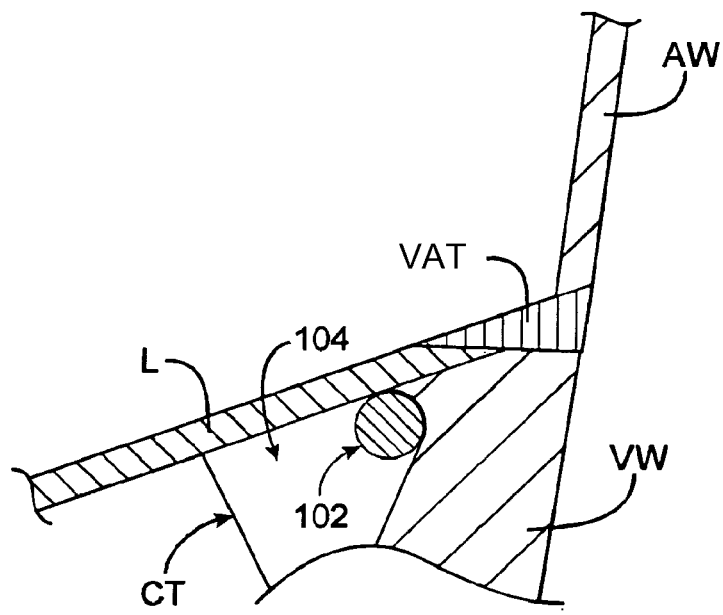
FIGS. 2A and 2B are cross-sectional views of a portion of a heart, schematically illustrating the positioning of a flexible device for treatment of a mitral valve annulus.

As illustrated in FIG. 2A, a distal portion 102 of the delivery device 100 is positioned in a desired location under a valve leaflet L and adjacent a ventricular wall VW. The valve annulus VA generally comprises an area of heart wall tissue at the junction of the ventricular wall VW and the atrial wall AW that is relatively fibrous and, thus, significantly stronger than leaflet tissue and other heart wall tissue. It is noted, however, that considerable structural variations of the annulus exist within patient populations and that attempted delivery of an implant to the valve annulus VA may instead contact or attach to the tissue adjacent to the valve annulus. The term "annular tissue" as used herein shall include the valve annulus and the tissue adjacent or surrounding the valve annulus.

The distal portion 102 of the delivery device 100 may be advanced into position generally under the valve annulus VA by any suitable technique, some of which are described below. The distal portion 102 of the delivery device 100 may be used to deliver anchors to the valve annular tissue, to stabilize and/or expose the annulus, or both. In one embodiment, using a delivery device 100 having a flexible elongate body as shown in FIG. 1, a flexible distal portion 102 may be positioned in the left ventricle LV at the level of the mitral valve leaflets MVL using any of a variety of access routes described herein. The distal portion 102 may be advanced to a region 104 under the posterior valve leaflet. Referring to FIG. 2A, in some variations the region 104 may be generally bordered by the inner surface of the ventricular wall VW, the inferior surface of valve leaflets L, and the third order chordae tendineae CT connected directly to the ventricular wall VW and the leaflet L. It has been found that when a flexible anchor delivery device 100 is passed, for example, under the mitral valve via an intravascular approach, the delivery device 100 may be inserted into the space 104 and advanced along the subannular groove region 104 either partially or completely around the circumference of the valve. Other examples of deployment locations are described elsewhere herein. Once in the region 104, the distal portion 102 of the delivery device 100 may be positioned proximate to the intersection of the valve leaflet(s) and the ventricular wall VW, which is near to the valve annulus VA. These are but examples of possible access routes of an anchor delivery device to a valve annulus, and any other access routes may be used.

In some embodiments, the guide catheter 100 may comprise a curvable portion with a radius in an expanded/curved state that is greater than a radius of the valve annulus or the subannular groove region. The relative size of this portion of the guide catheter 100, when positioned within the smaller sized ventricle, may exert a radially outward force that can improve the surface contact between guide catheter 100 and the left ventricle LV. For example, in one embodiment guide catheter 100 in the expanded state has a radius about 25%-50% larger that the valve annulus or ventricle chamber.

In some variations, the distal portion 102 of the delivery device 100 may include a shape-changing portion which enables distal portion 102 to conform to the shape of the valve annulus VA, the region 104, or other portion of the heart chamber. The delivery device 100 may be introduced through the vasculature with the shape-changing distal portion in a generally straight, flexible configuration. Once the delivery device 100 is generally positioned beneath the leaflet in proximity to the intersection between the leaflet and the interior ventricular wall, the shape of the distal portion 102 may be changed to conform to the annulus and the shape may be "locked" to provide sufficient stiffness or rigidity to permit the application of force from the distal portion 102 to the annulus or annular tissue.

In some embodiments, a shape-changing portion may be sectioned, notched, slotted or segmented and one of more tensioning members such as tensioning cords, wires or other tensioning devices coupled with the shape-changing portion may be used to shape and rigidify distal portion 102. A segmented distal portion, for example, may include multiple segments coupled with two tensioning members, each providing a different direction of articulation to the distal portion. A first bend may be created by tensioning a first member to give the distal portion a C-shape or similar shape to conform to the annular tissue, while a second bend may be created by tensioning a second member to articulate the C-shaped member upwards against the annular tissue. In another embodiment, a shaped expandable member, such as a balloon, may be coupled with the distal portion 102 to provide for shape changing/deforming.

For example, in transthoracic delivery methods and other embodiments, the distal portion 102 may be shaped, and the method may involve introducing distal portion 102 under the valve leaflets. The shaped distal portion 102 may be rigid or formed from any suitable material such as spring stainless steel, a super-elastic or shape memory material such as nickel-titanium alloy (e.g., Nitinol), or the like. In embodiments configured for open surgical access, the delivery devices may be made with stiffer materials when the maneuverability through a transvascular route is not required, but in other embodiments, flexible, catheter-like delivery devices may still be used with open surgical procedures.

Figure 2B:
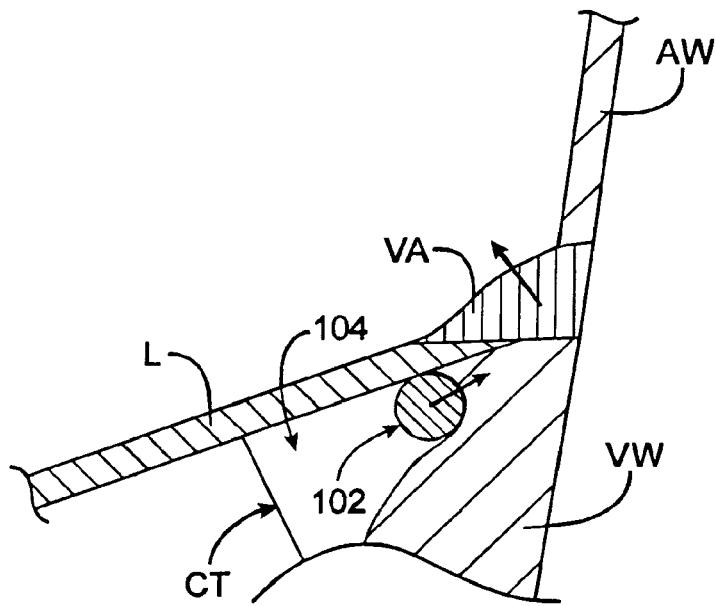

In addition to delivering anchors to the annular tissue, the delivery device 100 (and specifically distal portion 102) may be used to stabilize and/or expose the valve annulus or annular tissue. Such stabilization and exposure are described fully in U.S. patent application Ser. No. 10/656,797, which is hereby incorporated by reference in its entirety. For example, once the distal portion 102 is positioned generally under the annular tissue, force may be applied to the distal portion 102 to stabilize the valve annulus VA or annular tissue, as shown in FIG. 2B. Such force may be directed in any suitable direction to expose, position and/or stabilize the annulus or annular tissue. In another example, an upward and lateral force is shown in FIG. 2B by the solid-headed arrow drawn from the center of the distal portion 102. In other examples, only upward, only lateral, or any other suitable force(s) may be applied. With application of force to the distal portion 102, the annular tissue may rise or project outwardly, thus exposing the annular tissue for easier viewing or access. The applied force may also stabilize the valve annulus VA or valve annular tissue, also facilitating surgical procedures and visualization.

Some embodiments of the invention may include a stabilization component as well as an anchor delivery component. For example, some embodiments may include two flexible members, one for contacting the atrial side of a valve annulus and the other for contacting the ventricular side. In some embodiments, such flexible members may be used to "clamp" the annulus between them. One of such members may be an anchor delivery member and the other may be a stabilization member, for example. Any combination and configuration of stabilization and/or anchor delivery members is contemplated.

Figure 2C:
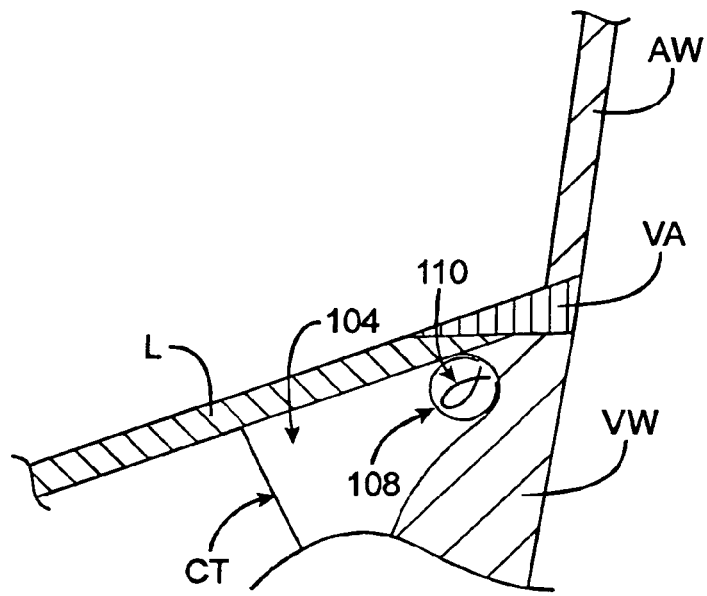
FIGS. 2C and 2D are cross-sectional views of a portion of a heart, showing the positioning and deployment of a flexible anchor delivery device for treatment of a mitral valve annulus.
Figure 2D:
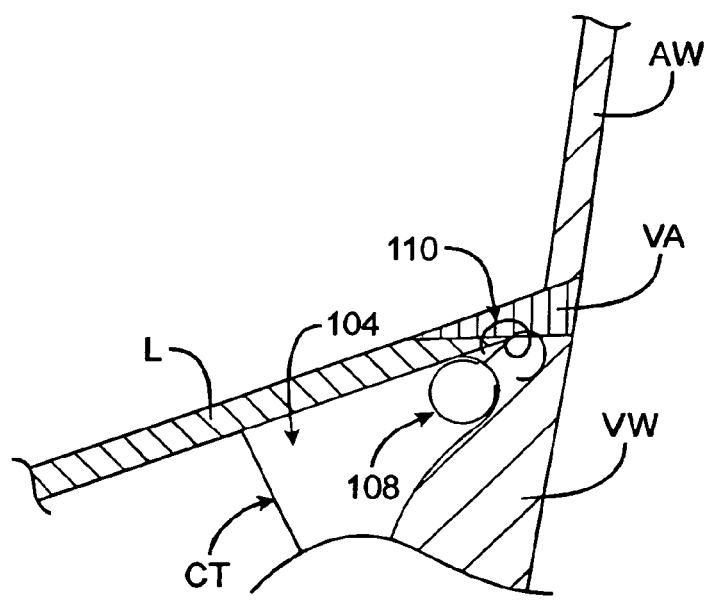

Referring now to FIGS. 2C and 2D, an anchor delivery device 108 is schematically shown delivering an anchor 110 to a valve annulus VA. Anchor 110 is shown first housed within delivery device 108 in FIG. 2C and then delivered to the annulus VA, as depicted in FIG. 2D. Of course, although the delivery and position of the anchor 110 is described with respect to the valve annulus VA, one or more anchors 110 may be secured to the valve annulus VA or other structures accessible from the region 104. As is shown, in some embodiments, anchors 110 may have a relatively straight configuration when housed in delivery device 108, with two sharpened tips and a loop in between the tips. Upon deployment from delivery device 108, the tips of anchor 110 may curve in opposite directions to form two semi-circles, circles, ovals, overlapping helices or the like. Additional anchor embodiments are described below, and may also be found in U.S. patent application Ser. No. 11/202,474, which is hereby incorporated by reference in its entirety. Multiple coupled anchors 110 may be delivered, and the anchors 110 may be drawn together to tighten the valve annulus.

Although delivery device 108 is shown having a circular cross-sectional shape in FIGS. 2C and 2D, it may alternatively have any other suitable shape. In one embodiment, for example, it may be advantageous to provide a delivery device having an ovoid or elliptical cross-sectional shape. Such a shape may help ensure that the device is aligned, when positioned between a corner formed by a ventricular wall and a valve leaflet, such that one or more openings in the delivery device is oriented to deliver the anchors into valve annulus tissue. To further enhance contacting of the annular tissue and/or orientation of the delivery device, some embodiments may further include an expandable member, coupled with the delivery device, which expands to urge or press or wedge the delivery device into the corner formed by the ventricle wall and the leaflet to contact the valve annulus. Such enhancements are described further below.

Figure 1C:
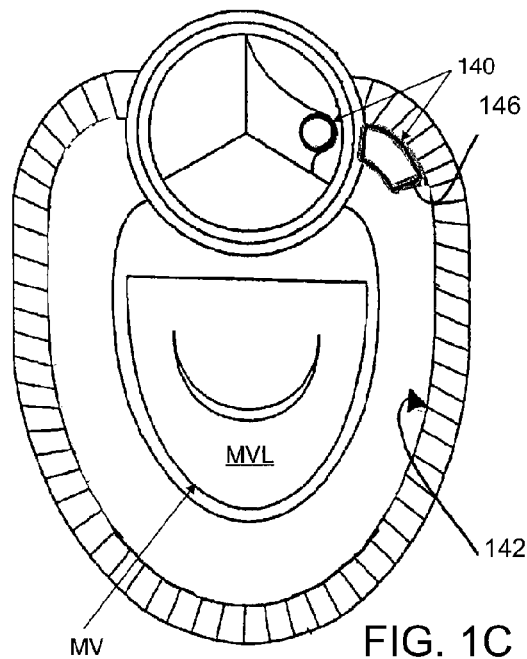
FIGS. 1C to 1K provide a detailed depiction of a method for advancing at least two delivery catheters to the subannular groove region of a heart valve to deliver at least two anchors into a region of annular tissue.
Figure 1D:
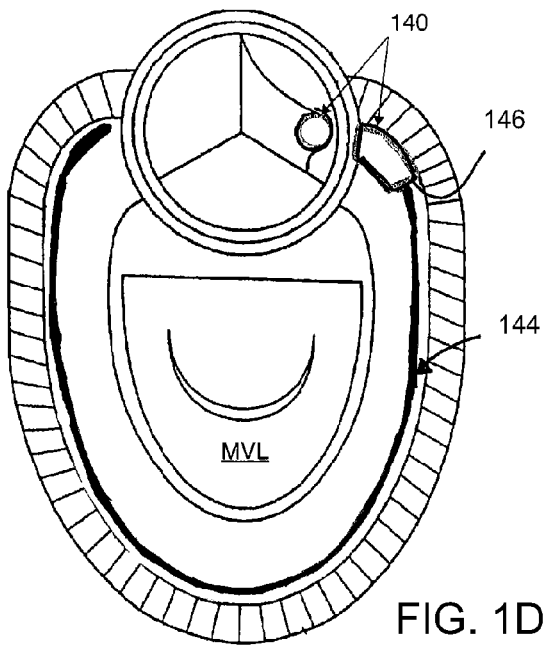

FIGS. 1C to 1K provide a more detailed depiction of the method shown in flowchart form in FIG. 1B. In FIGS. 1C to 1K, the mitral valve MV of FIG. 1A is depicted schematically from an inferior perspective looking up, but in other embodiments the tricuspid valve may be accessed. Referring to FIG. 1C, a guide catheter 140 is advanced to subannular groove region 142 using any of the access routes (or any other suitable access routes) previously described. After guide catheter 140 has been positioned at the desired location in subannular groove region 142, a guidewire 142 is advanced through the lumen of guide catheter 140. The guidewire 144 may then be advanced beyond the distal end 146 of guide catheter 140, so that guidewire 144 extends further along subannular groove region 142 than guide catheter 140, as shown in FIG. 1D.

Figure 1E:
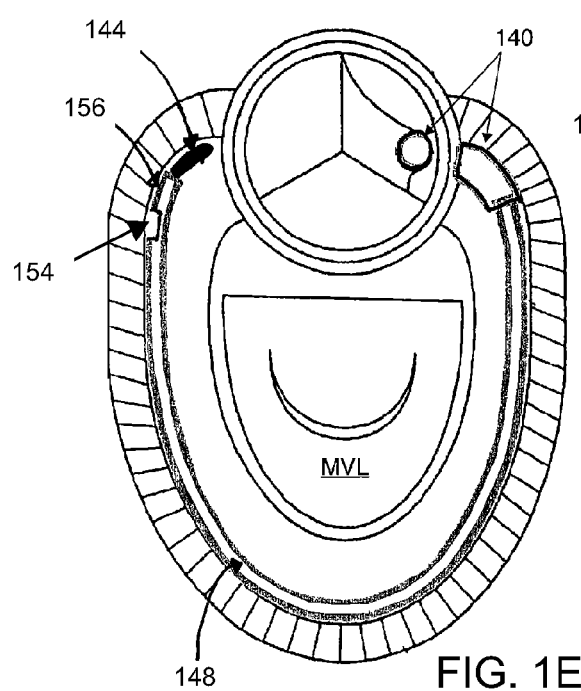

After the guidewire 144 has been positioned in the subannular groove region 142, a tunnel catheter 148 may be advanced through guide catheter 140, over guidewire 144, which is shown in FIG. 1E. Tunnel catheter 148 may be any suitable catheter, and in some instances, it is desirable that the tunnel catheter be pre-shaped or pre-formed at its distal end, such as the tunnel catheter illustrated in FIG. 1E. The tunnel catheter may have a pre-shaped distal portion comprising a curve. In this way, the tunnel catheter may more easily conform to the geometry of the atrio-ventricular valve. It should also be understood that any of the catheters or guidewires described here may be pre-shaped or pre-formed to include any number of suitable curves. Of course, the guidewires and/or catheters described here may also be steerable.

Figure 1F:
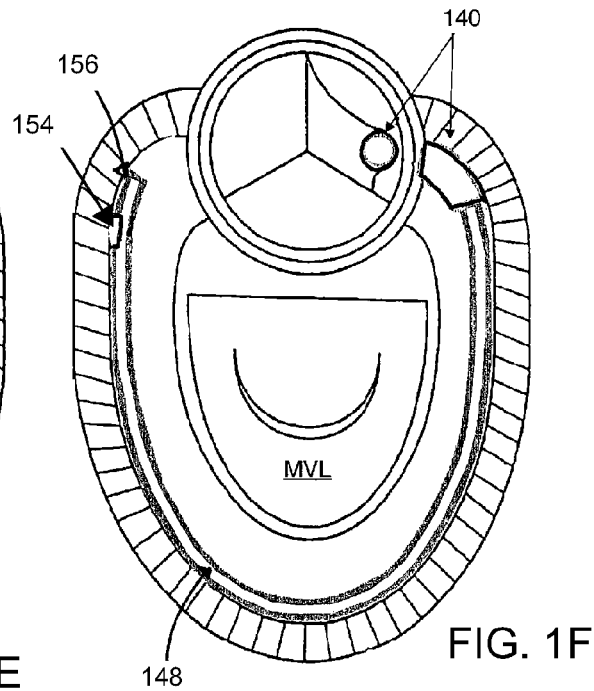
Figure 1G:
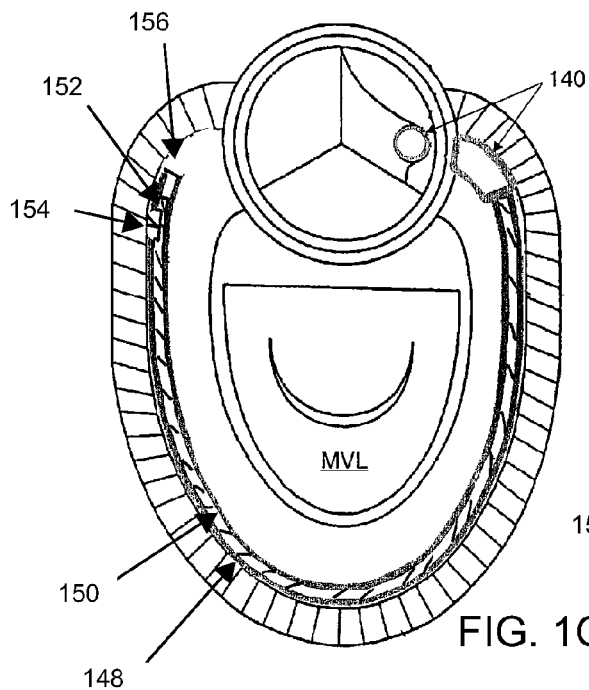
Figure 1H:
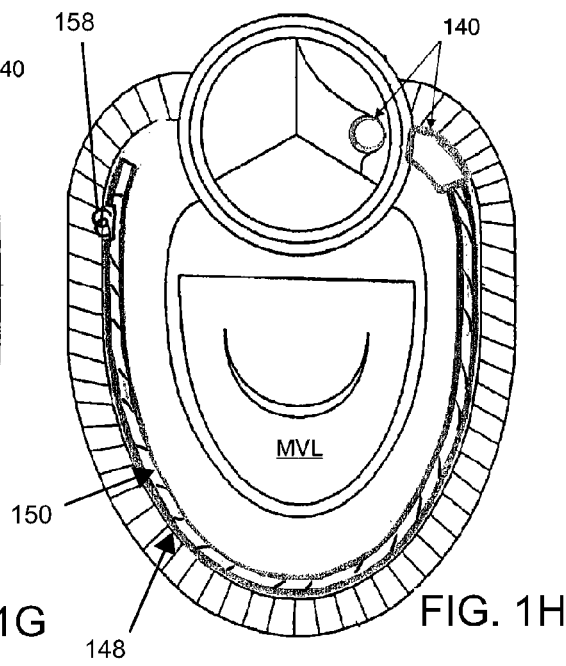
Figure 1I:
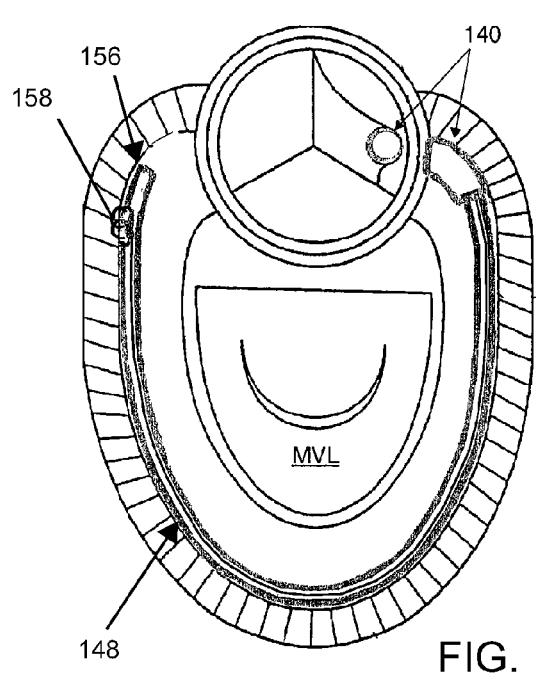

After tunnel catheter 148 has been positioned in the subannular groove region 142, guidewire 144 may be withdrawn proximally as shown in FIG. 1F. After guidewire 144 has been withdrawn, a delivery catheter 150 may then be advanced through the lumen of the tunnel catheter 148. As shown in FIG. 1G, a distal portion 152 of delivery catheter 150 is advanced toward an opening 154 in distal portion 156 of tunnel catheter 148. In some embodiments, the delivery catheter 150 may be extended through the opening 154 of the tunnel catheter 148. As shown in FIG. 1H, an anchor 158, which is attached to a guide element (shown in FIG. 11 as a tether 158), may then be deployed from delivery catheter 150. The anchor 158 may be deployed from the delivery catheter 150 in any suitable fashion, including but not limited to a push-pull wire, using a plunger, or other suitable actuation technique. Similarly, anchor 158 may be attached to tether 158 by any suitable attachment method. For example, one or more knots, welded regions, and/or adhesives may be used. Alternate embodiments for anchor deployment and anchor attachments are described in U.S. patent application Ser. Nos. 11/583,627, and 61/083,109, which are hereby incorporated by reference in its entirety.

The anchors for use with the methods and devices described here may be any suitable anchor. The anchors may be made of any suitable material, may be any suitable size, and may be of any suitable shape. The anchors may be made of one material or more than one material. Examples of anchor materials include super-elastic or shape memory materials, such as nickel-titanium alloys and spring stainless steel. Examples of anchor shapes include T-tags, rivets, staples, hooks (e.g., C-shaped or semicircular hooks, curved hooks of other shapes, straight hooks, barbed hooks), multiple looped anchors, and clips. The anchors may be configured to self-expand and self-secure into tissue, but need not be configured in such a fashion. Additionally, while the delivery and deployment of multiple anchors of the same shape over a single guide element have been described, in some variations, a single guide element can be used to deliver and deploy multiple anchors having different shapes. Similarly, in certain variations, a single guide element can be used in the delivery and deployment of multiple anchors having different sizes. Illustrative examples of suitable anchors are described in more detail, for example, in U.S. patent application Ser. No. 11/202,474, which is hereby incorporated by reference in its entirety.

Figure 1J:
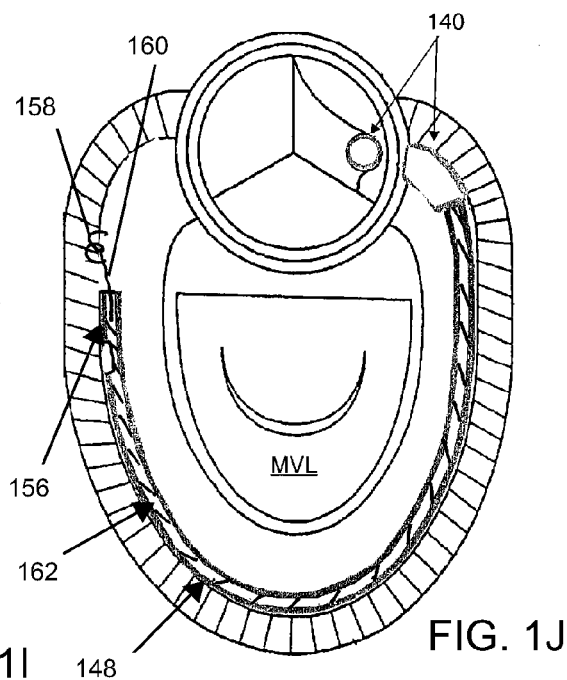
Figure 1K:
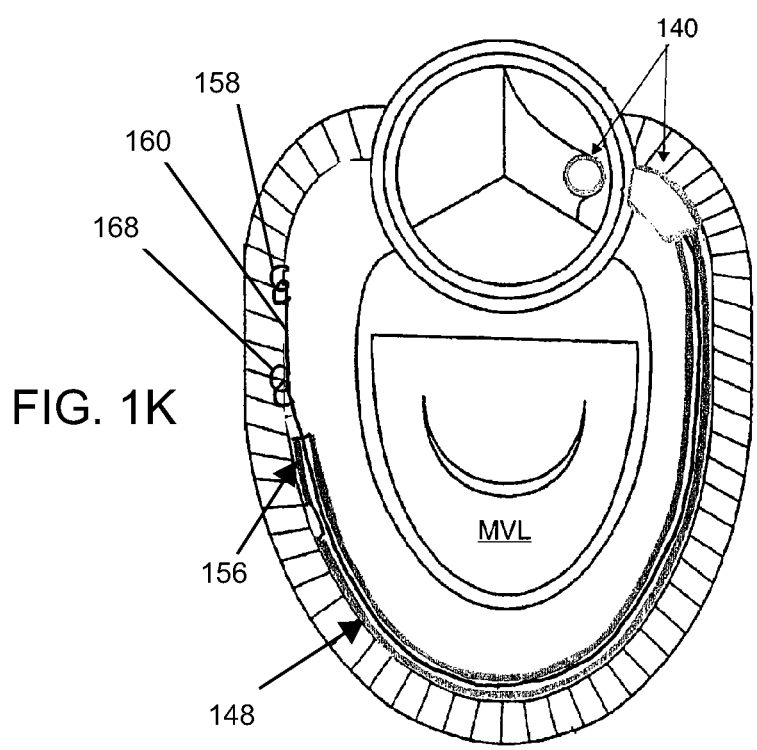

The anchor 158, shown in FIG. 1H, may be configured to self-expand as it exits delivery catheter 150 and to self-secure into a region of the mitral valve annulus, but may also be used to in other regions of the heart. It should be understood that the one or more anchors may be deployed into the annulus directly, while other anchors may be secured to other tissue in the vicinity of the subannular groove region. For example, one or more anchors may be secured to the tissue below the annulus. After anchor 158 has been deployed, delivery catheter 150 may be proximally withdrawn. FIG. 11 shows anchor 158, attached to tether 160 and secured to the mitral valve annulus AN. As shown in FIG. 1J, tunnel catheter 148 may then be moved to a different location or position in the subannular groove region or the heart, and a second delivery catheter 162 is advanced through the lumen of tunnel catheter 148, over tether 160, as shown in FIG. 1K.

Before delivery catheter 162 is advanced through tunnel catheter 148, the tether 160 may be threaded into delivery catheter 162, and slidably engaged with a second anchor 164.

Any of a number of different methods can be used to thread a guide element, such as a tether, into a delivery catheter, and to engage the guide element with an anchor. Other methods are disclosed in U.S. patent application Ser. No. 11/202,474, which was previously incorporated by reference, and threading devices are described, for example, in U.S. patent application Ser. No. 11/232,190, which is hereby incorporated by reference in its entirety. With reference now to FIG. 1K, after delivery catheter 162 has been advanced through tunnel catheter 148, and is used to deploy anchor 164 before being withdrawn from the tunnel catheter 148.

Tunnel catheter 148 may be formed of any of a number of different materials. Examples of suitable materials include polymers, such as polyether-block co-polyamide polymers, copolyester elastomers, thermoset polymers, polyolefins (e.g., polypropylene or polyethylene, including high-density polyethylene and low-density polyethylene), polytetrafluoroethylene, ethylene vinyl acetate, polyamides, polyimides, polyurethanes, polyvinyl chloride (PVC, fluoropolymers (e.g., fluorinated ethylene propylene, perfluoroalkoxy (PFA) polymer, polyvinylidenefluoride, etc.), polyetheretherketones (PEEKs), and silicones. Examples of polyamides that may be included in tunnel catheter (410) include Nylon 6 (e.g., Zytel® HTN high performance polyamides from DuPont™), Nylon 11 (e.g., Rilsan® B polyamides from Arkema Inc.), and Nylon 12 (e.g., Grilamid® polyamides from EMS-Grivory, Rilsan® A polyamides from Arkema Inc., and Vestamid® polyamides from Degussa Corp.). In some variations, tunnel catheter 148 may be formed of multiple polymers. For example, tunnel catheter 148 may be formed of a blend of different polymers, such as a blend of high-density polyethylene and low-density polyethylene. While the wall of tunnel catheter 148 is formed of a single layer, some variations of tunnel catheters may include walls having multiple layers (e.g., two layers, three layers). Furthermore, some variations of tunnel catheters may include at least two sections that are formed of different materials and/or that include different numbers of layers. Additionally, certain variations of tunnel catheters may include multiple (e.g., two, three) lumens. The lumens may, for example, be lined and/or reinforced (e.g., with braiding).

Figure 24A:
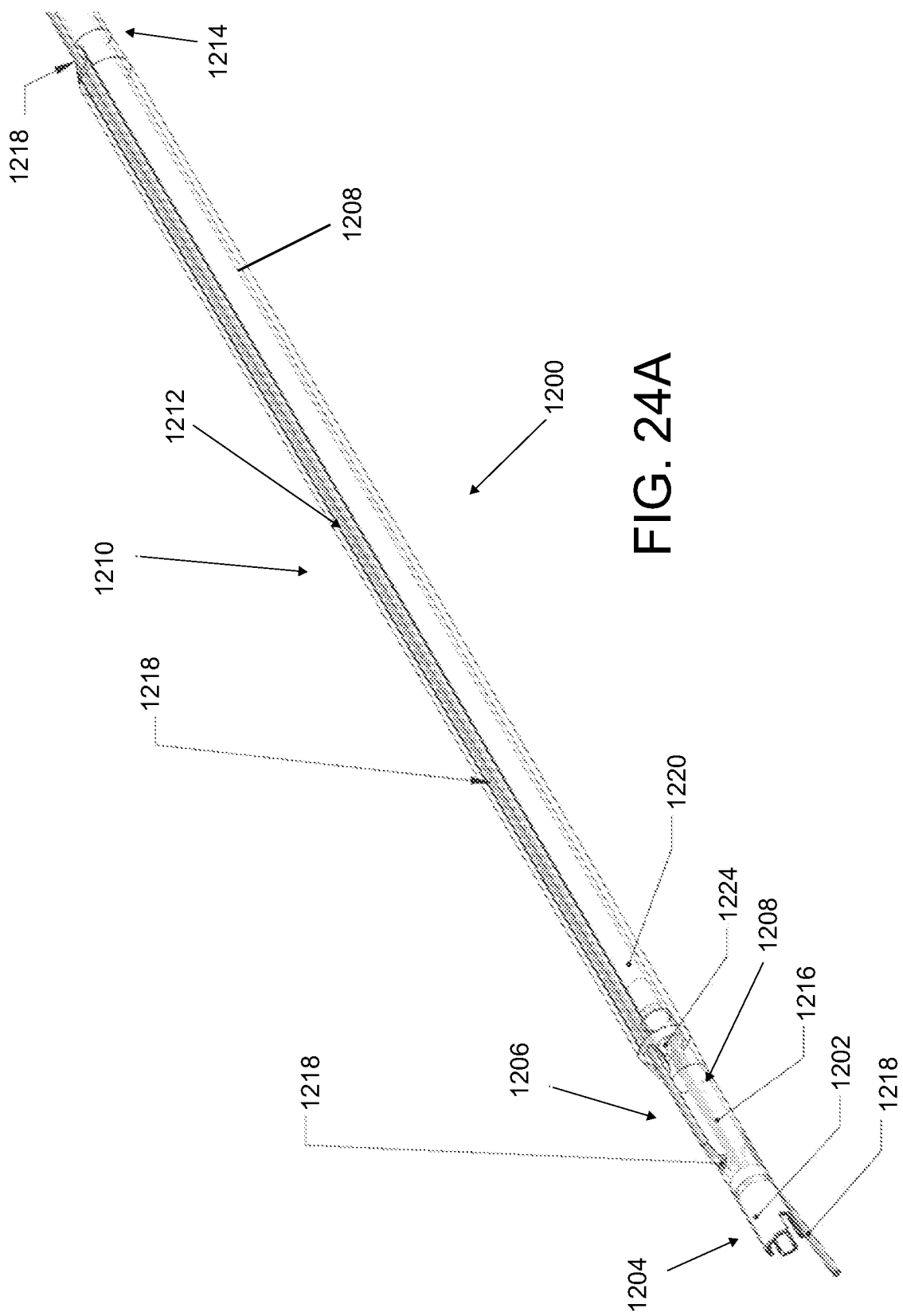
FIG. 24A is a perspective view of a delivery catheter.

FIGS. 24A to 24D show various detailed views of one embodiment of a delivery catheter 1200 that can be used to deliver one or more anchors to a target site. As shown in FIG. 24A, the delivery catheter 1200 has a distal region 1204 including a tip 1202, an anchor-holding region 1206 including a primary lumen 1208, an intermediate region 1210, a secondary lumen 1212, and a proximal region 1214 including primary lumen 1208. An anchor 1216 is disposed within primary lumen 1208, in the anchor-holding region 1206. While only one anchor is shown in the anchor-holding region, some variations of delivery catheters may include an anchor-holding region that is adapted to hold multiple anchors. Similarly, while the variation shown in FIGS. 24A to 24D depict anchors adapted to be deployed from the distal end of the delivery catheter, it should be understood that the anchors may be deployed from any suitable region of the delivery catheter, as desirable. For example, if desirable, the anchor may be delivered out of a side port or hole on the delivery catheter.

As shown in FIGS. 24A to 24D, a tether 1218 is threaded into a slot 1219 of tip 1202 (shown in FIGS. 24C and 24D), and through an eyelet 1226 of anchor 1216. After extending through the eyelet, the tether may exit the primary lumen 1208, and extend along an exterior surface 1221 of delivery catheter 1200 for the remainder of the length of the anchor-holding region, as shown in FIG. 24C. The tether then enters secondary lumen 1212, and extends through the length of the secondary lumen, exiting the secondary lumen at an end of distal region 1214. An actuator 1220 may be slidably disposed within primary lumen 1208, and can be used to deploy anchor 1216. The actuator is in the form of a pushable generally tubular member, although other forms of actuators may be used. For example, in some variations, a solid rod may be used as an actuator. Other embodiments of the delivery catheter are described in U.S. patent application Ser. No. 11/202,474, which was previously incorporated by reference.

It should also be understood that while some embodiments of the invention utilize multiple anchors being delivered via multiple delivery catheters, other methods of delivering the anchors may be used. For example, in some instances, it may be desirable to deliver multiple anchors from a single delivery catheter, as described in more detail below and in U.S. patent application Ser. No. 11/201,949, which is hereby incorporated by reference in its entirety. Similarly, it may be desirable to combine multiple anchor delivery and deployment via a single delivery catheter with single anchor delivery and deployment via a single delivery catheter.

Figure 3:
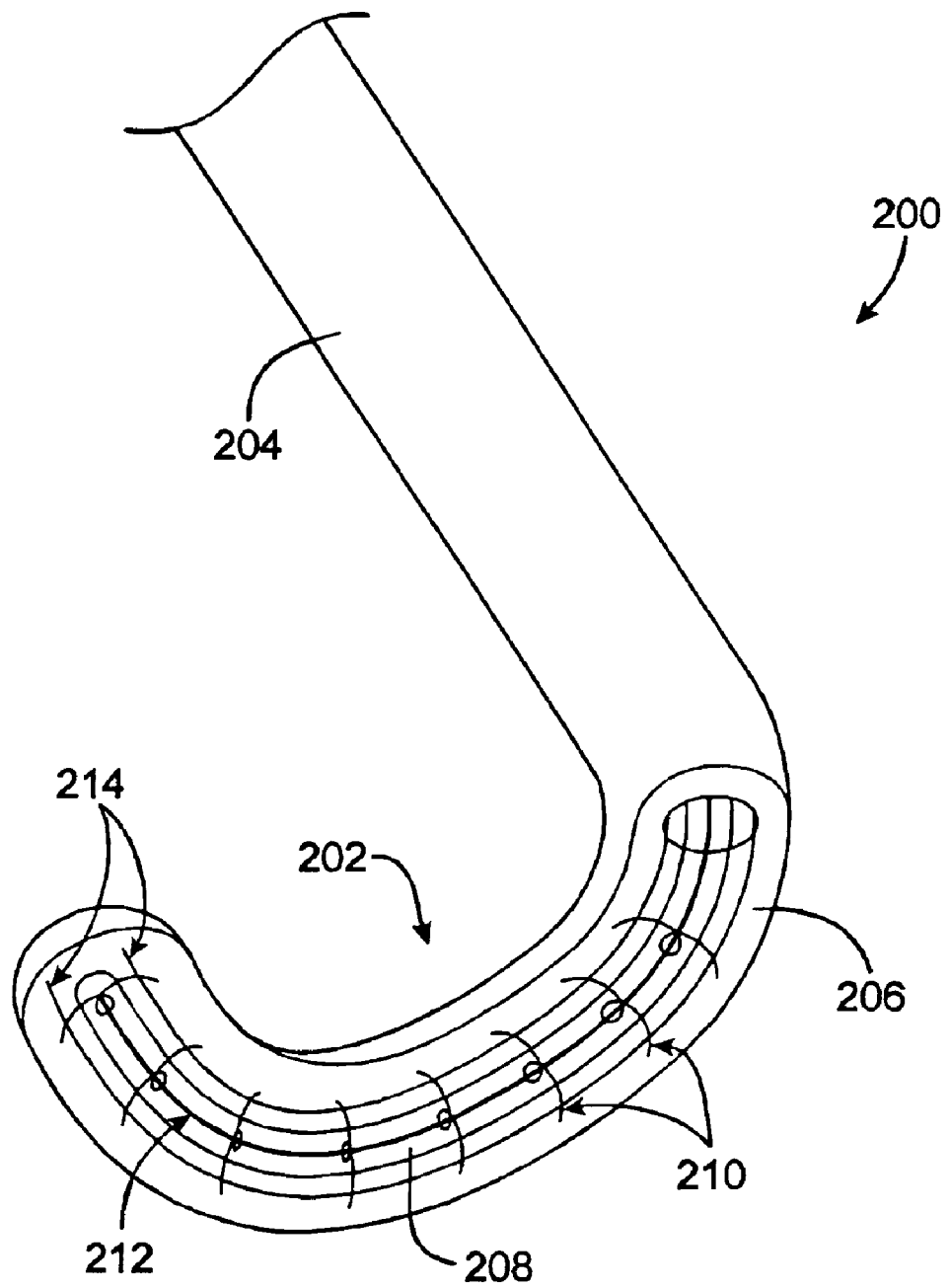
FIG. 3 is a perspective view of a distal portion of an anchor delivery device.

With reference now to FIG. 3, one embodiment comprises an anchor delivery device 200, which suitably includes an elongate shaft 204 having a distal portion 202 configured to deliver a plurality of anchors 210, coupled with a tether 212, and configured for attachment to annular tissue. The tethered anchors 210 are housed within a housing 206 of the distal portion 202, along with one or more anchor retaining mandrels 214 and an expandable member 208. Many variations may be made to include one or more of these features, and various parts may be added or eliminated. Some of these variations are described further below, but no specific variation(s) should be construed as limiting.

Housing 206 may be flexible or rigid in some variations. In some embodiments, for example, flexible housing 206 may comprise multiple segments configured such that housing 206 is deformable by tensioning a tensioning member coupled to the segments. In some embodiments, housing 206 is formed from an elastic material having a geometry selected to engage and optionally shape or constrict the annular tissue. For example, the rings may be formed from spring stainless steel, super-elastic shape memory alloys such as nickel-titanium alloys (e.g., Nitinol), or the like. In other embodiments, the housing 206 could be formed from an inflatable or other structure that can be selectively rigidified in situ, such as a gooseneck or lockable element shaft, any of the rigidifying structures described above, or any other rigidifying structure.

"Anchors," for the purposes of this application, are defined to include any of a variety of fasteners. Thus, anchors 210 may comprise C-shaped or semicircular hooks, curved hooks of other shapes, straight hooks, barbed hooks, clips of any kind, T-tags, or any other suitable fastener(s). In one embodiment, as described above, anchors may comprise two tips that curve in opposite directions upon deployment, forming two intersecting semi-circles, circles, ovals, helices or the like. In some embodiments, anchors 210 are self-deforming. By "self-deforming" it is meant that anchors 210 are biased to change from a first undeployed shape to a second deployed shape upon release of anchors 210 from restraint in housing 206. Such self-deforming anchors 210 may change shape as they are released from housing 206 and enter annular tissue, and secure themselves to the tissue. Self-deforming anchors 210 may be made of any suitable material such as spring stainless steel, or a super-elastic or shape-memory material like nickel-titanium alloy (e.g., Nitinol).

In other embodiments, the anchors 210 may be made of a non-shape-memory material and may be loaded into housing 206 in such a way that they change shape upon release. For example, anchors 210 that are not self-deforming may be secured to tissue via crimping, firing or other application of mechanical force to facilitate tissue penetration and/or securement. Even self-securing anchors may be crimped in some embodiments of the invention, to provide enhanced attachment to tissue. In some embodiments, anchors 210 may comprise one or more bioactive agents. In another embodiment, anchors 210 may comprise electrode components. Such electrodes, for example, may sense various parameters including but not limited to impedance, temperature and electrical signals. In other embodiments, such electrodes may be used to supply energy to tissue at ablation or sub-ablation amounts. In still other embodiments, the anchors may be incorporated with an implantable pacing lead or an implanted sensor of a congestive heart failure monitor. Examples of a congestive heart failure monitor include the HeartPOD™ Implantable Heart Failure Therapy System by Savacor, Inc. (Los Angeles, Calif.) and the OptiVol® feature of the InSync Sentry™ cardiac resynchronization therapy-defibrillator by Medtronic, Inc. (Minneapolis, Minn.). These systems are described in greater detail in U.S. Pat. Nos. 6,970,742 and 6,931,272, of which those portions relating to suitable devices and methods are herein incorporated by reference. Delivery of the anchors may be accomplished by any suitable device and technique, such as by simply releasing the anchors by hydraulic balloon delivery as discussed further below. Any number, size and shape of the anchors 210 may be included in housing 206.

In another embodiment, the anchors 210 may generally C-shaped or semicircular in their undeployed form, with the ends of the "C" being sufficiently sharpened to penetrate tissue. Between the ends of the C-shaped anchor 210, an eyelet may be formed for allowing slidable passage of the tether 212. To maintain the anchors 210 in their C-shaped, undeployed state, anchors 210 may be retained within housing 206 by two mandrels 214, one mandrel 214 retaining each of the two arms of the C-shape of each anchor 210. Mandrels 214 may be retractable within elongate catheter body 204 to release anchors 210 and allow them to change from their undeployed C-shape to a deployed shape. The deployed shape, for example, may approximate a partial or complete circle, or a circle with overlapping ends, the latter appearing similar to a key ring. Such anchors are described further below, but generally may be advantageous in their ability to secure themselves to annular tissue by changing from their undeployed to their deployed shape. In some variations, anchors 210 may also be configured to lie flush with a tissue surface after being deployed. By "flush" it is meant that no significant amount of an anchor protrudes from the surface, although some small portion may protrude.

The retaining mandrels 214 may have any suitable cross-sectional shape, cross-sectional area, length and be made of any suitable material, such as stainless steel, titanium, nickel-titanium alloys (e.g., Nitinol), or the like. Some embodiments may not include a mandrel, or may have one mandrel, two mandrels, or more than two mandrels.

In some embodiments, the anchors 210 may be released from mandrels 214 to contact and secure themselves to annular tissue without any further force applied by the delivery device 200. Some embodiments, however, may also include one or more expandable members 208, which may be expanded to help drive anchors 210 into tissue. Expandable member(s) 208 may have any suitable size and configuration and may be made of any suitable material(s). Any of a variety of mechanical and hydraulic expandable members known in the art may be included in housing 206.

Figure 4:
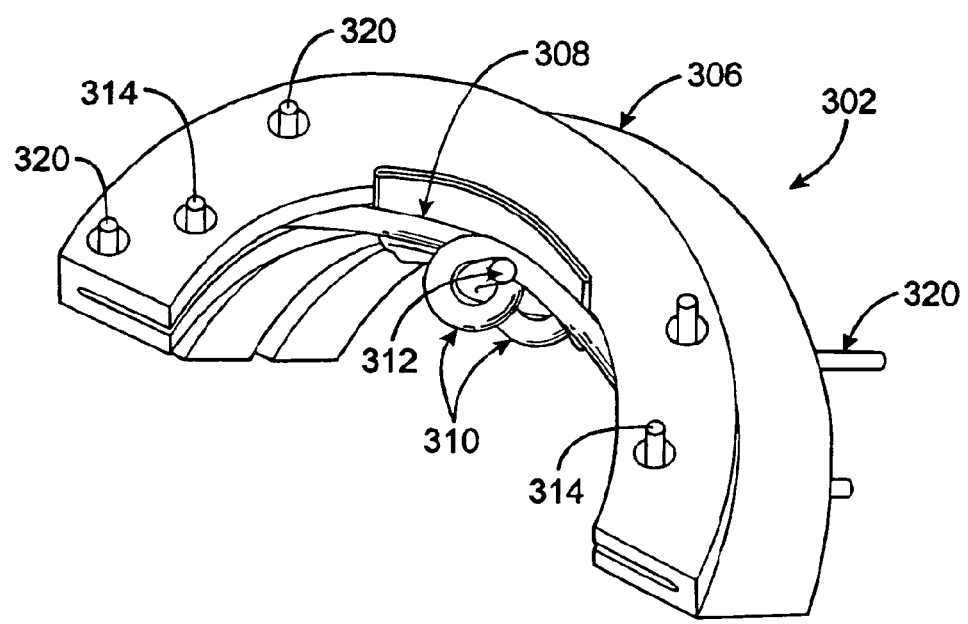
FIG. 4 is a perspective view of a segment of a distal portion of an anchor delivery device, with the anchors in an undeployed shape and position.
Figure 5:
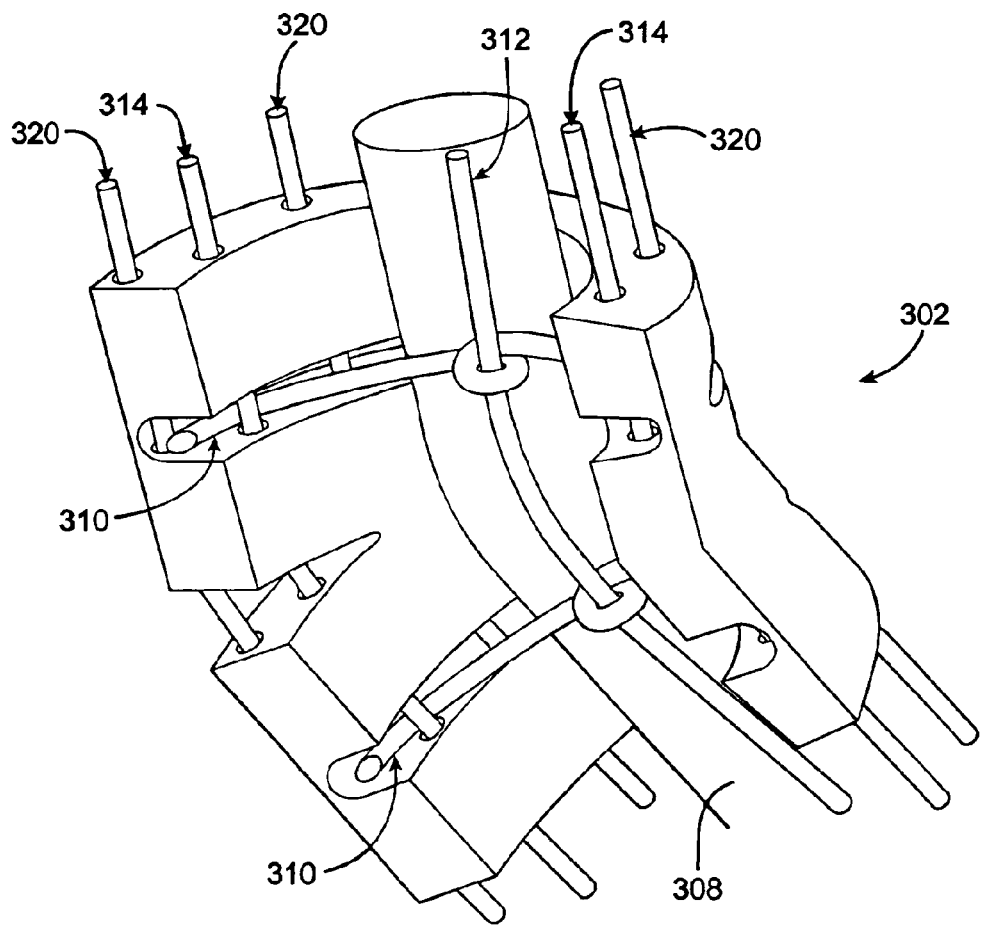
FIG. 5 is a different perspective view of the segment of the device shown in FIG. 4.

Referring now to FIGS. 4 and 5, a segment of a distal portion 302 of an anchor delivery device suitably includes a housing 306, multiple tensioning members 320 for applying tension to housing 306 to change its shape, two anchor retaining mandrels 314 slidably disposed in housing 306, multiple anchors 310 slidably coupled with a tether 312, and an expandable member 308 disposed between anchors 310 and housing 306. As can be seen in FIGS. 4 and 5, housing 306 may include multiple segments to allow the overall shape of housing 306 to be changed by applying tension to tensioning members 320. As also is evident from the drawings, "C-shaped" anchors 310 may actually have an almost straight configuration when retained by mandrels 314 in housing 306. Thus, for the purposes of this application, "C-shaped" or "semicircular" refers to a very broad range of shapes including a portion of a circle, a slightly curved line, a slightly curved line with an eyelet at one point along the line, and the like.

Figure 6:
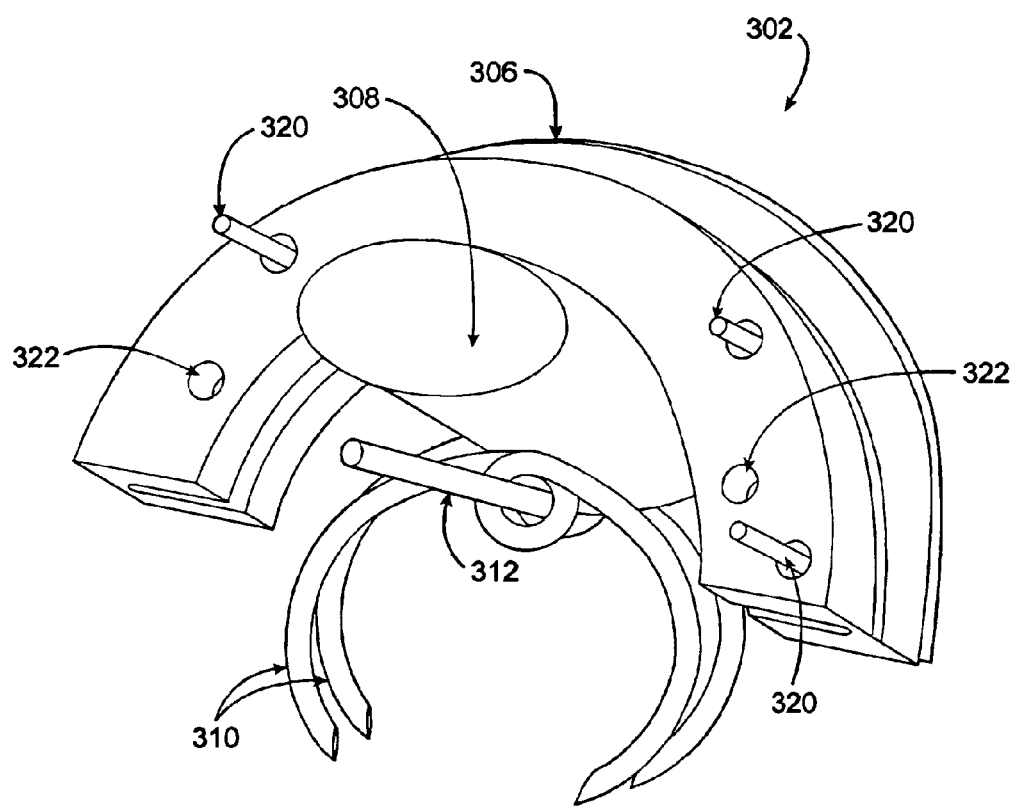
FIG. 6 is a perspective view of a segment of a distal portion of an anchor delivery device, with anchors in a deployed shape and position.

With reference now to FIG. 6, the same segment of distal portion 302 is shown, but mandrels 314 have been withdrawn from two mandrel apertures 322, to release anchors 310 from housing 306. Additionally, expandable member 308 has been expanded to drive anchors out of housing 306. Anchors 310, having been released from mandrels 314, have begun to change from their undeployed, retained shape to their deployed, released shape.

Figure 7A:
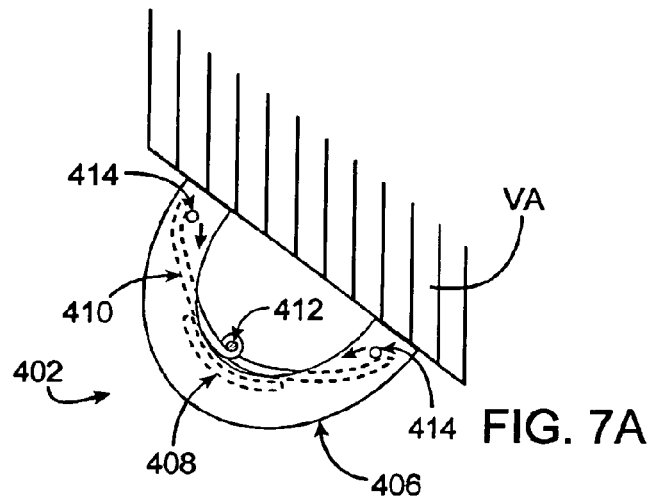
FIGS. 7A through 7E are cross-sectional views of an anchor delivery device, illustrating a method for delivering anchors to valve annular tissue.

Referring now to FIGS. 7A to 7E, a cross-section of a distal portion 402 of an anchor delivery device is shown in various stages of delivering an anchor to annular tissue. In FIG. 7A, distal portion 402 is positioned against the annular tissue, an anchor 410 is retained by two mandrels 414, a tether 412 is slidably disposed through an eyelet on anchor 410, and an expandable member 408 is coupled with housing 406 in a position to drive anchor 410 out of housing 406. When retained by mandrels 414, anchor 410 may be in its undeployed shape. As discussed above, mandrels 414 may be slidably retracted, as designated by the solid-tipped arrows in FIG. 7A, to release anchor 410. In some embodiments, anchors 410 may be released one at a time, such as by retracting mandrels 414 slowly, may be released in groups, or may all be released simultaneously, such as by rapid retraction of mandrels 414.

Figure 7B:
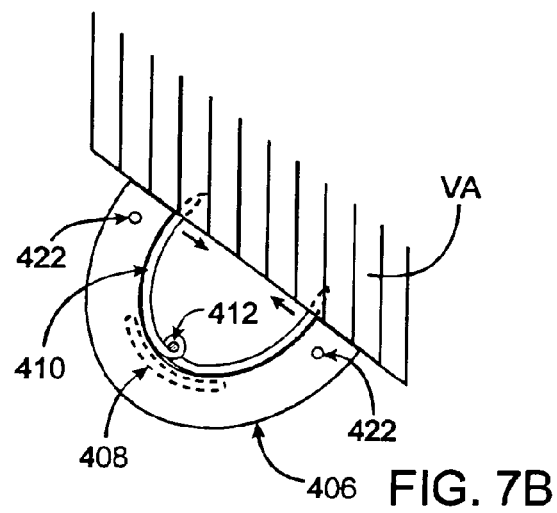
Figure 7C:
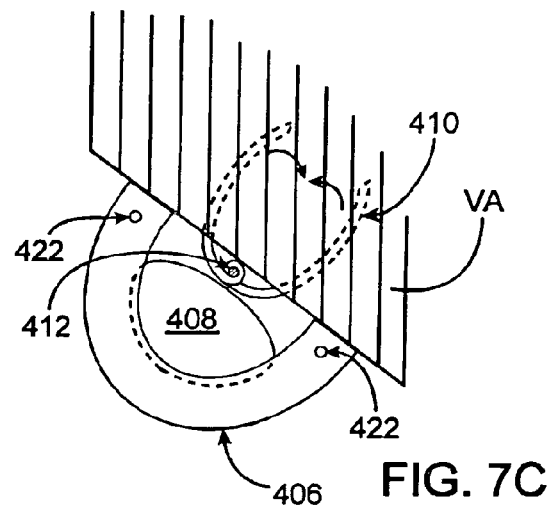
Figure 7D:
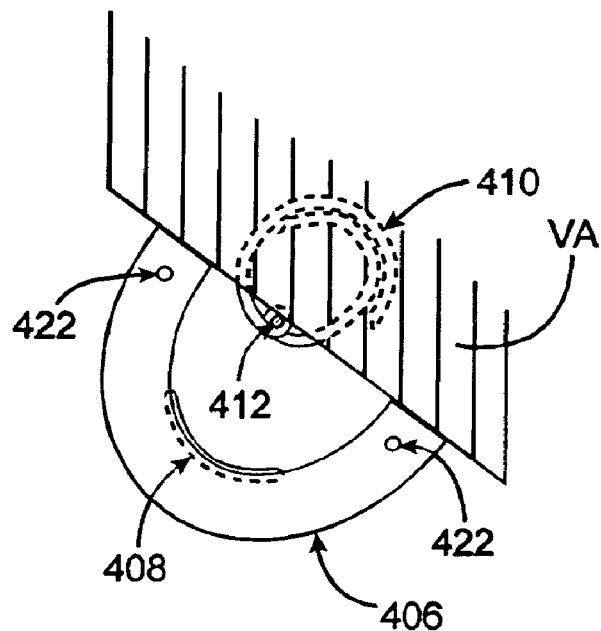
Figure 7E:
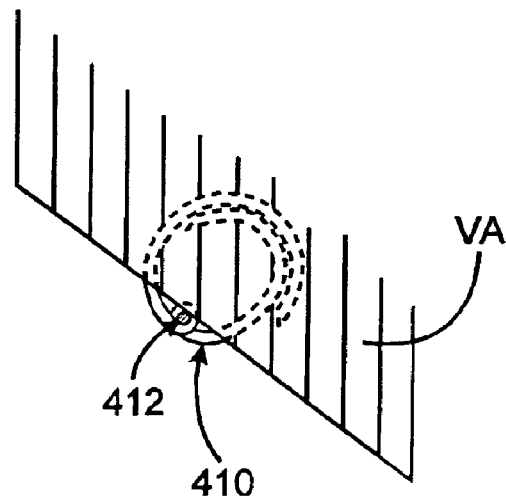

In the example depicted in FIG. 7B, anchor 410 has begun to change from its undeployed shape to its deployed shape (as demonstrated by the hollow-tipped arrows) and has also begun to penetrate the annular tissue. Empty mandrel apertures 422 demonstrate that mandrels 414 have been retracted at least far enough to release anchor 410. In FIG. 7B, expandable member 408 has been expanded to drive anchor 410 partially out of housing 406 and further into the annular tissue VA. Anchor 410 also continues to move from its undeployed towards its deployed shape, as shown by the hollow-tipped arrows. In FIG. 7D, anchor 410 has reached its deployed shape, which is roughly a completed circle with overlapping ends or a "key ring" shape. In FIG. 7E, delivery device 402 has been removed, leaving a tethered anchor in place in the valve annulus. Of course, there will typically be a plurality of tethered anchors secured to the annular tissue. Tether 412 may then be cinched to apply force to anchors 410 and cinch and tighten the valve annulus.

Figure 8A:
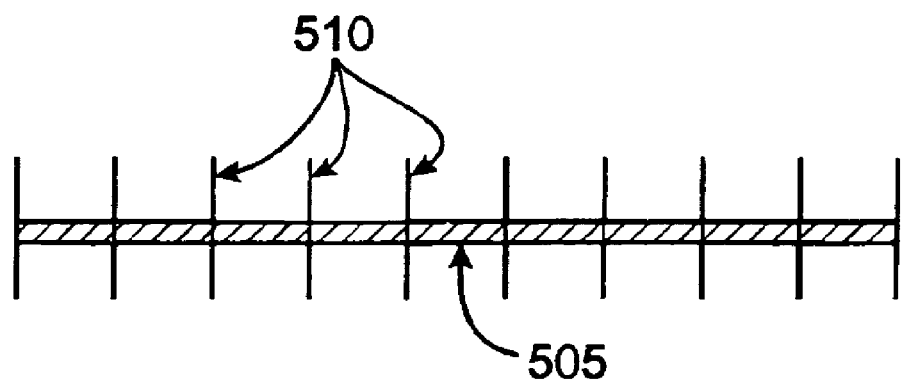
FIGS. 8A and 8B are top-views of a plurality of anchors coupled to a self-deforming coupling member, with the coupling member shown in an undeployed shape and a deployed shape, respectively.
Figure 8B:
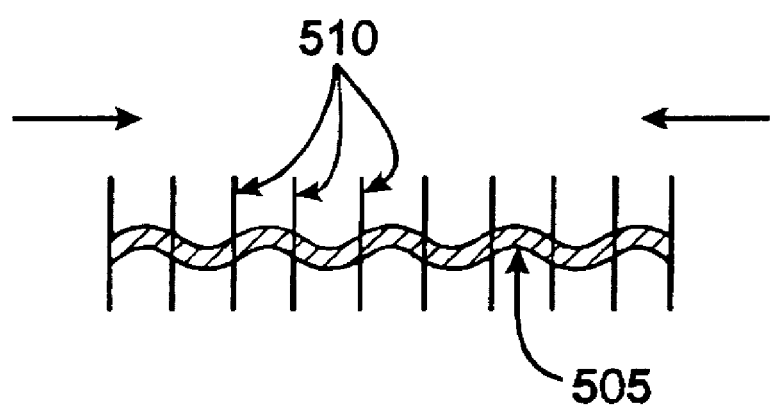

With reference now to FIGS. 8A and 8B, a diagrammatic representation of another embodiment comprising coupled anchors is shown. Here, anchors 510 are coupled to a self-deforming or deformable coupling member or backbone 505. In some examples, this backbone 505 may be another embodiment of a tether. The backbone 505 may be fabricated, for example, from nickel-titanium alloys (e.g., Nitinol), spring stainless steel, or the like, and may have any suitable size or configuration. In one embodiment, as in FIG. 8A, backbone 505 is shaped as a generally straight line when held in an undeployed state, such as when restrained within a housing of an anchor deliver device. When released from the delivery device, backbone 505 may change to a deployed shape having multiple bends, as shown in FIG. 8B. By bending, backbone 505 shortens the longitudinal distance between anchors, as demonstrated by the solid-tipped arrows in FIG. 8B. This shortening process may act to reshape the annular tissue into which anchors 510 have been secured. Thus, anchors 510 coupled to backbone 505 may be used to reshape annular tissue without using a separate tether or applying tethering force. In other embodiments, an elastic tether may be used as the backbone 505. In still other embodiments, backbone may also be coupled with a termination member to further cinch the annular tissue. In such an embodiment, the backbone 505 is adapted to be at least partially conformable or cinchable, such that when force is applied to anchors 510 and backbone 505 via a tether, backbone 505 bends further to allow further cinching of the annular tissue.

Figure 9A:
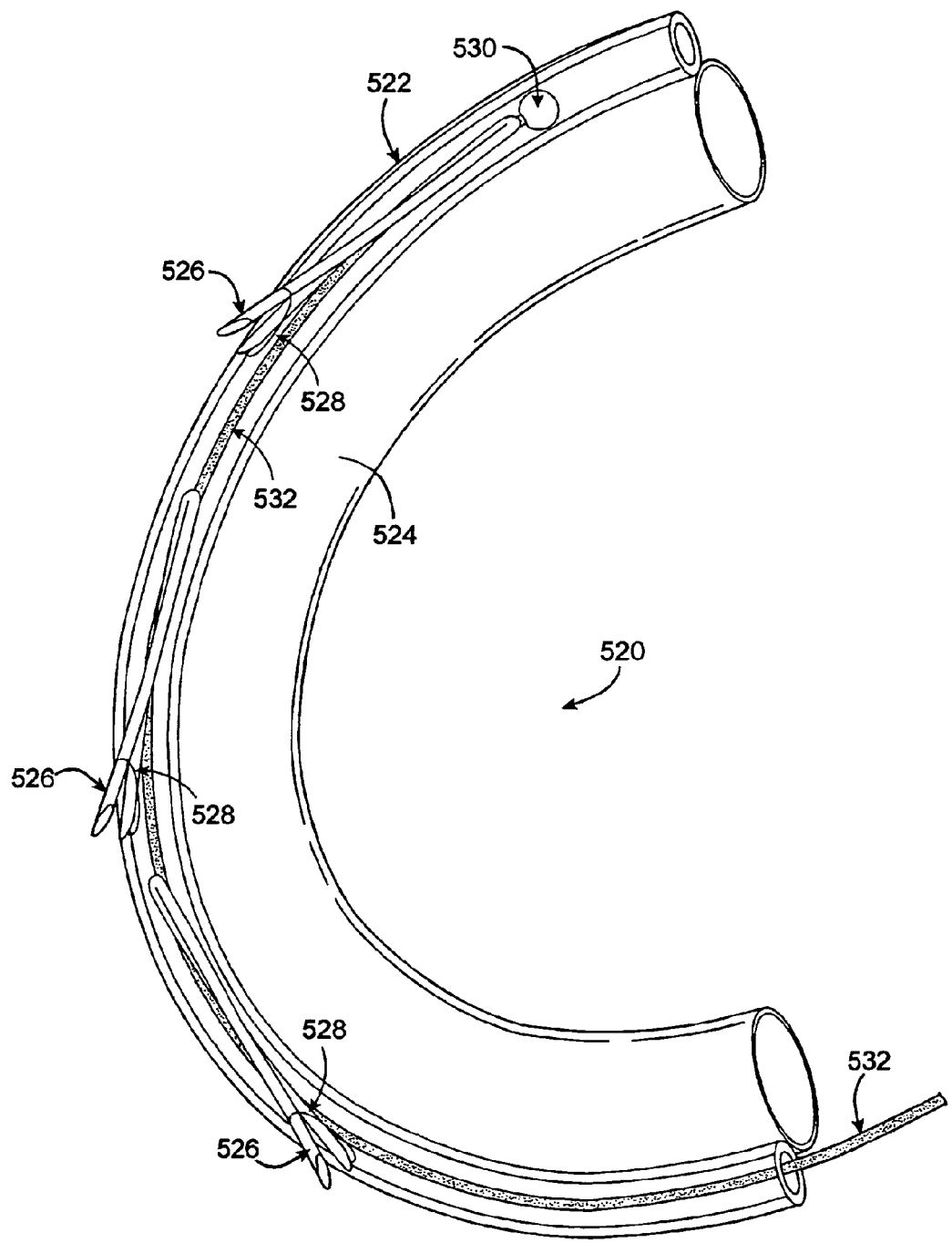
FIGS. 9A through 9C are various perspective views of a distal portion of a flexible anchor delivery device.
Figure 9B:
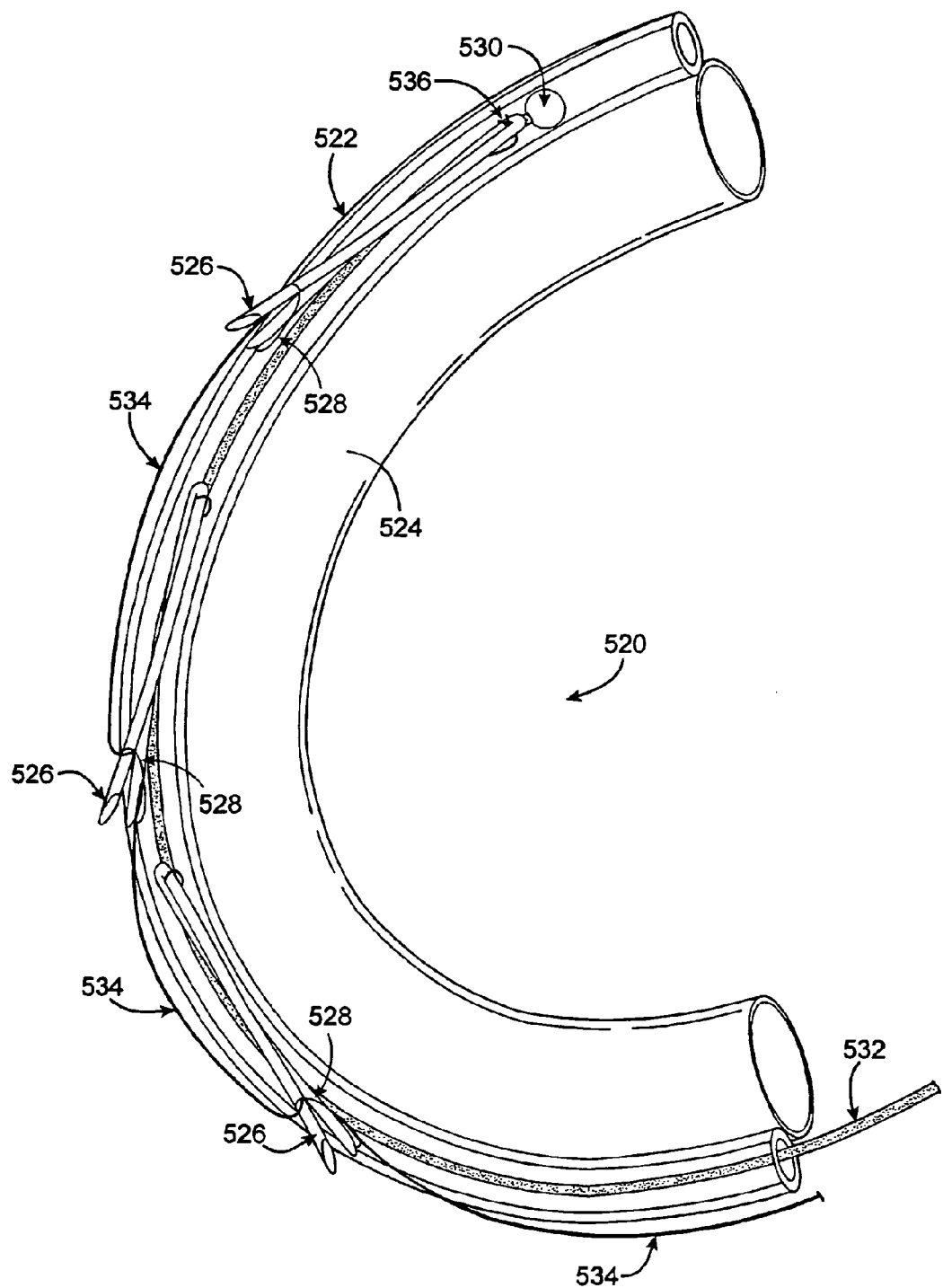
Figure 9C:
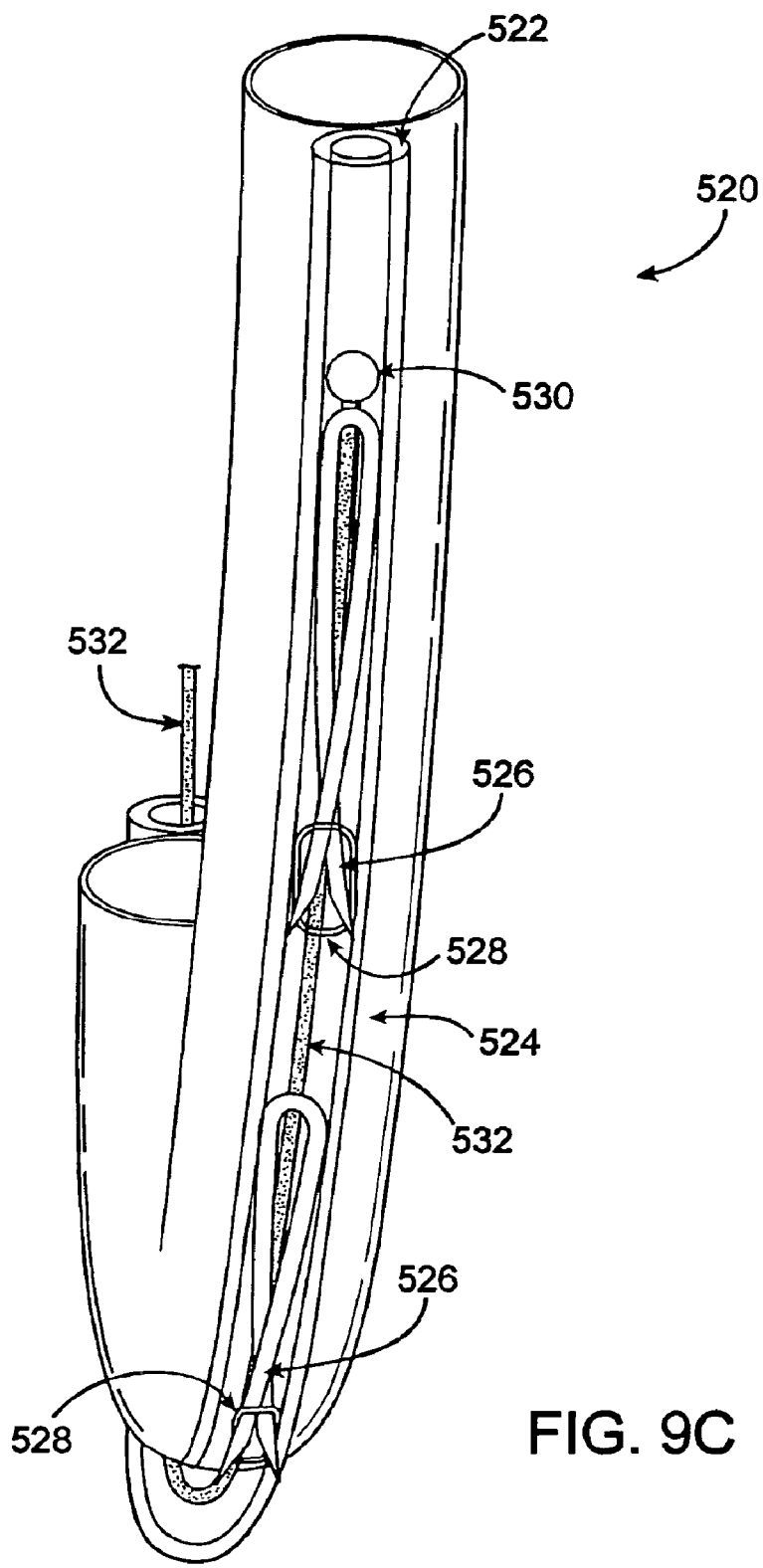

In another embodiment, shown in FIGS. 9A to 9C, a flexible distal portion of an anchor delivery device 520 includes a housing 522 coupled with an expandable member 524. Housing 522 may be configured to house multiple coupled anchors 526 and an anchor contacting member 530 coupled with a pull cord 532. Housing 522 may also include multiple apertures 528 for allowing egress of anchors 526. For clarity, delivery device 520 is shown without a tether in FIGS. 9A and 9C, but FIG. 9B shows that a tether 534 may extend through an eyelet, loop or other portion of each anchor 526, and may exit each aperture 528 to allow for release of the plurality of anchors 526. The various features of this variation are described further below.

In the specific embodiment in FIGS. 9A to 9C, anchors 526 are relatively straight and lie relatively in parallel with the long axis of delivery device 522. Anchor contacting member 530, which may comprise a device such as a ball, plate, hook, knot, plunger, piston, or the like, may generally have an outer diameter that is nearly equal to or slightly less than the inner diameter of housing 522. Contacting member 530 is disposed within the housing, distal to a distal-most anchor 526, and may be retracted relative to housing 522 by pulling pull cord 532. When retracted, anchor contacting member 530 contacts and applies force to a distal-most anchor 526 to cause release of that anchor 526 from housing 522 via one of the apertures 528. Contacting member 530 is then pulled farther proximally to contact and apply force to the next anchor 526 to deploy that anchor 526, and so on.

Retracting contacting member 530 to push anchors 526 out of apertures 528 may help cause anchors 526 to secure themselves to the tissue adjacent the apertures 528. Using anchors 526 that are relatively straighter/flatter in configuration when undeployed may allow anchors 526 with relatively large deployed sizes to be disposed in (and delivered from) a relatively small housing 522. In one embodiment, for example, anchors 526 that deploy into a shape approximating two intersecting semi-circles, circles, ovals, helices, or the like, and that have a radius of one of the semi-circles of about 3 mm may be disposed within a housing 522 having a diameter of about 5 French (1.67 mm) and more preferably about 4 French (1.35 mm) or even smaller. Such anchors 526 may measure about 6 mm or more in their widest dimension. In some embodiments, housing 522 may have a diametrical dimension ("d") and anchor 526 may have a diametrical dimension ("D") in the deployed state, and the ratio of D to d may be at least about 3.5. In other embodiments, the ratio of D to d may be at least about 4.4, and more preferably at least about 7, and even more preferably at least about 8.8. These are only examples, however, and other larger or smaller anchors 526 may be disposed within a larger or smaller housing 522. The dimensions of an anchor may vary depending on the particular usage. For example, anchors used for ventriculoplasty may permit the use of larger anchors than those used for annuloplasty due to fewer space constraints in the main compartment of the ventricles than in the subvalvular spaces. Furthermore, any convenient number of anchors 526 may be disposed within housing 522. In one variation, for example, housing 522 may hold about 1 to about 20 anchors 526, and more preferably about 3 to about 10 anchors 526. Other variations may hold more anchors 526.

Anchor contacting member 530 and pull cord 532 may have any suitable configuration and may be manufactured from any material or combination of materials. In alternative embodiments of the invention, contacting member 530 may be pushed by a pusher member to contact and deploy anchors 526. Alternatively, any of the anchor deployment devices and methods previously described may be used.

Tether 534, as shown in FIG. 9B, may comprise any of the tethers or tether-like devices described above, or any other suitable device. Furthermore, in some variations, multiple tethers may be provided. In such variation and each tether may or may not be coupled to every anchor, and some or all of the anchors may be coupled to more than one tether. Tether 534 may be generally attached to a distal-most anchor 526 at an attachment point 536. The attachment itself may be achieved via a knot, weld, adhesive, or by any other suitable attachment mechanism. Tether 234 then extends through an eyelet, loop or other similar configuration on each of the anchors 526 so as to be slidably coupled with the anchors 526. In the particular embodiment shown, tether 534 exits each aperture 528, then enters the next-most-proximal aperture, passes slidably through a loop on an anchor 526, and exits the same aperture 528. By entering and exiting each aperture 528, tether 534 allows the plurality of anchors 526 to be deployed into tissue and cinched. Alternate embodiments of housing 522, anchors 526 and tether 534 may also be used. For example, housing 522 may include a longitudinal slit through which tether 534 may pass, thus allowing tether 534 to reside wholly within housing before deployment.

Expandable member 524 is an optional feature of anchor delivery device 520, and thus may be included in some embodiments and not in others. In some embodiments, expandable member 524 will be coupled with a surface of housing 522, will have a larger radius than housing 522, and will be configured such that when it is expanded as housing 522 nears or contacts the valve annulus, expandable member 524 will push or press housing 522 into enhanced contact with the annulus. For example, expandable member 524 may be configured to expand within a space near the corner formed by a left ventricular wall and a mitral valve leaflet.

Figure 10A:
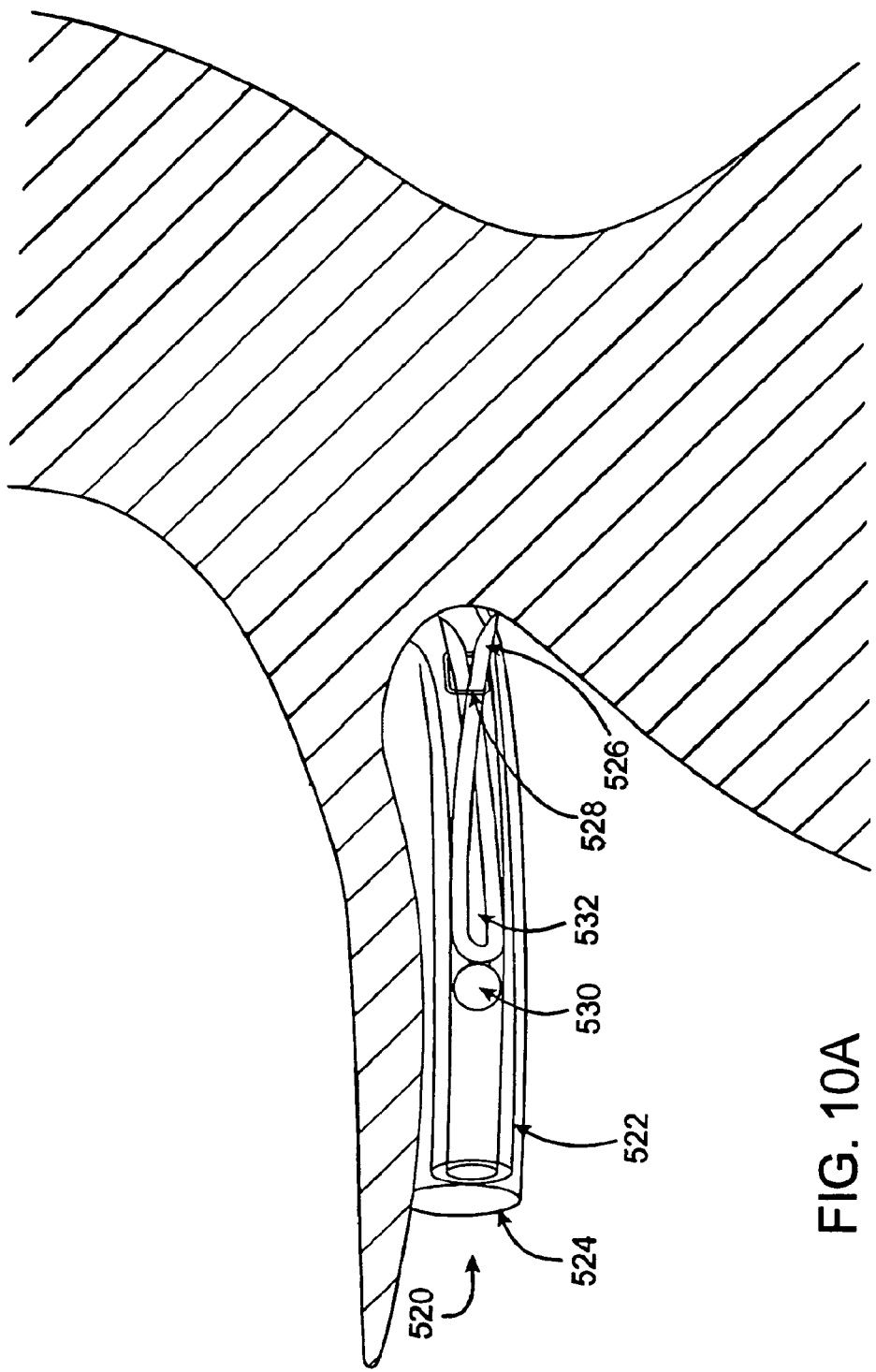

With reference now to FIGS. 10A to 10F, one embodiment of the invention comprises a method for applying a plurality of tethered anchors 526 to the annular tissue of a heart. As shown in FIG. 10A, an anchor delivery device 520 is first contacted with the valve annulus VA or annular tissue such that openings 528 are oriented to deploy anchors 526 into the tissue. Such orientation may be achieved by any suitable technique. In one embodiment, for example, a housing 522 having an elliptical cross-sectional shape may be used to orient openings 528. Contact between housing 522 and the annular tissue may be enhanced by expanding expandable member 524 to wedge housing 522 within the deepest portion of the subannular groove region.

Generally, delivery device 520 may be advanced into any suitable location for treating any valve by any suitable advancing or device placement method. Many catheter-based, minimally invasive devices and methods for performing intravascular procedures, for example, are well known, and any such devices and methods, as well as any other devices or method later developed, may be used to advance or position delivery device 520 in a desired location. For example, in one embodiment a steerable guide catheter is first advanced in a retrograde fashion through an aorta, typically via access from a femoral artery. The steerable catheter is passed into the left ventricle of the heart and thus into the space formed by the mitral valve leaflets, the left ventricular wall and chordae tendineae of the left ventricle. Once in this space, the steerable catheter is advanced along a portion (or all) of the circumference of the mitral valve. A sheath is advanced over the steerable catheter within the space below the valve leaflets, and the steerable catheter is removed through the sheath. Anchor delivery device 520 may then be advanced through the sheath to a desired position within the space, and the sheath may be removed. In some cases, an expandable member coupled to delivery device 520 may be expanded to wedge or otherwise move delivery device 520 into the corner formed by the left ventricular wall and the valve leaflets to enhance its contact with the valve annulus. This is but one exemplary method for advancing delivery device 520 to a position for treating a valve, and other suitable methods, combinations of devices, etc. may be used.

Figure 10C:
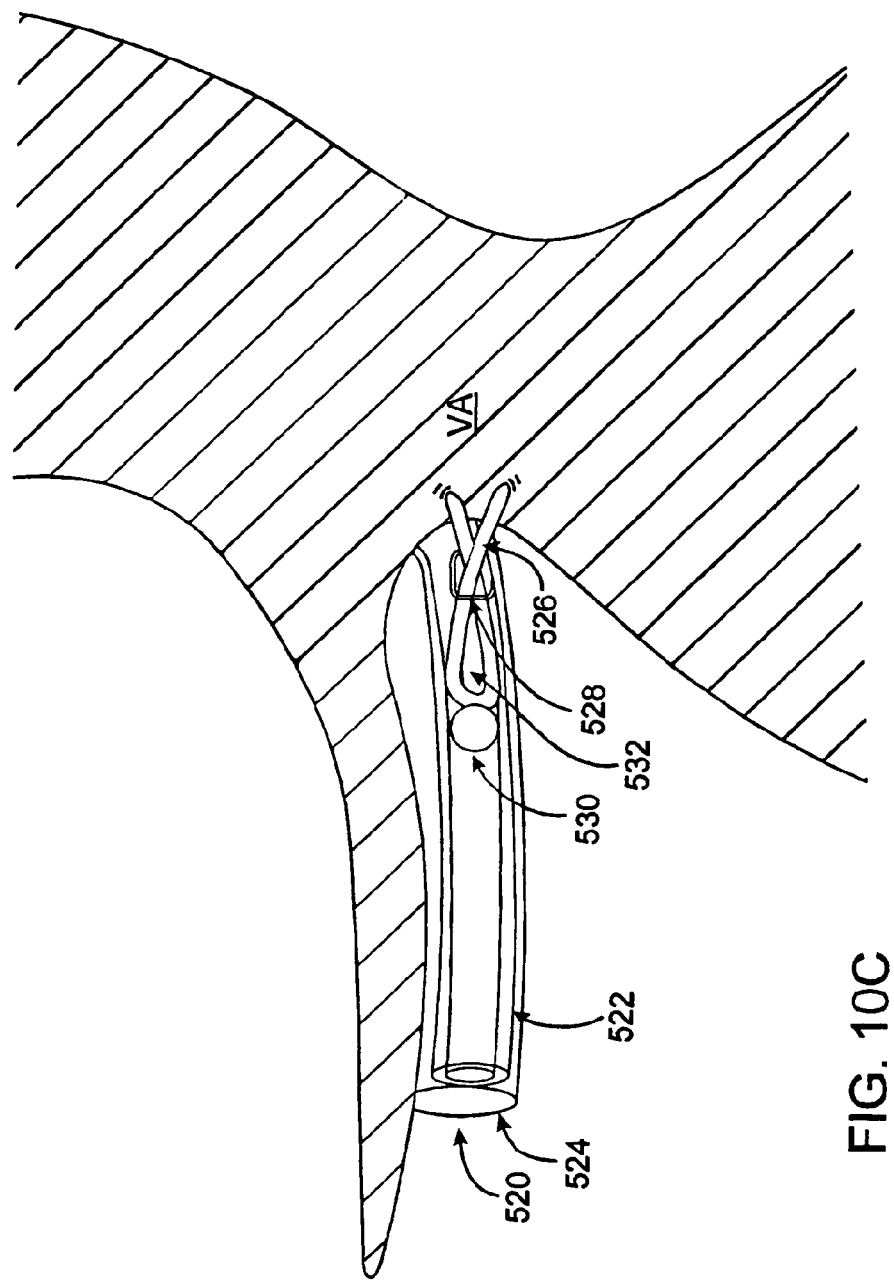
Figure 10D:
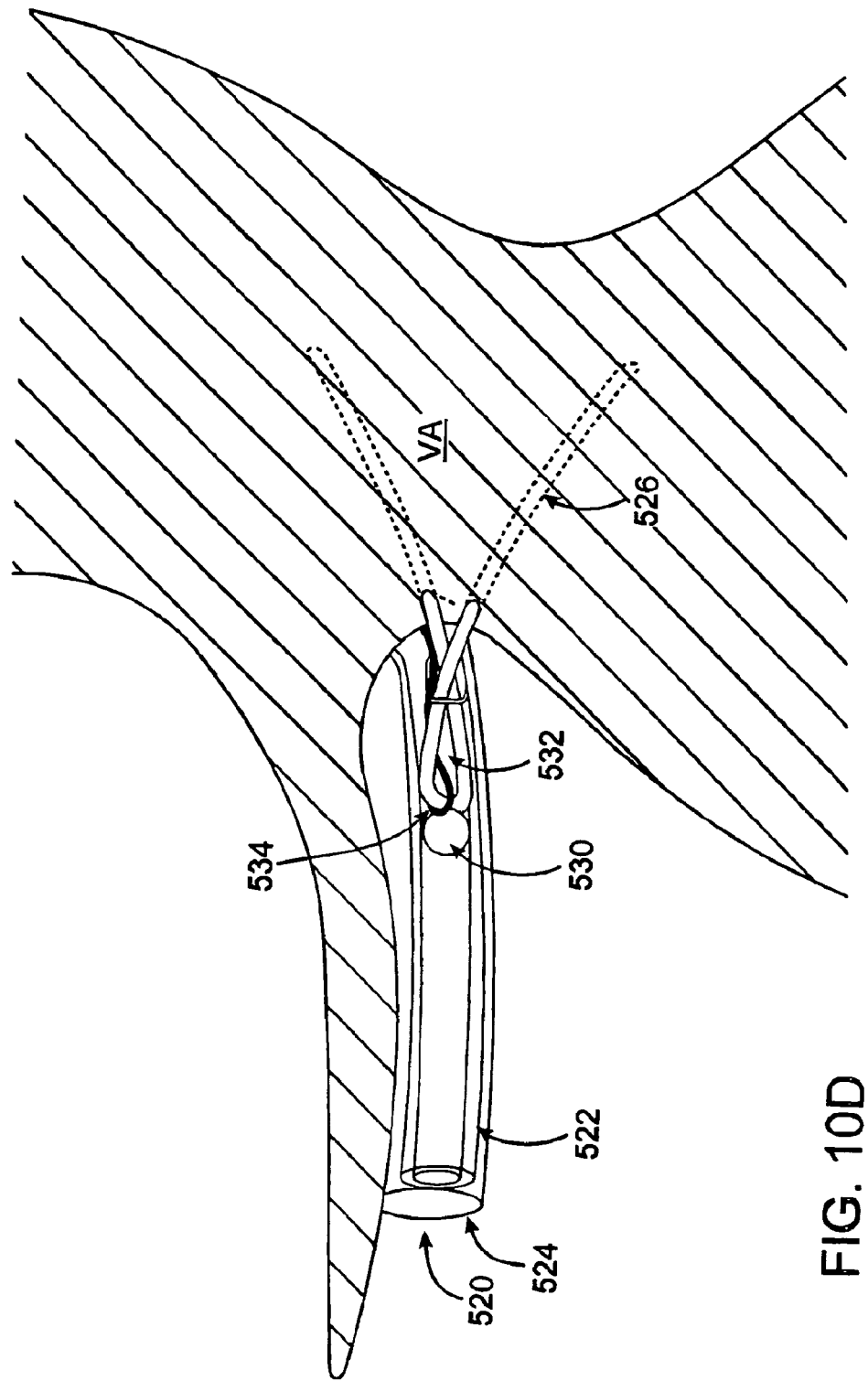

As shown in FIG. 10B, when delivery device 520 is positioned in a desired location for deploying anchors 526, anchor contacting member 530 is retracted to contact and apply force to a most-distal anchor 526 to begin deploying anchor 526 through aperture 528 and into the valve annulus VA (or annular tissue). FIG. 10C shows anchor 526 further deployed out of aperture 528 and into valve annulus VA. FIG. 10D shows the valve annulus VA transparently so that further deployment of anchors 526 can be seen. As shown, in one embodiment, anchors 526 include two sharpened tips that move in opposite directions upon release from housing 522 and upon contacting the valve annulus VA. Between the two sharpened tips, an anchor 526 may be looped or have any other suitable eyelet or other device for allowing slidable coupling with a tether 534.

Figure 10E:
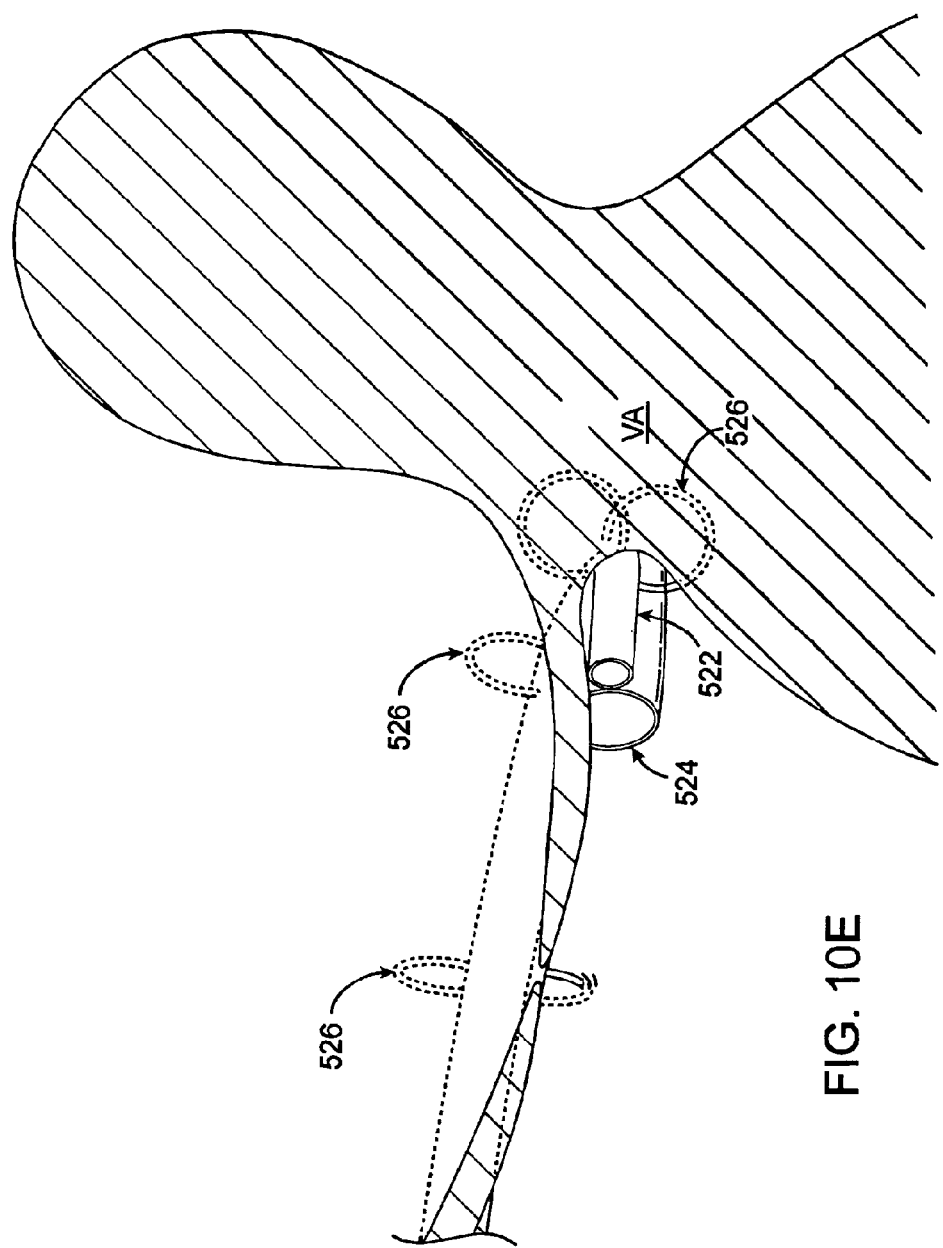

Referring now to FIG. 10E, anchors 526 are seen in their fully deployed or nearly fully deployed shape, with each pointed tip (or "arm") of each anchor 526 having curved to form a circle or semi-circle. In some variations anchors 526 may have any other suitable deployed and undeployed shapes, as described more fully above. FIG. 10F shows anchors 526 deployed into the valve annulus VA and coupled to tether 534, with the distal-most anchor 526 fixedly coupled to tether 524 at attachment point 536. At this stage, tether 534 may be cinched to tighten the annular tissue, thus reducing valve regurgitation. In some embodiments, valve function may be monitored by means such as echocardiogram and/or fluoroscopy, and tether 534 may be cinched, loosened, and adjusted to achieve a desired amount of tightening as evident via the employed visualization technique(s). When a desired amount of tightening is achieved, the implant may be fixed using any of a variety of termination devices and methods.

For example, in one embodiment, cinching tether 534, attaching tether 534 to most-proximal anchor 526, and cutting tether 534 are achieved using a termination device (not shown). The termination device may comprise, for example, a catheter advanceable over tether 534 that includes a cutting member and a nickel-titanium alloy (e.g., Nitinol) knot or other attachment member for attaching tether 534 to most-proximal anchor. The termination catheter may be advanced over tether 534 to a location at or near the proximal end of the tethered anchors 526. It may then be used to apply opposing force to the most-proximal anchor 526 while tether 534 is cinched. Attachment and cutting members may then be used to attach tether 534 to most-proximal anchor 526 and cut tether 534 just proximal to most-proximal anchor 526. Such a termination device is only one possible way of accomplishing the cinching, attachment and cutting steps, and any other suitable device(s) or technique(s) may be used. Additional devices and methods for terminating (e.g., cinching and fastening) may be found, for example, in U.S. patent application Ser. Nos. 11/232,190 and 11/270,034, both of which are hereby incorporated by reference in their entirety. In some embodiments, the termination device is located in the same heart chamber as the remaining portions of the implant, which permits the implant to be wholly implanted in a single heart chamber. In other embodiments, however, a portion of the implant passes transmurally through a septal wall or an outer wall of a heart chamber. In these embodiments, the termination member and optionally one or more anchors may be located in a different heart chamber.

In some embodiments, it may be advantageous to deploy a first number of anchors 526 along a first portion of annular tissue, cinch the first anchors to tighten that portion of the annular tissue, move the delivery device 520 to another portion of the annular tissue, and deploy and cinch a second number of anchors 526 along a second portion of the annular tissue. Such a method may be more convenient, in some cases, than extending delivery device 520 around all or most of the circumference of the annular tissue, and may allow a shorter, more maneuverable housing 522 to be used.

In other embodiments, similar to that shown in FIGS. 10A to 10F, the anchors 526 may be driven out of delivery device 520 through a biocompatible material attached to delivery device 520, thereby attaching the biocompatible material to the annular tissue. Several devices and methods for attaching biocompatible material using anchors are described in U.S. patent application Ser. No. 11/201,949, which is herein incorporated by reference in its entirety. For example, in one embodiment, a Dacron strip may be attached to delivery device 520, extending along device 520 and covering apertures 528. Anchors 526 are then driven out of delivery device 520, through the Dacron strip, into the annular tissue, thus detaching the Dacron strip from device 520 and attaching it to the annular tissue. Such a biocompatible material may facilitate tissue ingrowth of anchors 526 and may enhance attachment generally to the annular tissue. In an alternative embodiment, multiple pieces of biocompatible material, such as separate pieces of material disposed over each of apertures 528, may be used. For example, in one embodiment multiple discs of Dacron material are disposed over multiple apertures 528.

In another embodiment, a distal portion of delivery device 520 may be detachable from a proximal portion of delivery device 520. Such a variation may be configured such that when anchors 526 are deployed from device 520, the distal portion of device 520 detaches from the proximal portion and is attached, via anchors 526, to the annular tissue. In one variation, for example, anchors 526 may pierce through the distal portion of device 520, rather than exiting device 520 through apertures 528. The distal portion may be detachable via any suitable means, such as perforations or the like.

Figure 11A:
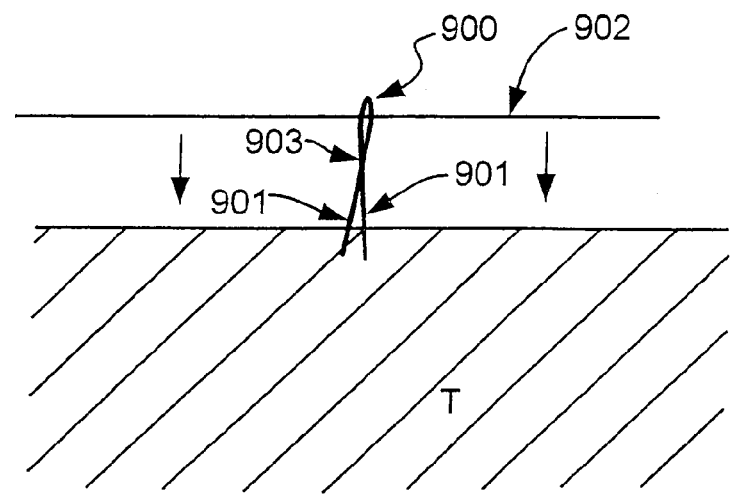
FIGS. 11A through 11C are schematic cross-sectional views of one embodiment of the invention comprising a self-forming anchor attaching to tissue.
Figure 11B:
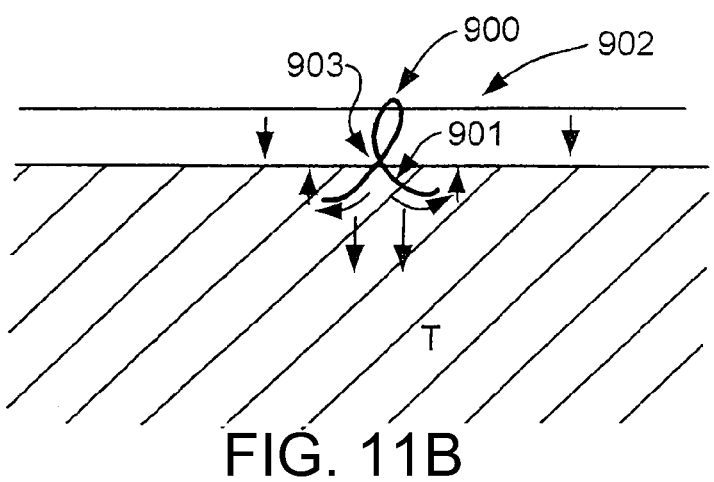
Figure 11C:
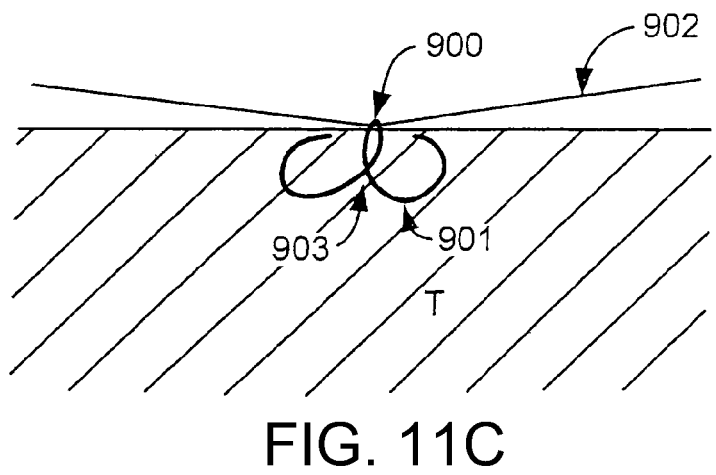

In several embodiments of the invention, self-forming anchors 900 are stored in the delivery device in a straightened configuration, coupled with a tether 902, as shown in FIG. 11A. Anchors 900 are held or restrained in that straightened state, while their deployed configuration is non-linear or curved. Thus, when the straightened anchor 900 is released from the delivery device into tissue T, the anchor 900 actually pulls itself into the tissue T, as shown in FIG. 11B, due to the storage of potential energy in the straightened state and the tendency of each of the arms 901 of anchors 900 to drive the tip of the arm into the tissue as illustrated. Arms 901 are joined together at a junction 903. Each arm 901 is braced against the other arm so that forces exerted by tissue T on each arm 901 are opposed by the other arm 901 wherein the arms are joined to one another. This eliminates the need for an anchor driving device, such as required with staples, thus substantially simplifying the assembly and method. In addition, bracing arms 901 against one another also helps to reduce or eliminate problems associated with tissue deflection. As shown by the hollow-tipped arrows in FIG. 11B, the anchor 900 pulls itself into tissue T as it assumes its natural, curved shape, and exerts forces in vertical, horizontal and curved directions. Finally, after pulling itself into tissue and assuming its natural shape, as in FIG. 11C, anchor 900 is substantially embedded in the tissue T. Various anchor designs and deployment methods are disclosed, for example, in U.S. patent application Ser. Nos. 10/741,130, 10/792,681, 10/900,980, 11/255,400, and 10/901,555, which are hereby incorporated by reference in their entirety.

Figure 12A:
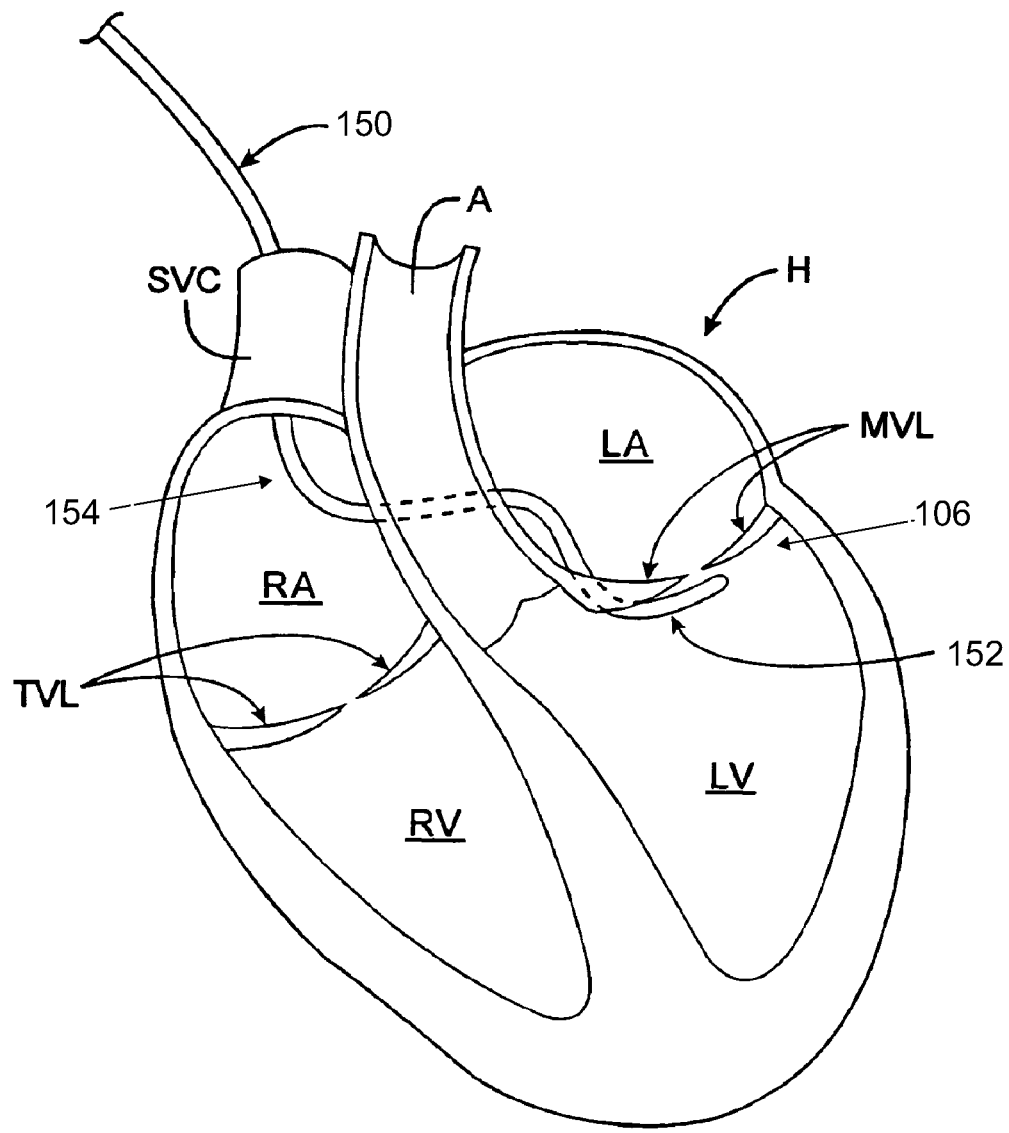
FIGS. 12A and 12B illustrate transseptal and transapical approaches to the left ventricle, respectively.

As explained previously, although one access route to the region 104 or space 106 is a retrograde route through the aorta A to the heart H, other access routes may also be used. Referring to FIG. 12A, with a heart H is shown in cross section, an elongate anchor delivery device 150 may be introduced within the heart H by a transseptal puncture procedure. Transseptal punctures may be performed using a Mullins introducer sheath with a Brockenbrough curved needle through the interatrial septum to access the left atrium LA, but any of a variety of other transseptal puncture devices may be used. From the left atrium LA, supravalvular access to the mitral valve may be achieved, as well as antegrade access to the left ventricle LV through the mitral valve. Similarly, access from the right ventricle RV to the left ventricle LV may be obtained by transseptal puncture of the ventricular septum. In still other embodiments, a catheter device may access the coronary sinus and a valve procedure may be performed directly from the sinus.

Figure 12B:
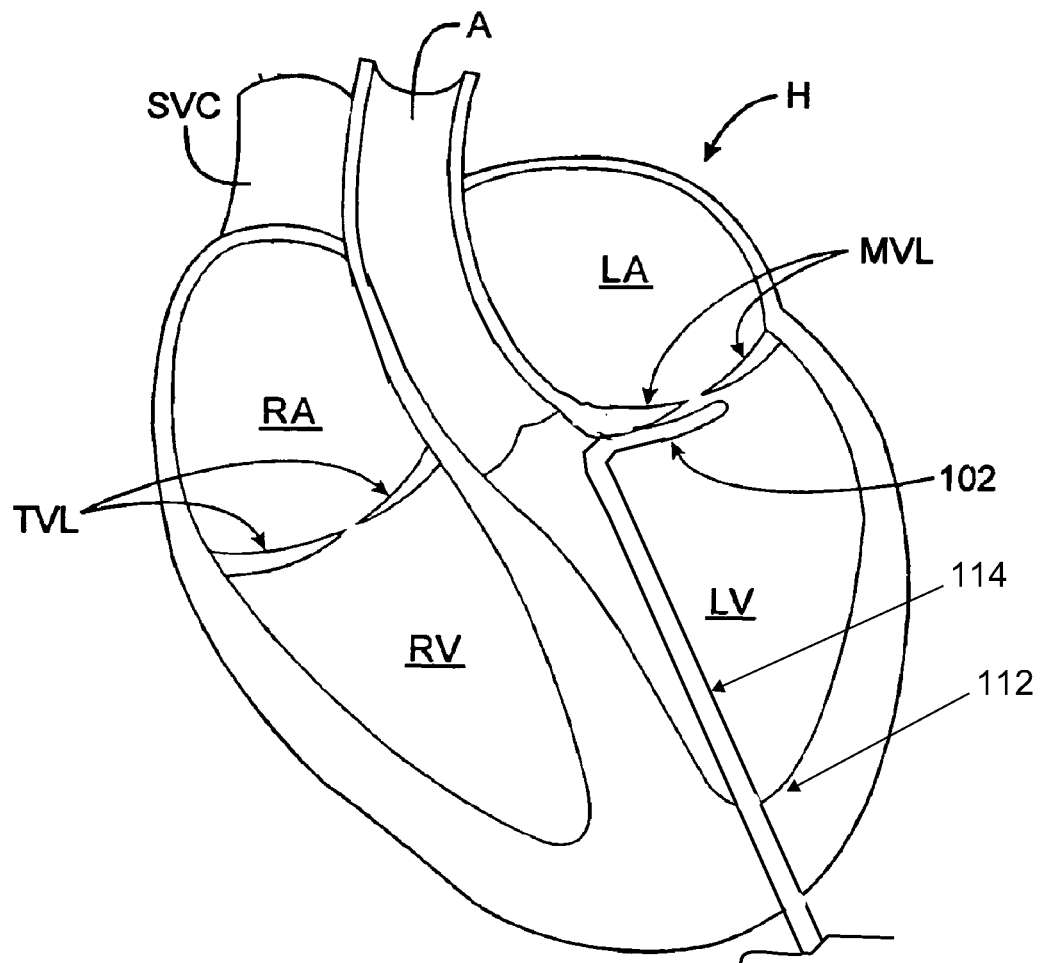

Surgical approaches that may be used have been described above but also include but are not limited to transcatheter procedures made through surgical incisions in the aorta or myocardium. In one particular embodiment, depicted in FIG. 12B, a transapical approach with a surgical delivery device 114 is utilized. In some instances, a transapical approach may provide a more linear route to the subvalvular space 106. The transapical approach may also reduce potential effects of a myocardial incision on cardiac output, as the apical wall 112 may contribute less mechanical effect on left ventricular ejection fraction compared to other sections of the myocardial wall.

Synergistic Implants

Figure 13:
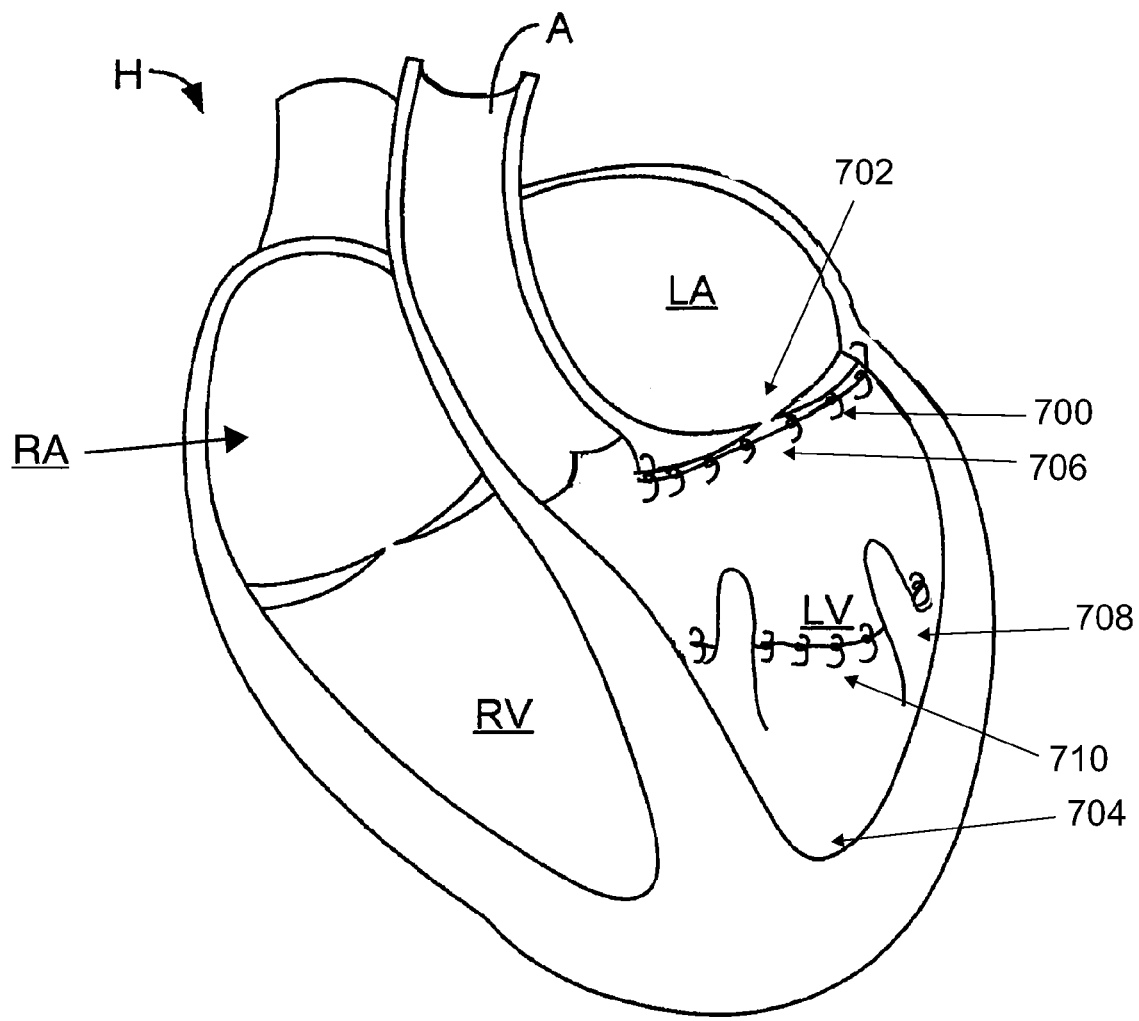
FIG. 13 is a schematic cut-away view of another embodiment of the invention comprising a mitral valve reshaping implant and a ventricular remodeling implant.

In one embodiment, illustrated in FIG. 13, reshaping of the annular tissue of the mitral valve with a cinching implant 706 may be combined with the reconfiguration of the subvalvular apparatus using one or more additional cinching implants 710. The reshaping of the annular tissue may be performed with the embodiments described above, or with other implants. However, unlike some implants, the valve reshaping implants described herein may also be adaptable for implantation in a more inferior position in ventricle. A plurality of tethered anchors may be secured to the myocardium adjacent the papillary muscle and then cinched to tension the myocardium and cause repositioning of one or more papillary muscles. In some embodiments, one or more of the anchors may be attached to or looped around the papillary muscle itself.

In one embodiment, depicted schematically in FIG. 13, the anchors may be oriented circumferentially with respect to the long axis of the ventricle LV between the base 702 and the apex 704 of the ventricle LV. When cinched, the implant 710 reduces the relative distance between the papillary muscles 708. In some instances the papillary muscle 708 may be displaced in the presence of dilated cardiomyopathy, or as a result of ventricular remodeling secondary to mitral valve regurgitation. By reducing the distance between the papillary muscles 708, the valve leaflet coaptation may be improved by alleviating the pull of the mitral valve leaflets MVL by the taut chordae tendineae (not shown) attached to displaced papillary muscles 708. One or more imaging modalities, including but not limited to magnetic resonance imaging, spiral CT, fluoroscopy or ultrasound, may be used to visualize the valvular apparatus and to determine the preferred orientation of the cinching implant to achieve the desired effect. For example, if ultrasound imaging identifies redundant chordae tendineae as one source of valve regurgitation, one or more cinching implants may placed with a longitudinal orientation between the associated papillary muscle 708 and the apex 704 of the ventricle LV to increase tension in the chordae and reduce leaflet prolapse.

Even where a valve reshaping implant adequately treats the valve regurgitation, the placement of cinching implant in an inferior location in the ventricle may still be beneficial for treating or limiting ventricular dilation. Under the LaPlace principle, by reducing the radius of the heart chamber, myocardial strain from volume overload can be reduced and may lead to some recovery of myocardial function over time. Therefore, in addition to repositioning of the papillary muscles 708 to improve valvular function, the ventricular implant 710 may also improve the contractile function of the left ventricle LV. Various imaging modalities mentioned previously can be used to identify locations to reduce ventricular dimensions, and in some embodiments, multiple cinching implants may be used in the ventricle to achieve the desired result.

Figure 25:
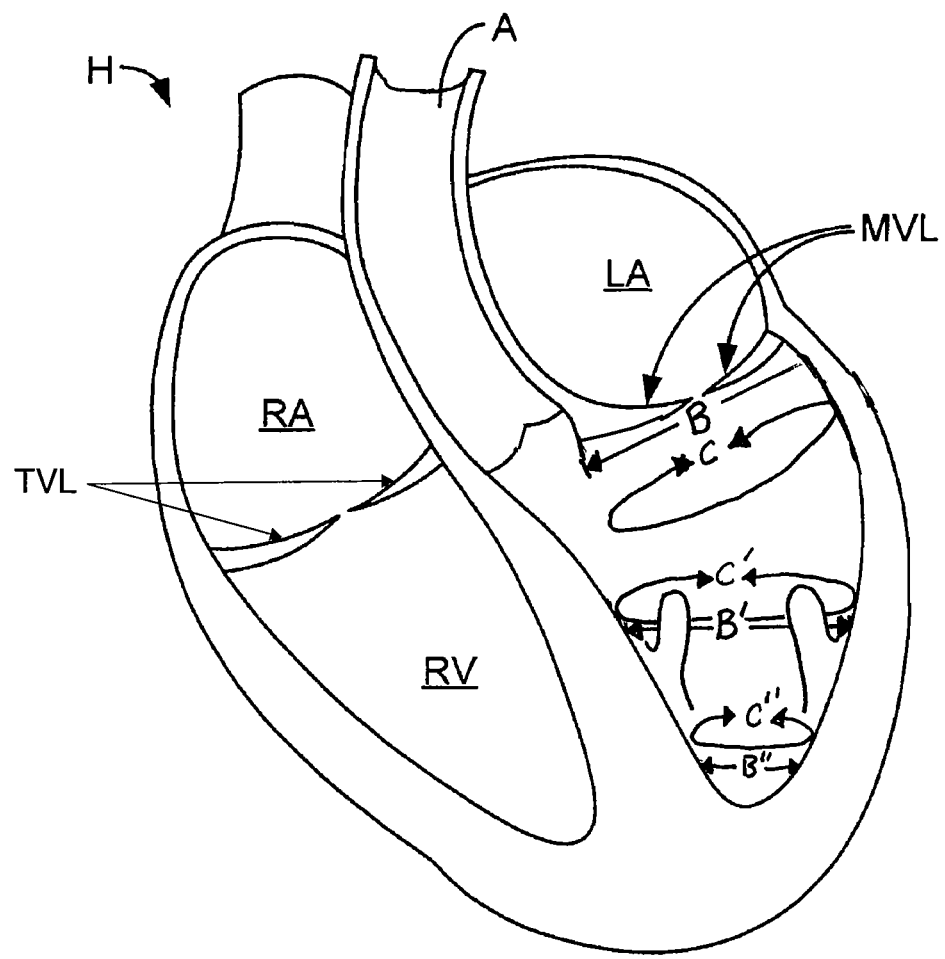
FIG. 25 is a schematic view of the heart illustrating various dimensions of a heart chamber.

The reshaping of a ventricle may be performed or assessed along any of a variety of dimensions or vectors. For example, referring to FIG. 25, in some embodiments of the invention, the reshaping of a ventricle or a valve may occur with respect to the diameter B or the circumference C about a valve orifice. In one embodiment, the diameter B and the circumference C with respect to the region 104 of a ventricle is reshaped. In addition to the reshaping of to valvular structures, reshaping can also be performed with respect to the non-valvular structures of a heart chamber. For example, one or more of the diameters or circumferences of the ventricle may be reshaped. As shown in FIG. 25, the diameter B' and the circumference C' of the ventricle located generally at or above the papillary muscles may be reshaped. The diameter B" and circumference C" of the ventricle at or below the papillary muscles may also be reshaped. The orientation of the diameter and circumference that is reshaped or assessed can vary, but in some embodiments, the diameter or circumference may be in a generally perpendicular orientation with respect to a longitudinal axis of a ventricle. One of skill in the art will understand that the longitudinal axis may be characterized in a number of ways, including but not limited to a longitudinal axis from a valve orifice to an apex of a heart chamber, or from the apex of a heart chamber to a point that generally splits the ventricular volume in half. Similarly, some of the implantation dimensions or vectors may also be oriented with respect to the anterior-posterior axis or the septolateral axis of the heart chamber.

Figure 26:
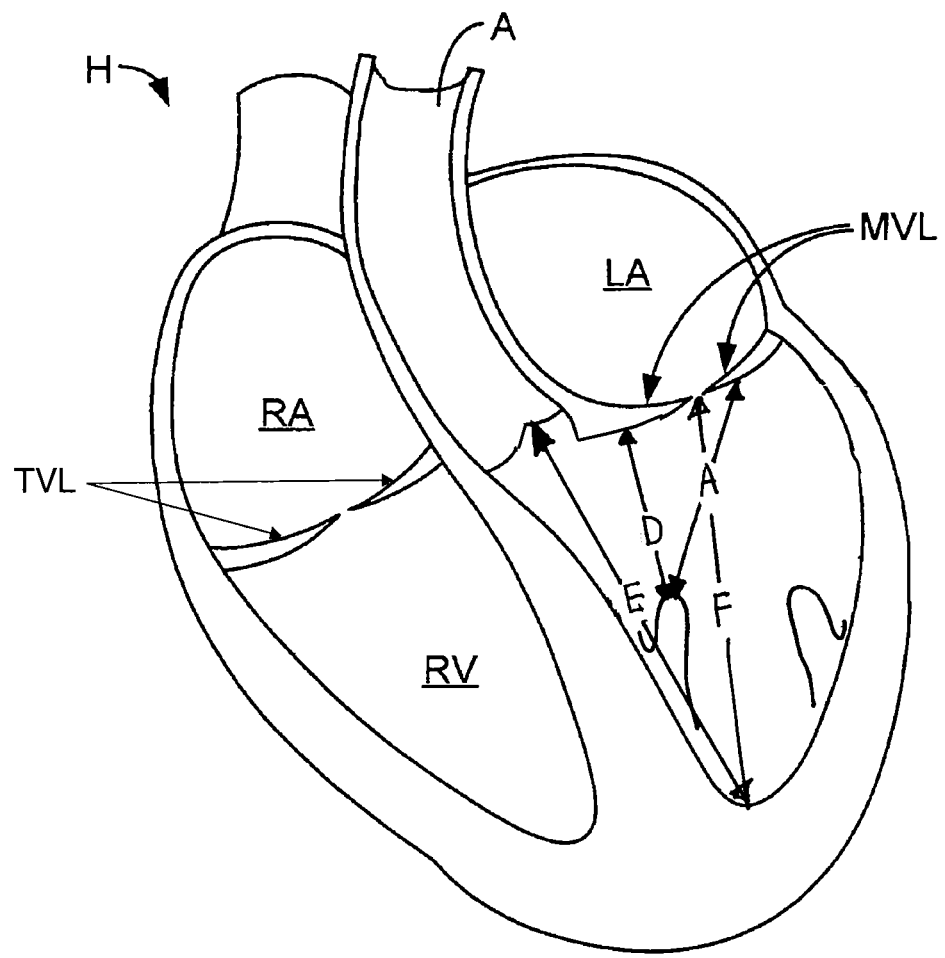
FIG. 26 is a schematic view of the heart illustrating various dimensions of a heart chamber.

Referring to FIG. 26, in some embodiments, the distances A, D between a papillary muscle and a valve leaflet may be reshaped. This distance A or D may be between a papillary muscle and its associated valve leaflet, or between a papillary muscle and an unassociated valve leaflet, respectively. Although the distances A, D depicted in FIG. 26 are shown from the tip of the papillary muscle, these distances may also be measured from the base of the papillary muscle. Similarly, distances involving a valve leaflet may be measured from the distalmost section, the middle or the base of the valve leaflet. In other embodiments, the reshaping of the heart may occur between the apex of a heart chamber and one or more valves. For example, reshaping may occur along the distance E between the outlet valve and the apex of a heart chamber, and/or along the distance F between the inlet valve and the apex.

Thus, one or more shortening implants, including the cinching implants described herein, may be generally placed or oriented between or along one or more of the dimensions or vectors, as exemplified above. In some embodiments, multiple implants may be placed in a generally parallel arrangement or in a fan-like pattern along one or more of the dimensions or vectors. The placement of a shortening implant is not limited to the vectors or locations described herein, and may occur with any angle, length or skewing as needed. Although the dimensions depicted in FIGS. 25 and 26 are wholly contained within a single heart chamber, in other embodiments, the dimensions may include cardiac sites outside of a single heart chamber.

Referring back to FIG. 13, although the two cinching implants depicted have similar size anchors and tether lengths, in other embodiments these features may be optimized for the intended implant location. For example, larger anchors may be used when performing ventriculoplasty. Likewise, the length of the tether and the number of coupled anchors may be increased with myocardial wall applications due to the larger circumferential dimensions of the ventricle compared to the annular tissue regions. Furthermore, the desired tissue-related characteristics of the cinching implants may differ, depending on the implant location. For example, tissue fibrosis around a valve reshaping implant may be desirable to improve implant biocompatibility and to resist further annulus dilation. Further details regarding tissue fibrosis around a valve reshaping implant may be found in U.S. patent application Ser. No. 11/255,400, which was previously incorporated by reference. Tissue fibrosis around a ventricular implant, however, may reduce the contractility and compliance of the myocardial wall and result in reduced ejection fractions. For this reason, it may be desirable to configure valve and ventricular implants for different tissue responses. For example, ventricular implants may benefit from an anti-proliferative drug coating to limit tissue fibrosis. The anti-proliferative drug may be any of a variety of anti-proliferative agents known in the art, including but not limited to paclitaxel, sirolimus, everolimus, a corticosteroid and the like.

Although a number of surgically implanted ventricular devices and procedures are known in the art, the percutaneous or transvascular implantation of a ventricular device may pose a significant challenge, due to the instability from the wall motion of a beating heart. To assure adequate contact between the delivery device and the myocardium and reliable positioning of a ventricular cinching implant, the delivery device may be stabilized against a less mobile portion of the cardiac structure during the implantation procedure. In some embodiments, the delivery device for a ventricular implant may be stabilized in the subannular groove, the subvalvular space, or the apex of the left ventricle.

Figure 14A:
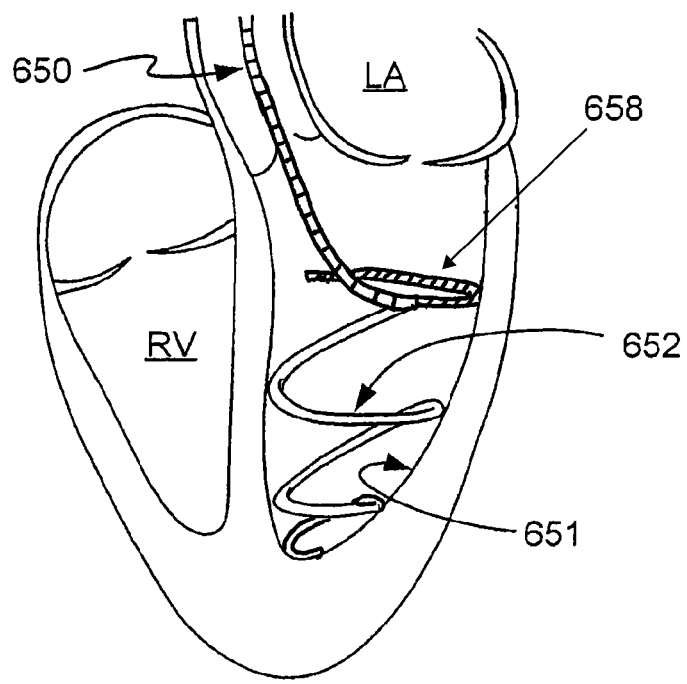
FIGS. 14A through 14D depict various embodiments of support members for stabilizing an anchor delivery device against a myocardial surface.

FIG. 14A depicts an embodiment of the ventricular implant delivery device, comprising a support member configured to seat in the apical region of the left ventricle during implantation. The support member depicted in FIG. 14A is a helical support member 652 coupled to a distal end of anchor delivery device 658, but other shapes and configurations may also be used. In other embodiments, helical support member 652 may alternately extend out of a guide catheter 650 to contact the heart wall 651 and support the anchor delivery device 658. Preferably the support member 652 has a delivery configuration with a reduced profile to facilitate passage of the support member 652 to the target site, and an expanded configuration with an enlarged profile for seating against the apical region 704 of the left ventricle or other stable region of an anatomical structure. Helical member 652 may be made of any suitable material, including but not limited to nickel-titanium alloys (e.g., Nitinol), stainless steel or the like. Any suitable mechanism may be used for extending helical member 652 into the left ventricle or other chamber. For example, helical member 652 may be pushed out of guide catheter 650, but may alternatively be extended out the guide catheter with extension of anchor delivery device 658.

Figure 14B:
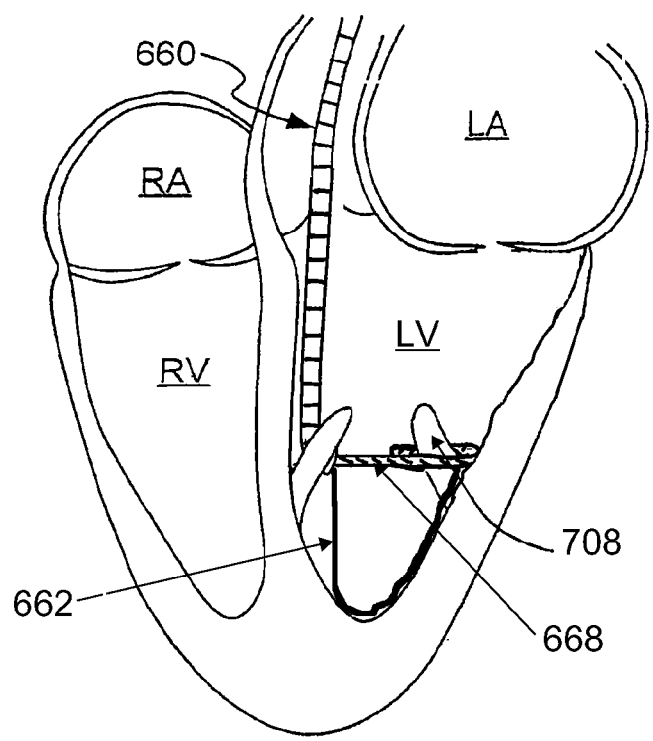

In another embodiment illustrated in FIG. 14B, the delivery device may be stabilized against the superior surfaces of the papillary muscles 708. In some examples, stabilization against the papillary muscles 708 may provide mid-chamber support during implantation of a ventricular cinching implant 710. The anchor delivery device 668 may optionally comprise a deployable J- or U-shaped support member 662 that is movably coupled with a distal portion of an anchor delivery device 668, both of which are advanceable through a guide catheter 660. Upon being advanced out of the distal end of guide catheter 660, U-shaped member 662 may automatically spring out, or alternatively may be manually extended, to contact the inner surface of the heart wall and/or to contact a papillary muscle 708. Manual extension of the U-shaped member 662 may permit the user to titrate the positioning of the delivery device to the desired location in the heart chamber. Such a U-shaped member 662 may automatically deform from a straight configuration for delivery through guide catheter 660 into a U-shaped configuration, such as if member 662 is made of spring stainless steel or nickel-titanium alloys (e.g., Nitinol). In another embodiment, the U-shaped member 662 may be connected to anchor delivery device 668 at or near the distal end of the device 668 and may be pushed distally to force the U-shaped member 662 to expand into its U-shape. In still another embodiment, the U-shaped member 662 may be attached proximally and may be pulled into its expanded configuration. Any suitable method for changing the shape of U-shaped member 662 from straight to U-shaped may be used in some variations.

Figure 14C:
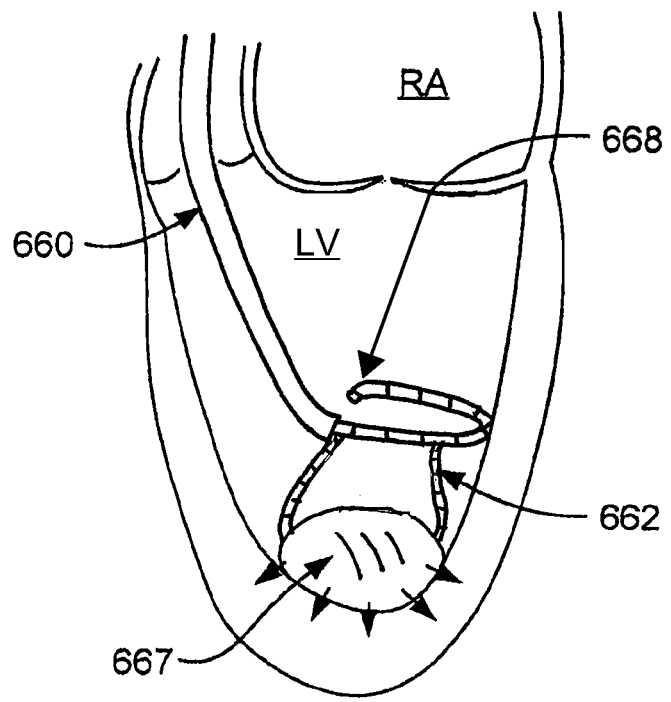

In another embodiment depicted in FIG. 14C, the U-shaped member 662 may optionally include an expandable member 667, such as an inflatable balloon. Expandable member 667 may be expanded to provide further force against and support of anchor delivery device 668, to enhance its contact with ventricular wall 651. In FIG. 14C, the expandable member 667 is circumferentially mounted on the U-shaped member 662, similar to a balloon angioplasty-type catheter but with a greater expansion diameter. In some embodiments, the balloon may have an expanded diameter of at least about 1 cm, at least about 2 cm, of at least about 3 cm. In other embodiments of the invention, the expandable member 667 may be mounted and inflated directly from the delivery device, without a U-shaped member 662.

Figure 14D:
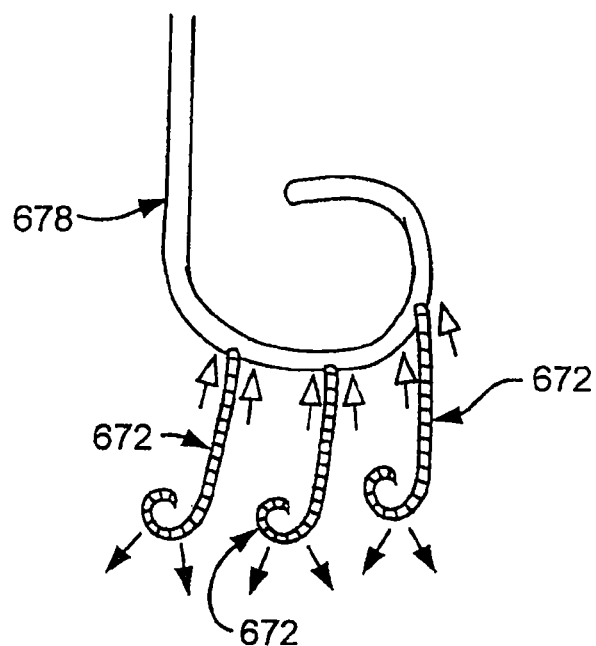

In another embodiment of the invention, shown in FIG. 14D, multiple spring members 672 may be coupled with a distal end of an anchor delivery device 678 to provide force against an inner surface of a heart wall (solid tipped arrows) to support the anchor delivery device 678 against the heart wall of the heart chamber (hollow tipped arrows). Thus, an anchor delivery device may include any of a number of suitable support members to support an anchor delivery device against the myocardium, thus possibly enhancing the ability of the delivery device to delivery tissue anchors to the target tissue in the left ventricle.

In some of the embodiments, the support members of an anchor delivery device may have a fixed length or configuration such that the anchor delivery device is configured to position an implant at a single level or position relative to an anatomical structure or site in the heart, e.g. the apex of the left ventricle. Further manipulation by the physician may permit the anchor delivery device to be positioned at other levels with a fixed configuration device. In other embodiments, the length of the support member(s) may be manipulated with respect to the guide catheter or the anchor delivery device to permit variable positioning of the anchor delivery device at different levels or sites of the heart chamber. The different sites include but are not limited to the apex, the region between the apex and the lower boundary of the papillary muscles, the papillary muscles, the subvalvular space, and the subannular groove region. The implantation sites can also be characterized by a percentage or percentage range with respect to an axis of the particular heart chamber. These percentages include but are not limited to about 0%, about 10%, about 20%, about 30%, about 40%, about 50%, about 60%, about 70%, about 80%, about 90% and about 100%. Along a longitudinal axis of the left ventricle, for example, the apex may be characterized as about 0% of the longitudinal axis while the subannular groove region may be characterized as about 100% of the longitudinal axis.

Although in some embodiments, the cinching implants may be oriented at an angle in the heart chamber so that they are orthogonal to the longitudinal axis of the heart chamber, in other embodiments the implants may be oriented at any angle or range of angles, from about zero degrees to about 180 degrees with respect to the longitudinal axis, including but not limited to about 15 degrees, 30 degrees, about 45 degrees, about 60 degrees, about 75 degrees, about 90 degrees, about 105 degrees, about 120 degrees, about 135 degrees, about 150 degrees, about 165 degrees. With non-orthogonal angles, the implant may be located across two or more levels of the heart chamber as described previously. A particular implantation angle may be facilitated by the fixed or variable angle between the support member and the anchor delivery device, or from manual positioning by the physician.

Figure 15:
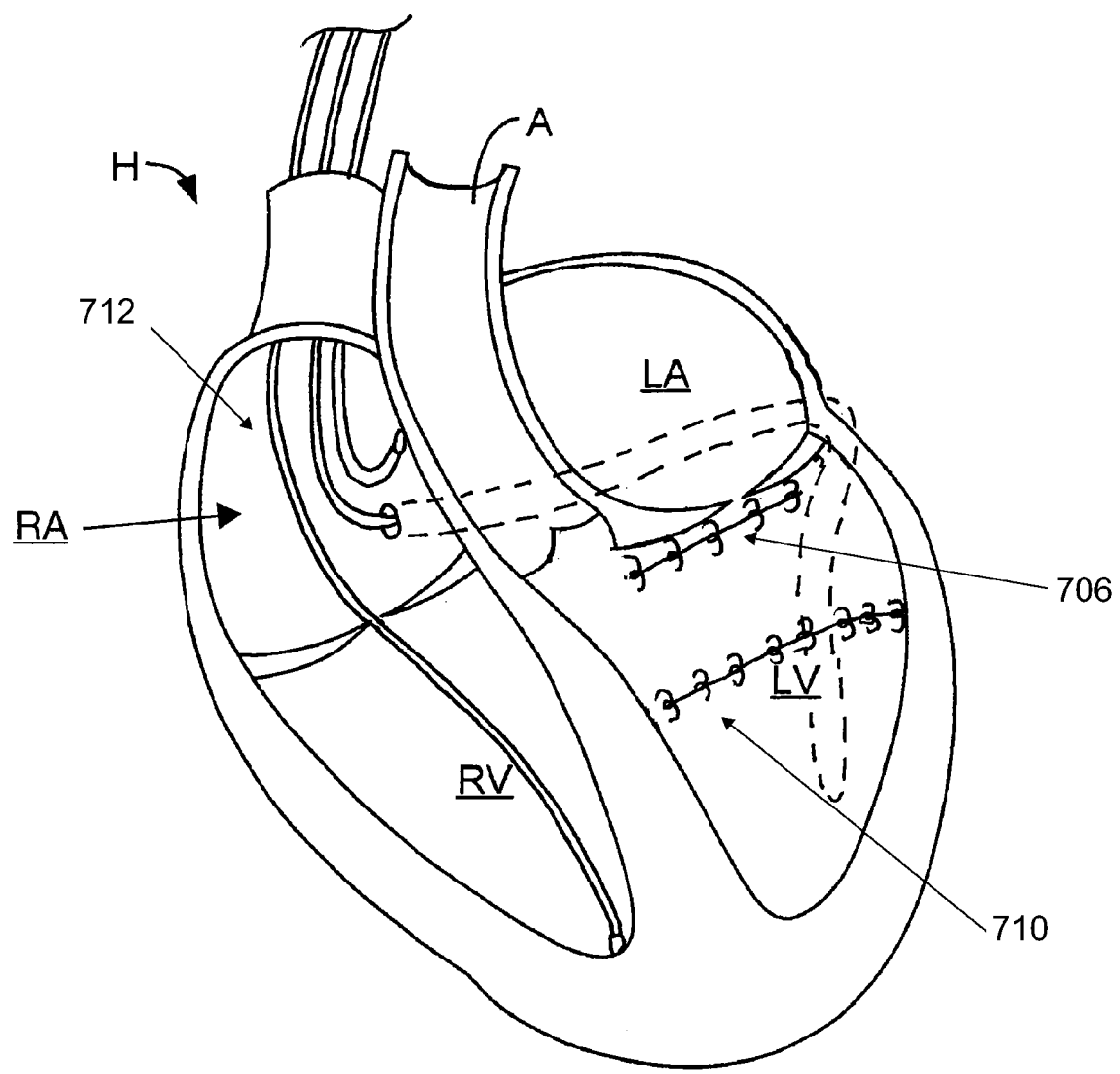
FIG. 15 is a schematic representation of a heart with a mitral valve reshaping implant, a ventricular reshaping implant, and leads from a cardiac rhythm management system.

Another challenge involving a papillary reconfiguration or ventriculoplasty implant is the potential arrhythmogenic risk to a patient. Patients who could benefit from such implants may be at-risk for conduction abnormalities from ventricular dilatation. However, annular tissue may be relatively electrophysiologically inert compared to the myocardial tissue. Patients with tissue anchors attached to the myocardium may benefit from an implantation of a cardiac rhythm management device with a defibrillator component. FIG. 15 depicts one such embodiment, comprising multiple implants. In some examples, multiple implants may be used for synergistic treatment of mitral regurgitation and related sequelae. Here, the patient has a mitral valve reshaping implant 706 for treatment of valve regurgitation, a ventriculoplasty implant 710 for treatment of ventricle dilatation, and a set of electrodes 712 for monitoring and treatment of arrhythmias and conduction delays that may reduce ventricular contractile efficiency. In addition to treating common risks associated with mitral regurgitation, the pacemaker-defibrillator leads 712 and the cinching implants 706, 710 may be synergistically configured for implantation using a common guide catheter, which may reduce implantation procedure time and costs.

Figure 16:
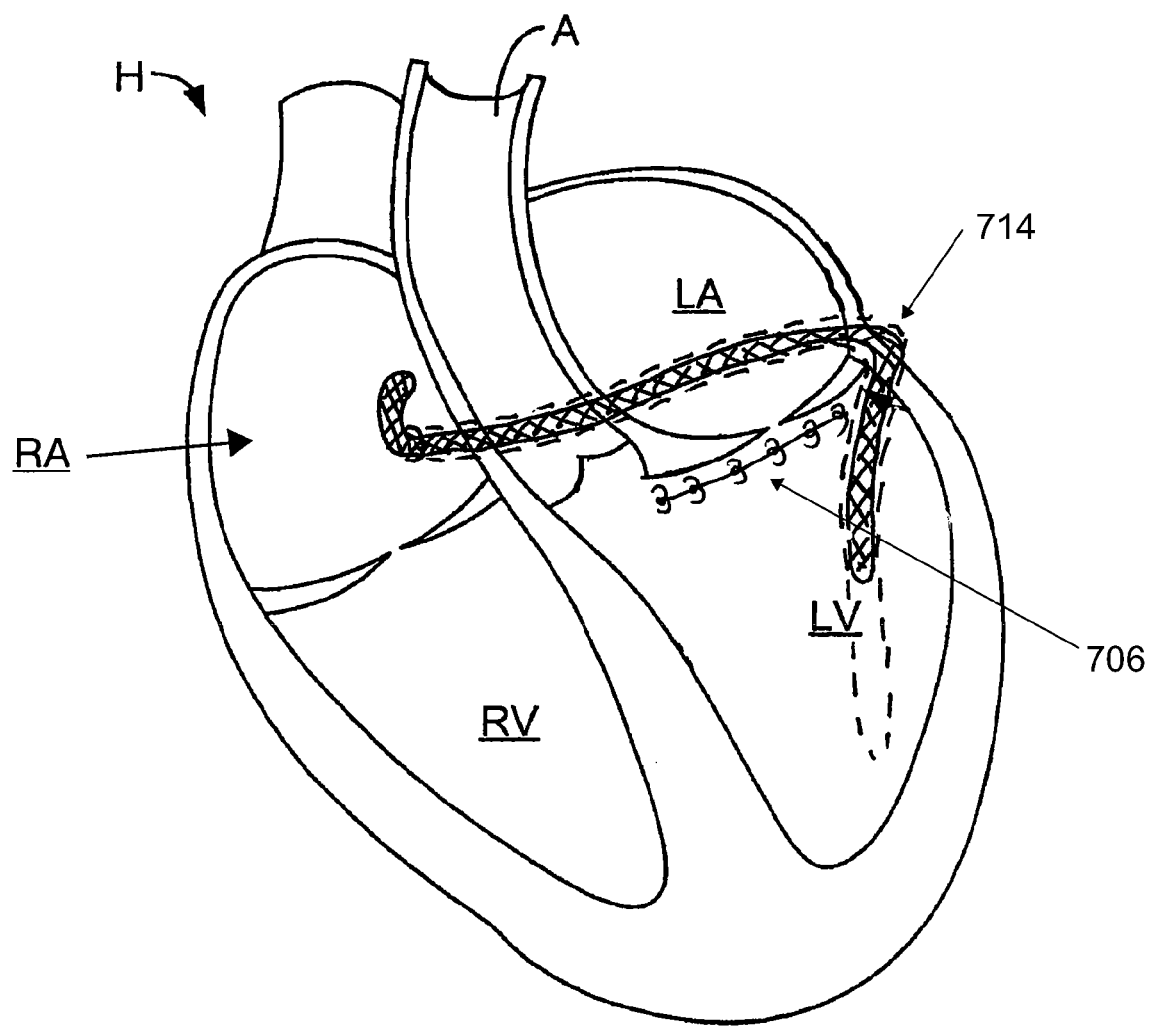
FIG. 16 is a schematic representation of a heart with a coronary sinus reshaping implant and a ventricular reshaping implant.

Although some of the preceding examples utilize two minimally invasive tissue anchor implants for reshaping cardiac structures, not all of the implants need to have a design comprising tissue anchors. In FIG. 16, for example, a coronary sinus annuloplasty implant 714, such as the C-CURE™ device by Mitralife, Inc. (Santa Rosa, Calif.), may be used in conjunction with the tissue anchor implant. Different tissue anchor-based implants may be used, including those described in U.S. Pat. Pub. 2007/0112424 assigned to Mitralign, Inc., of which those portions that relate to suitable devices and delivery methods for use herein incorporated by reference. Various designs of the coronary sinus annuloplasty implants are disclosed in U.S. Pat. No. 6,402,781 to Langberg et al., of which those portions relating to suitable devices and methods for use herein are also incorporated by reference. The embodiment depicted in FIG. 16 also illustrates the use of dual valve reshaping implants to achieve a further degree of annulus diameter reduction. The use of both peripheral and central reshaping forces from two difference types of mitral valve implants 706, 714 may achieve better annulus reshaping than any annuloplasty implant alone.

Also, while both types of implants 706, 714 may be placed during the same procedure, the second implant may be placed at a later date. With reference again to FIG. 16, a patient with an existing mitral valve reshaping implant 714 may receive an additional implant 706 to reduce any residual regurgitation from the original surgery, or any regurgitation that develops later as a result of disease progression. In other embodiments, a patient with a pre-existing surgically implanted annuloplasty ring may receive a second mitral valve annuloplasty implant that is translumenally implanted by a catheter. The second implant may also be placed several weeks, months or years after the original implant.

The use of a tissue-anchor implant may allow further annular tissue reshaping without requiring removal of an existing coronary sinus implant or surgically implanted annuloplasty ring. The self-deploying design of tissue anchor design may also generate less concern that the second implant is interfering with existing implant because the self-deploying design permits securement of the implant to a wider range of structures or surfaces.

Figure 17:
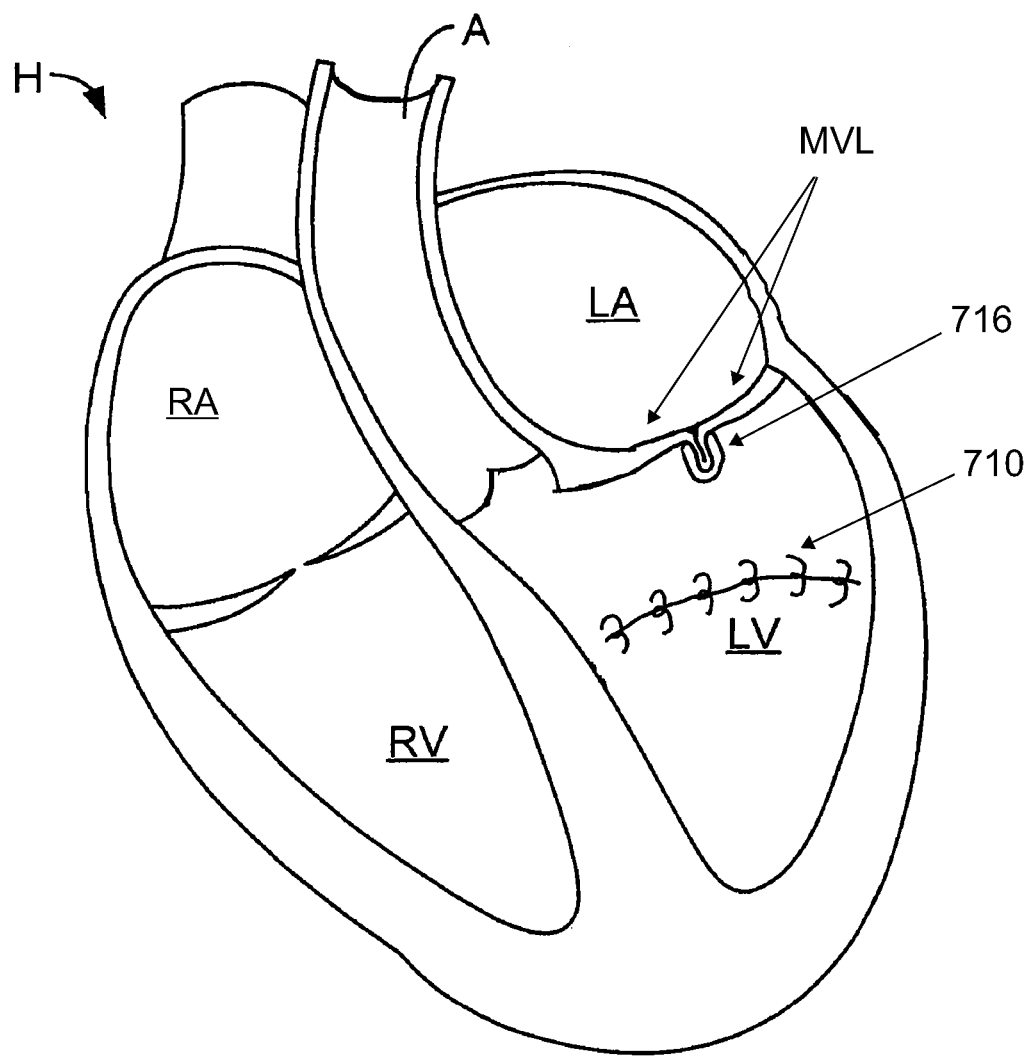
FIG. 17 is a schematic representation of a heart with a mitral valve leaflet clip and a ventricular reshaping implant.
Figure 18:
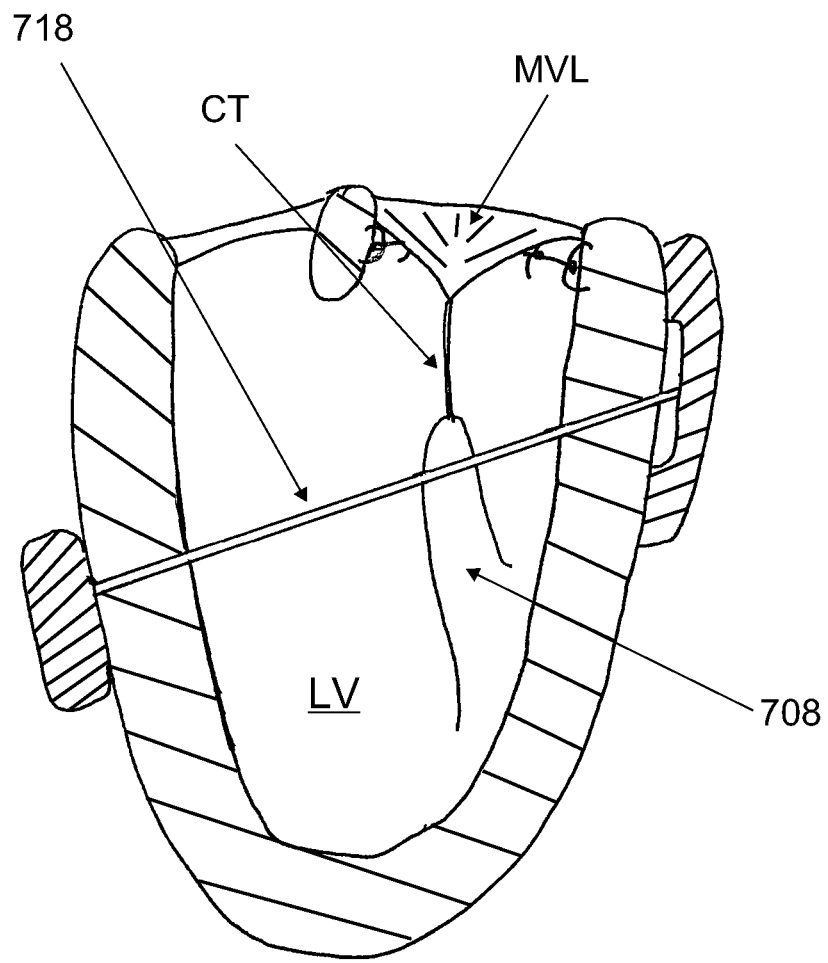
FIG. 18 is a lateral schematic view of a left ventricle with a mitral valve reshaping implant and a ventricular tension implant.
Figure 20:
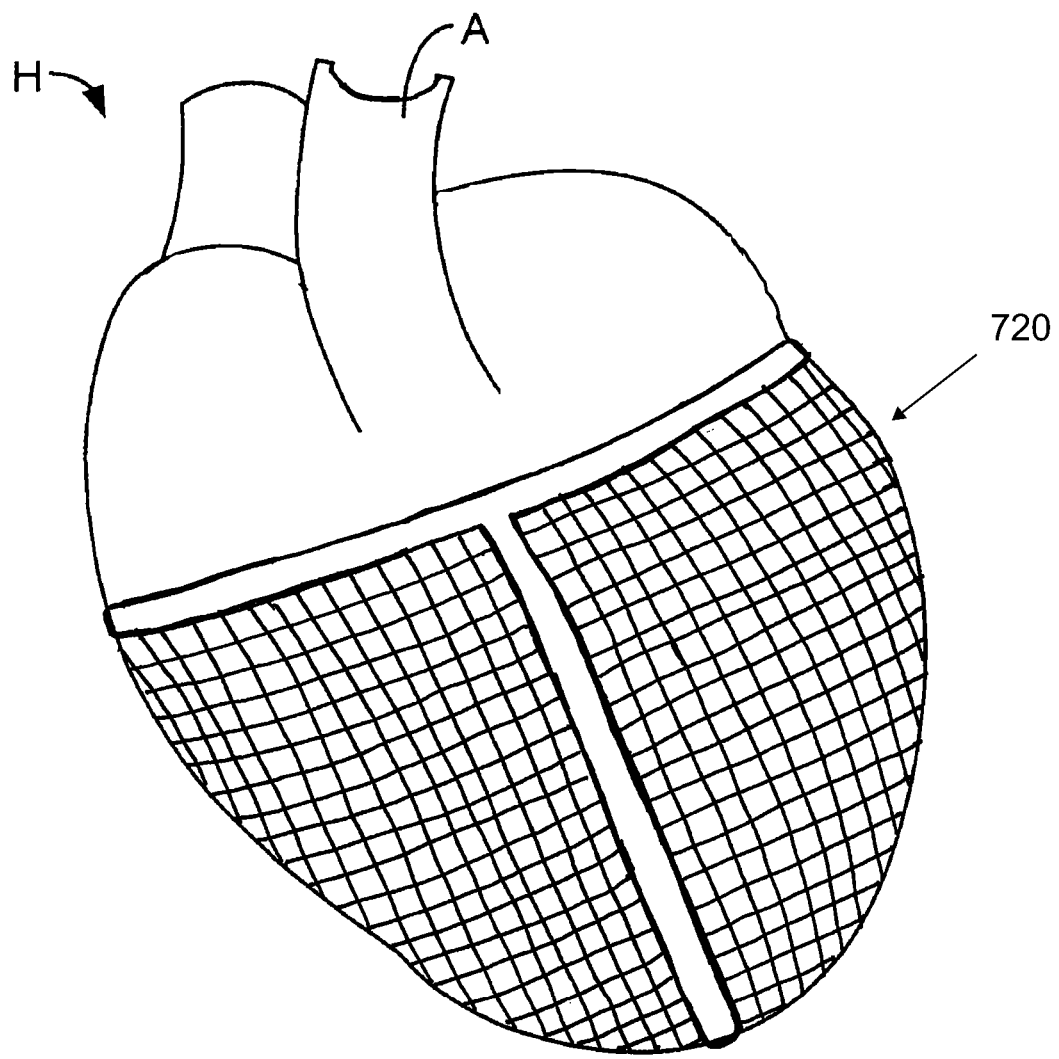
FIG. 20 is a schematic view of an external surface of the heart with an external cardiac support device.

FIGS. 17, 18 and 20 depict the use of an anchor-based ventricular implant 710 along other complementary cardiac devices for the multimodal treatment of mitral valve regurgitation and related sequalae. In FIG. 17, a clip device 716, such as the one produced by Evalve, Inc. (Redwood City, Calif.) may be used to restrain the free edges of a mitral valve for reducing regurgitation, while a cinching implant is used synergistically to reduce ventricle size and alleviate volume overload. Leaflet clips and other suitable valvular apparatus lasso devices are described in U.S. Pat. No. 6,629,534, those portions of which relating to suitable devices and delivery methods for use herein are also incorporated by reference. Conversely in FIG. 18, a myocardial tension implant 718, such as the Coapsys® device by Myocor® Inc. (Maple Grove, Minn.), may be used with a cinching valve reshaping implant 706. Various designs for transmural and transchamber myocardial tension implants 718 and related implantation tools are described in U.S. Pat. Nos. 5,961,440 and 6,260,552, both of which the portions relating to suitable devices and delivery methods are herein incorporated by reference.

In addition to the transmural myocardial tension device shown in FIG. 18, other implants requiring access to the epicardial surface may also be used with annular tissue and ventricular cinching implants 706, 710. Another example of an external cardiac support device that limits cardiac dilatation is the CorCap™ cardiac support device by Acorn Cardiovascular, Inc. (St. Paul, Minn.), which depicted in FIG. 20 and described in U.S. Pat. No. 7,278,964, those portions of which relating to suitable devices and delivery methods for use herein are also incorporated by reference.

Figure 21A:
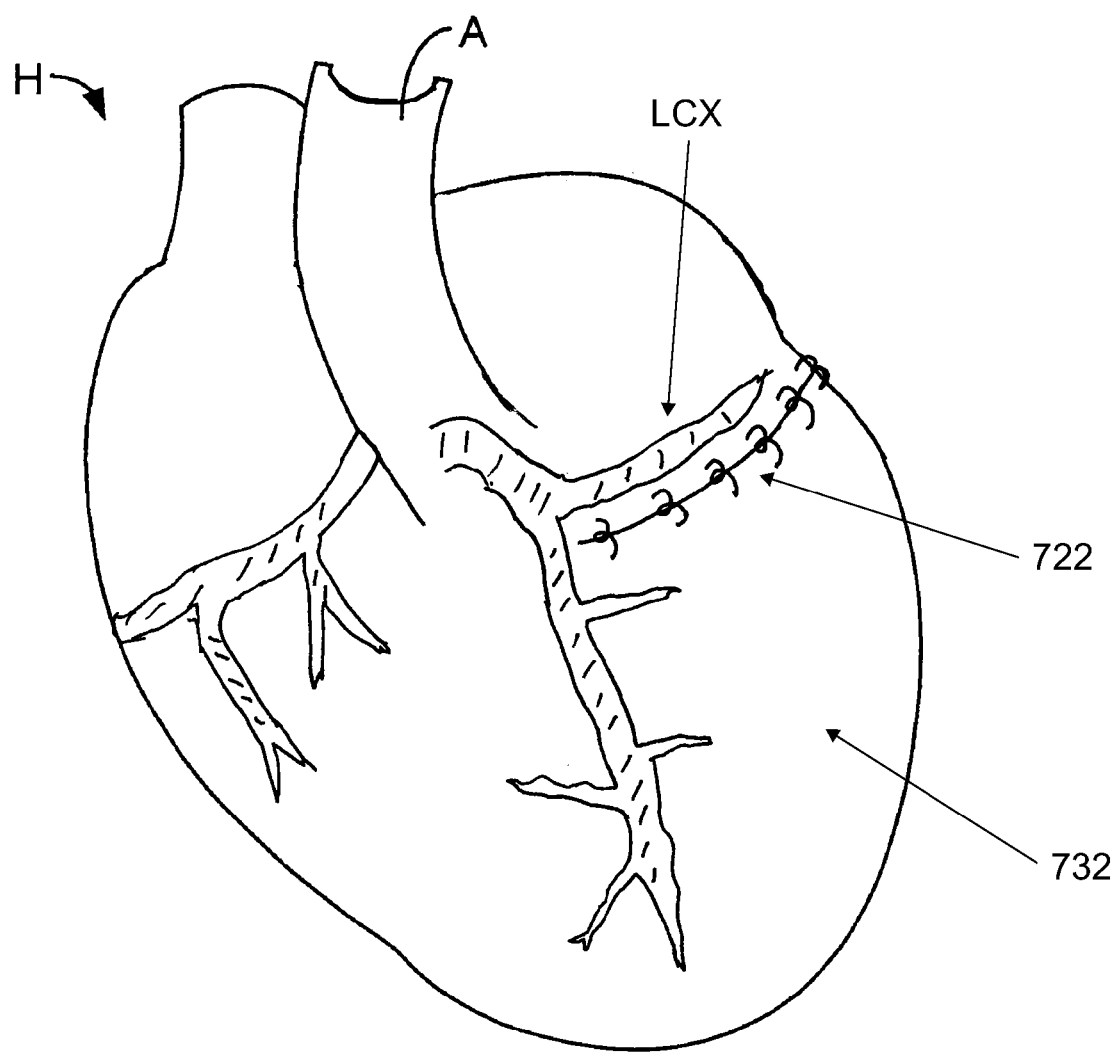
FIGS. 21A and 21B are schematic views of an external surface of the heart with a mitral valve reshaping implant placed on the epicardial surface.

One or more cinching implants may also be applied to the epicardial surface of the heart. Referring to FIG. 21A, an epicardial cinching implant 722 may be placed on the heart H using a thorascopic procedure or an open surgical procedure through an incision in the pericardial sac. In one embodiment, the cinching implant 722 may be secured at a circumferential epicardial location inferior to the left circumflex artery LCX and then cinched to reduce the diameter of the mitral valve annulus (not shown). During some procedures, when positioning the implant 722, to the cinching implant 722 may be positioned to limit or avoid impingement of the coronary arterial and venous system. This can be done with direct visualization of the epicardial surface 732 using a minimally invasive fiber optic scope or by direct visualization with the creation of a pericardial flap or window. Identification of the coronary surface vasculature can also be performed indirectly with dye injection into the vasculature during spiral CT scan or fluoroscopy.

Figure 21B:
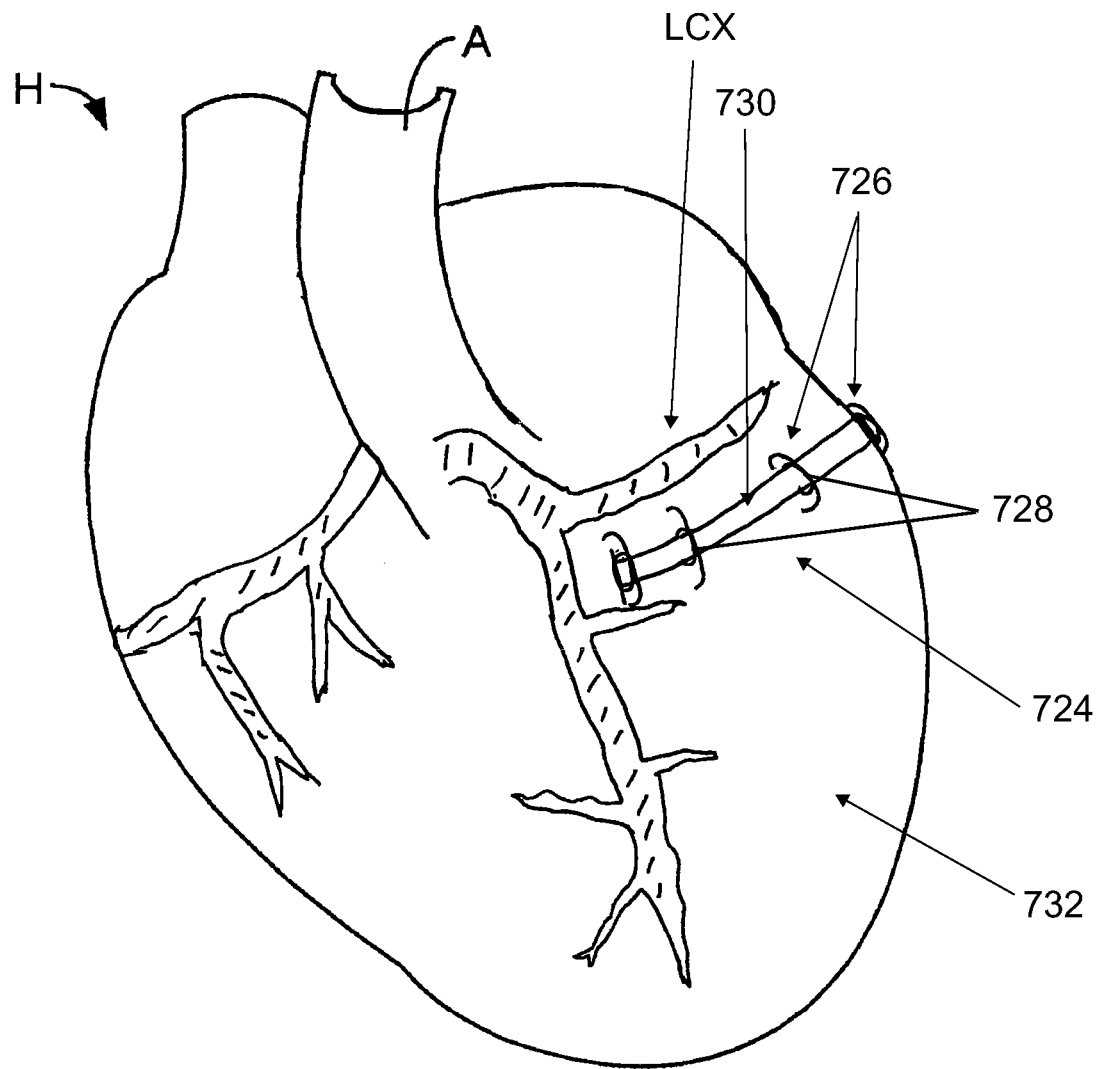

The cinching implants applied to the epicardial surface may have a similar size tissue anchor and tether as the various transvascular embodiments described herein, but in other embodiments, one or more implants may have a longer tether and a greater number of anchors to compensate for the greater diameter of the epicardial surface. In some embodiments, the implants 724 may have anchors 726 with wider eyelets 728 that are configured for slidable coupling to a band-like tether 730, as depicted in FIG. 21B, which may permit the use of fewer tissue anchors 726 and allows the band-type tether 730 to contact and restrain portions of the epicardium 732.

Figure 19A:
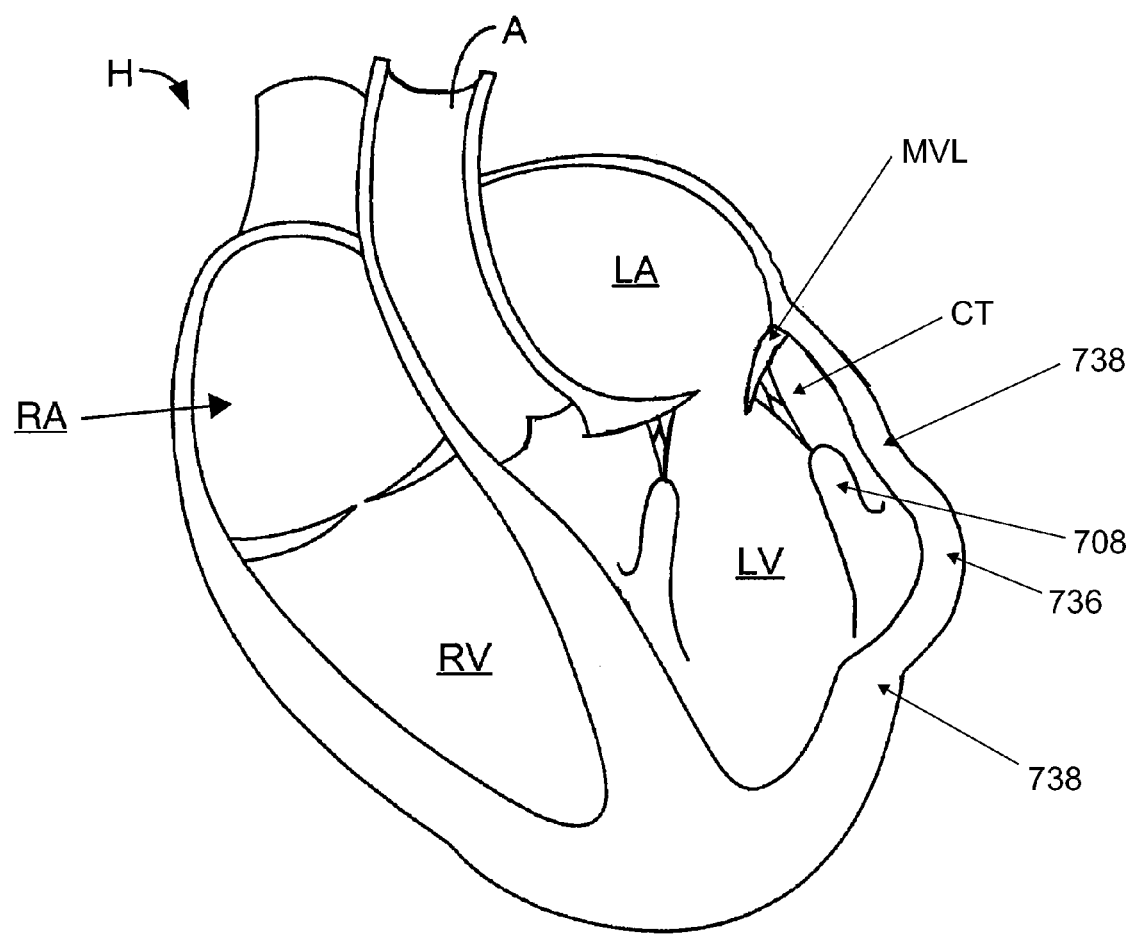
FIG. 19A is a schematic representation of a left ventricle with a dyskinetic wall segment.
Figure 19B:
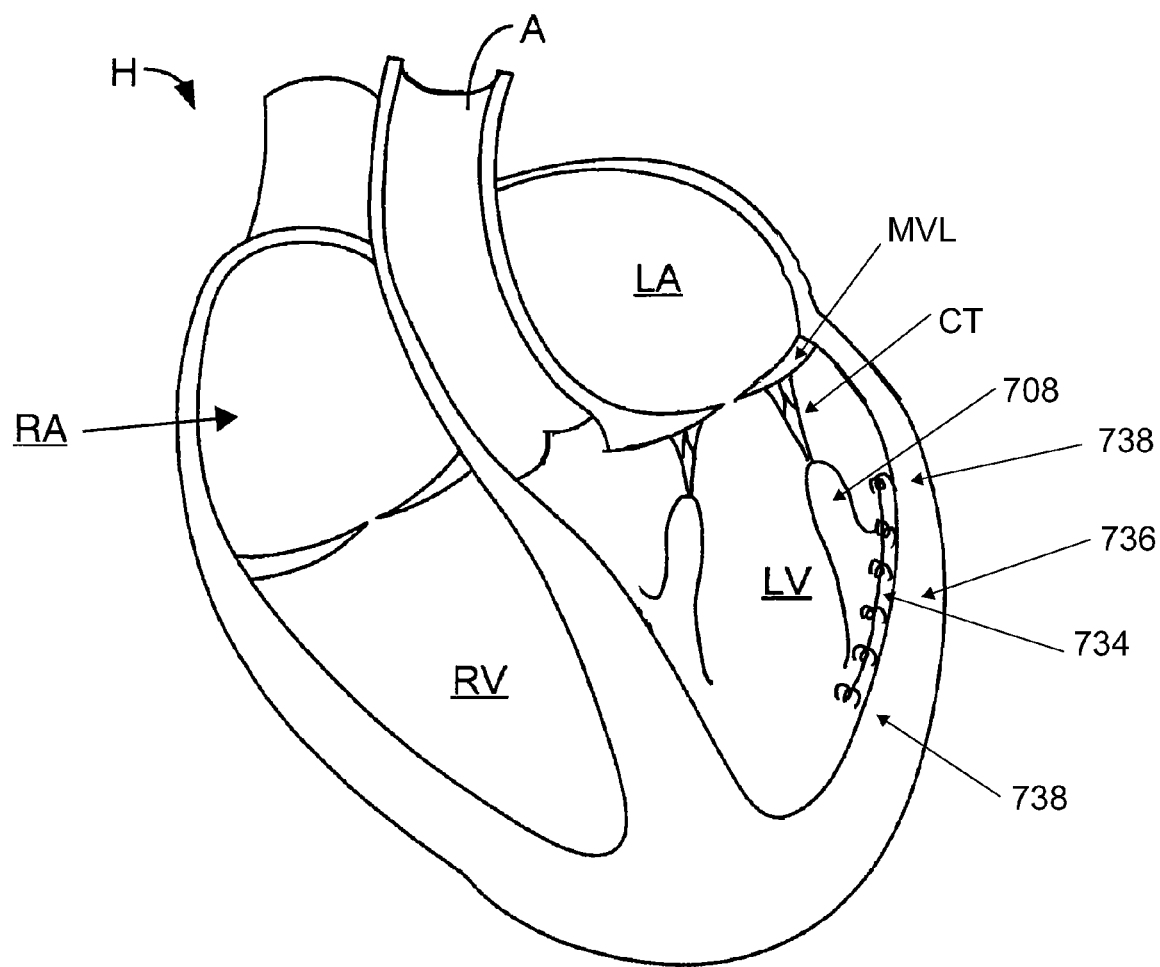
FIG. 19B is a schematic representation of the left ventricle of FIG. 19A following myocardial splinting with a ventricular remodeling implant.

In addition to the use of the cinching implants to restrain ventricular dilation and improve a patient's hemodynamic profile, the cinching implants may also be used to splint dyskinetic wall segments to the intact myocardium. In some instances, splinting of dyskinetic wall segments may reduce paradoxical wall motion during systole. The splinting of dyskinetic wall segments may also improve forward flow through the ventricle and increase the ejection fraction of the left ventricle, and/or valve function when one or more papillary muscles are adjacent to a dyskinetic wall segment. Referring to FIG. 19A, for example, the papillary muscle 708 of the postero-lateral mitral valve leaflet MVL may be proximate to a dyskinetic lateral wall segment 736 that causes leaflet insufficiency during ventricular systole. By positioning a cinching implant 734 across portions of the dyskinetic wall segment 736 and the surrounding intact myocardium 738, the splinted dyskinetic wall segment 736 may resist outward bulging forces during ventricular systole and increase net forward blood flow. The cinching implants 734 used for splinting wall segments may rely on the tension of the tether for splinting effect, but in some embodiments of the invention, a rigid or semi-rigid tether or backbone may be used. Also, in the particular embodiment depicted in FIGS. 19A and 19B, the cinching implant is secured to the myocardium in a longitudinal orientation, but one of skill in the art can image the heart chamber and wall segments to determine the desired implant orientation.

Figure 22A:
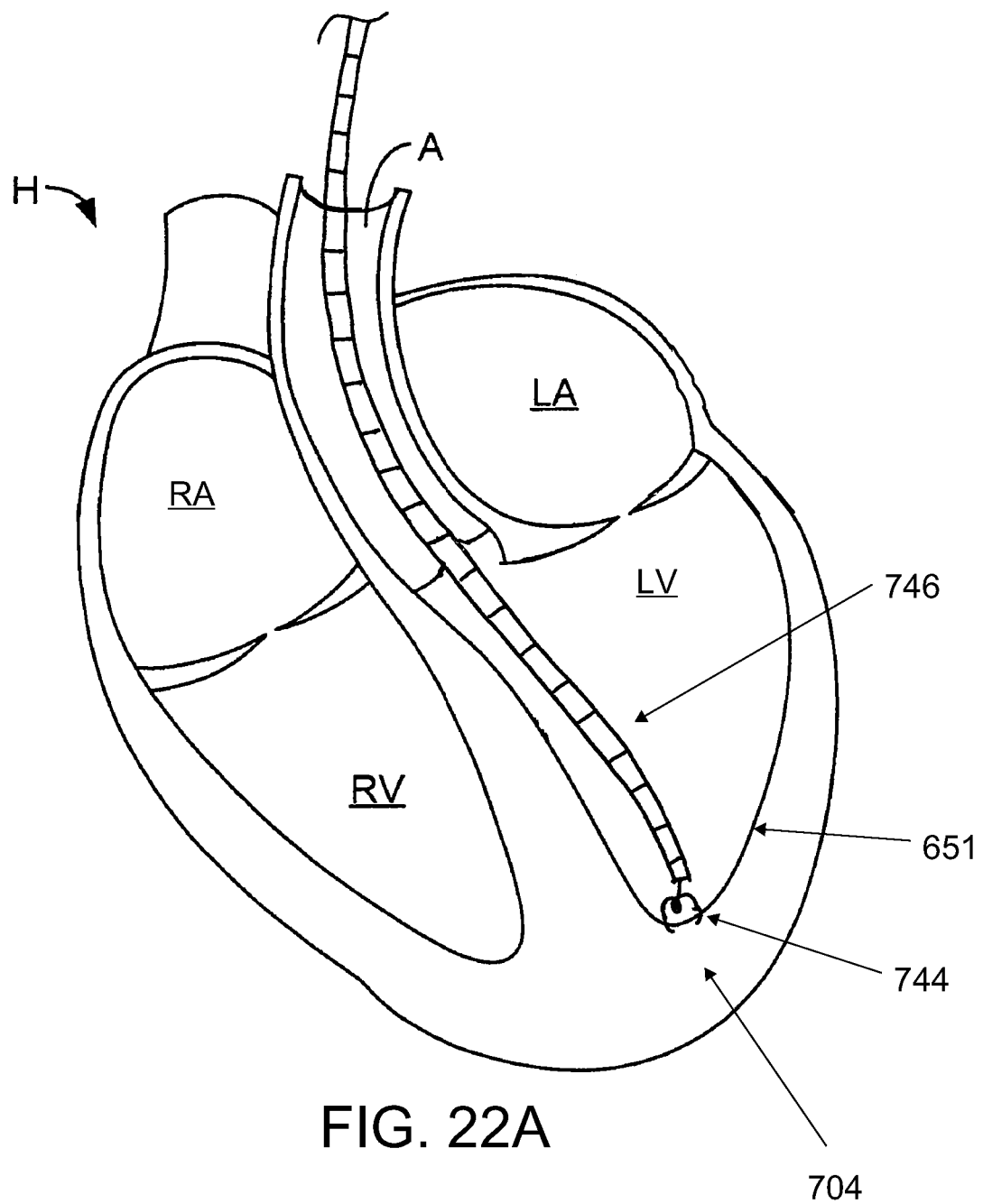
FIGS. 22A through 22C are schematic representations of an implantation of another embodiment of a ventricular reshaping implant.
Figure 22B:
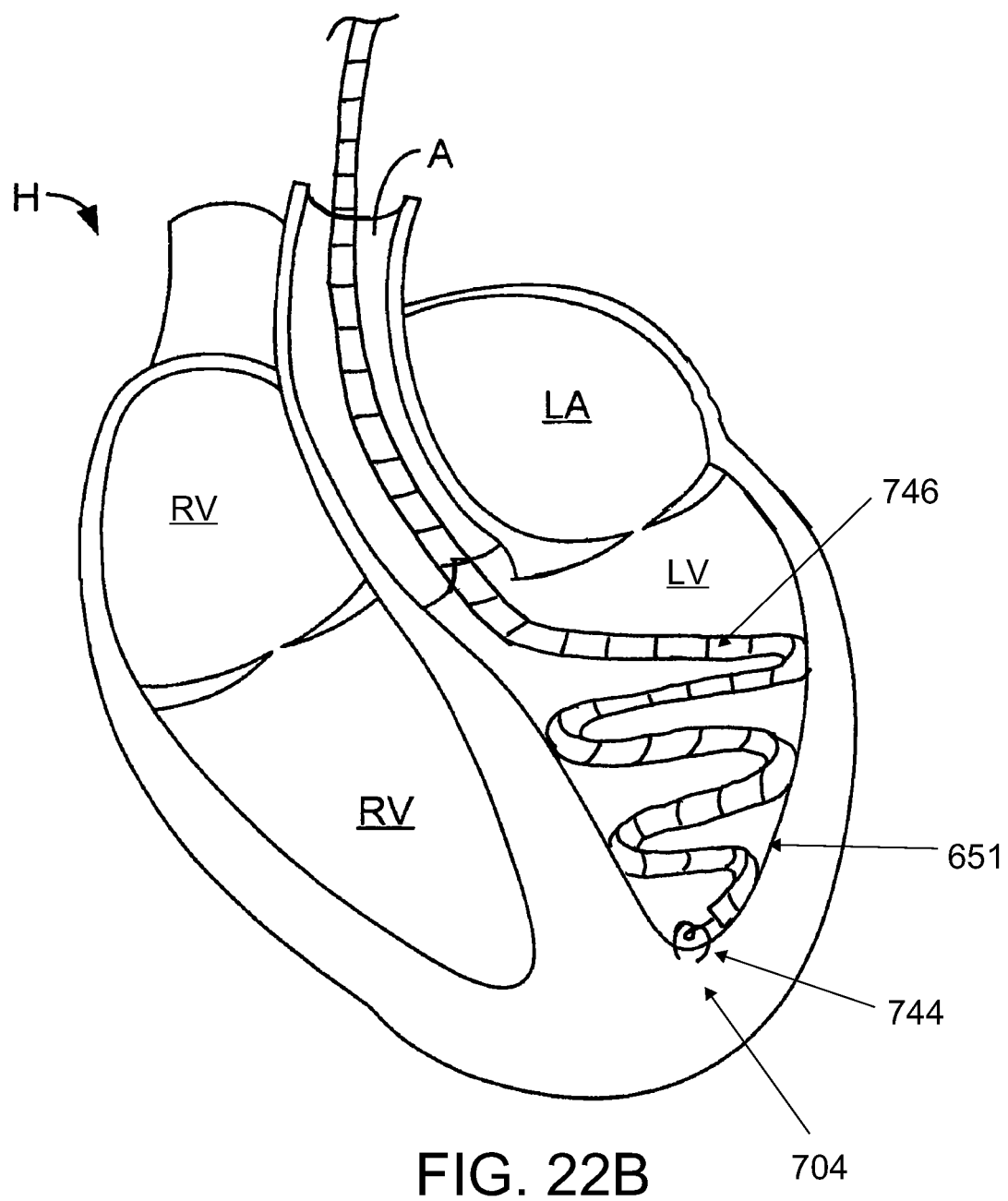
Figure 22C:
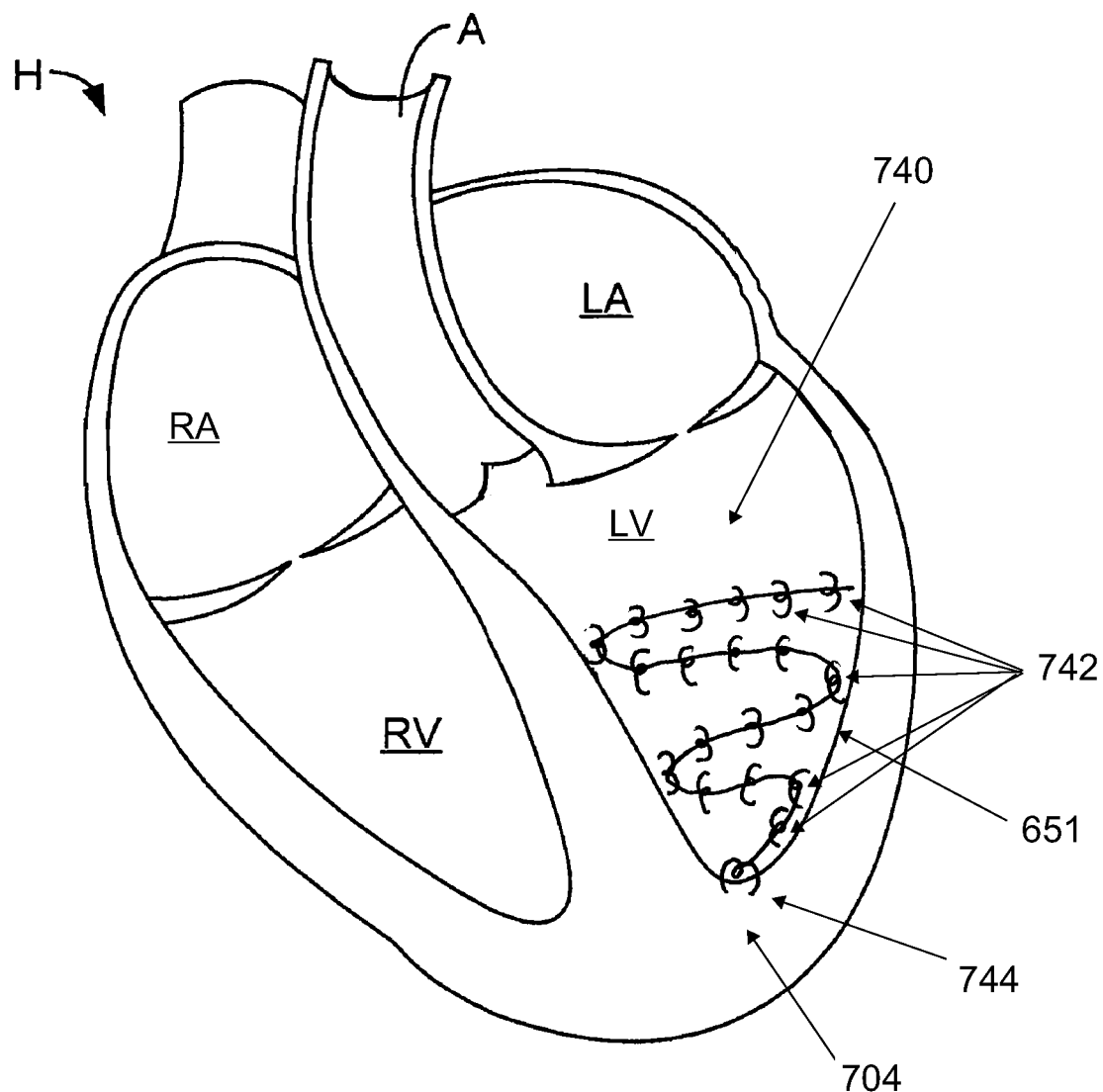

In the embodiments of the cinching implant described above, the implants are configured for generally planar implantation along an arcuate target tissue such as the ventricular wall or subannular groove region. In other embodiments of the invention, the cinching implants may have more complex configurations. FIGS. 22A to 22C, for example, depict the implantation of a helical ventriculoplasty implant 740. The longitudinal length of the helical implant 740 may permit redistribution of the restraining force across a greater number of tissue anchors 742. In some embodiments, the helical anchor 740 may have a length of about 5 cm or more, preferably about 7 cm or more, and most preferably about 9 cm or more. The helical implant 740 may also be designed with a right-handed or left-handed twist configuration, which may complement the theoretical twisting orientation of the myocardial fibers comprising the left ventricle LV.

To implant a ventricular device in a beating heart contracting walls, in some embodiments one end of the implant may first attached to a less mobile portion of the ventricle chamber. In FIG. 22A, the distal end 744 of the implant 740 is first secured to the apical region 704 of the left ventricle LV. Once the distal end 744 of the implant 740 is stabilized, the delivery catheter 746 can be stabilized using the secured distal end 744 and provides sufficient stability to the delivery catheter 746 to assume the desired geometric configuration and orientation. This can occur with a delivery catheter 746 that is made from a shape memory material with an helical geometry that can be reversibly straightened with a movable stiffening wire or element (not shown) within the delivery catheter 746. When the stiffening element is removed and the delivery catheter 746 assumes the helical configuration as shown in FIG. 22B, surface contact between the delivery catheter 746 and the heart wall 651 can be maintained with distally directed force on the delivery catheter 746. Manipulation of the distally directed force can also be used to control the longitudinal length of the heart chamber over which the helical implant 740 is positioned. FIG. 22C depicts the implant 740 after withdrawal of the delivery catheter 746.

In some alternate embodiments, the delivery catheter may be pre-positioned along one or more portions of the subannular groove region or the subvalvular space before the distal tissue anchor is secured to the apex. In still other alternative embodiments, a detachable tissue anchor or engaging structure may be provided about the distal end of the guide wire, guide catheter or delivery catheter to temporarily stabilize delivery catheter for implantation of the cinching implant. After the implant is secured to the myocardium, the detachable tissue anchor or engaging structure may be disengaged from the myocardium and withdrawn from the patient with the other components of the delivery system.

Figure 23A:
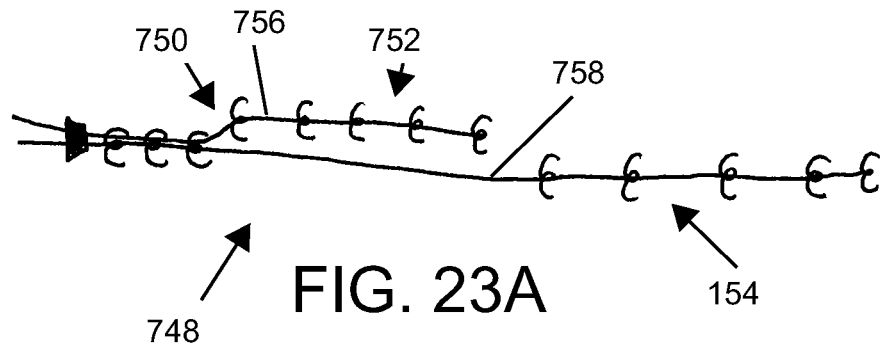
FIGS. 23A and 23B illustrate another embodiment of a ventricular reshaping implant.
Figure 23B:
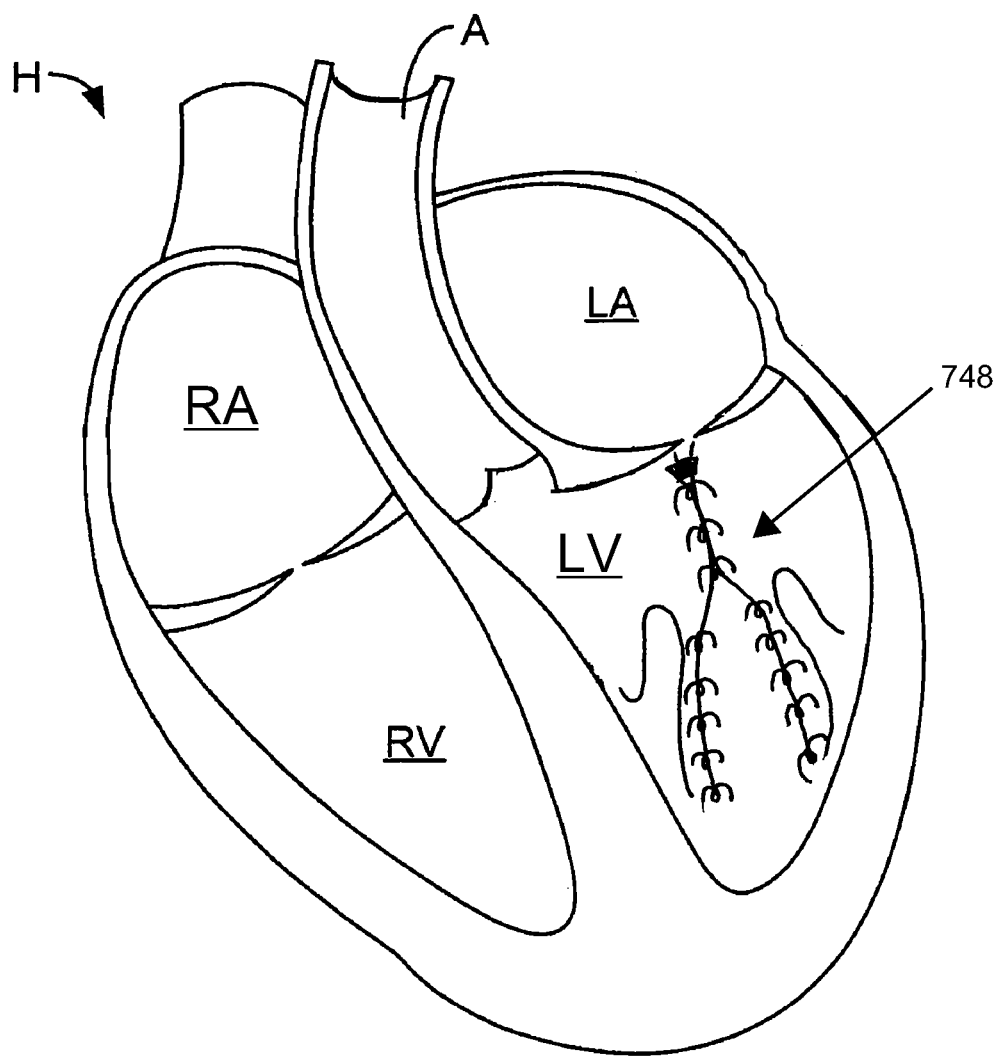

Referring now to FIGS. 23A and 23B, although the embodiments described herein may utilize a cinching implant with a linear or serial configuration, other embodiments may utilize a branched cinching implant 748 having one or more branch sections 750 where two or more arms 752, 754 of the implant 748 are joined. The branched implant 748 may comprise a single tether or multiple tethers 756, 758. Multiple tethers 756, 758 may permit the individual arms 752, 754 of the implant 748 to be cinched to different degrees. One example of a branched implant 748 implanted in a ventricle is shown in FIG. 23B. This particular implantation location may permit the reconfiguration of each papillary muscle to occur with different amount of tension. Alternatively, of course, two or more serially-configured cinching implants may also be used.

Figure 23C:
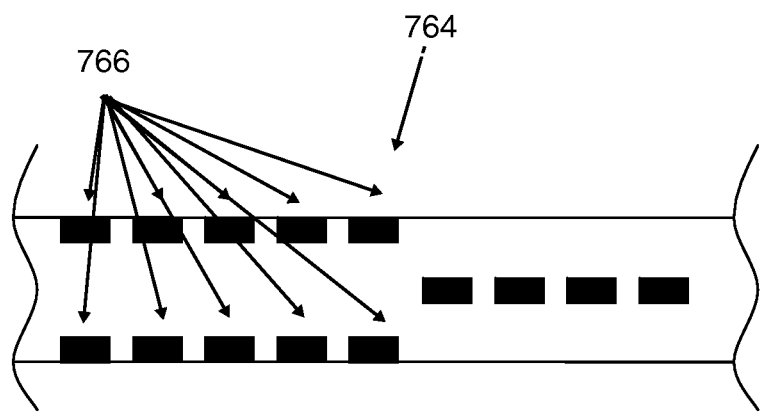
FIGS. 23C and 23D depict embodiments of delivery catheters.
Figure 23D:
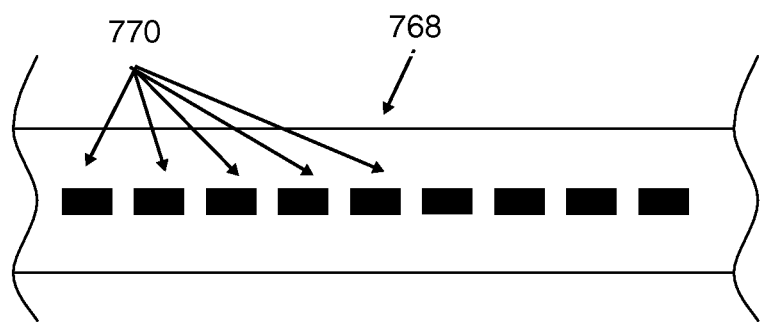

With respect to the delivery of a branched cinching implant, the delivery catheter 764 may be configured with separate openings for each tissue anchor of the implant, as shown in FIG. 23C, wherein the openings 766 for anchors on different arms of the implant are circumferentially separated on the delivery catheter. In some embodiments, the circumferentially separated openings may reduce the risk that a branch tether may get tangled during delivery. In other embodiments, however, all the tissue anchors are delivered along a series of longitudinally spaced openings 770 on the delivery catheter 768, as in FIG. 23D, or through a single opening on the delivery catheter. Referring to FIG. 23A, the implant 748, when loaded into the delivery catheter, may have one or more tether sections 768 without any anchors and may require a substantial amount of cinching to take of the additional slack on the tether.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method for reshaping a heart, comprising:
    positioning a first therapy implant adjacent a first cardiac tissue using a first delivery tool, wherein the first cardiac tissue is non-leaflet tissue at a subvalvular space of a ventricle and the first therapy implant comprises a first plurality of tissue anchors slidably coupled to a first tether;
    reconfiguring the first cardiac tissue using the first therapy implant;
    reconfiguring a second cardiac tissue at a different non-annulus location from the first cardiac tissue using a second therapy implant separate from the first therapy implant that is delivered by a second delivery tool; and
    withdrawing the first and second delivery tools and leaving the first and second therapy implants within the heart.

2. The method of claim 1, wherein reconfiguring the first cardiac tissue occurs before reconfiguring the second cardiac tissue.

3. The method of claim 1,
    wherein the second cardiac tissue is inferior to a third order chordae tendineae.

4. The method of claim 1, wherein the second cardiac tissue is superior to a papillary muscle.

5. The method of claim 1, wherein the second cardiac tissue is inferior to a papillary muscle.

6. The method of claim 1, wherein the second therapy implant is oriented generally perpendicular to a longitudinal axis of the ventricle.

7. The method of claim 1, further comprising passing a guide catheter in a retrograde direction through an aorta.

8. The method of claim 7, wherein positioning the first therapy implant adjacent the first cardiac tissue comprises passing a first delivery catheter through the guide catheter and toward the first cardiac tissue.

9. The method of claim 8, further comprising withdrawing the first delivery catheter from the guide catheter after reconfiguring the first cardiac tissue using the first therapy implant.

10. The method of claim 7, wherein reconfiguring the second cardiac tissue comprises passing a second delivery catheter through the guide catheter and toward the second cardiac tissue.

11. The method of claim 1, wherein reconfiguring the first cardiac tissue using the first therapy device comprises manipulating a cinching member of the first therapy implant.

12. The method of claim 11, wherein the first therapy implant is wholly contained in one heart chamber.

13. The method of claim 1, wherein the second therapy implant comprises a means for reducing a ventricular dimension.

14. The method of claim 13, wherein the ventricular dimension is a septolateral dimension.

15. The method of claim 1, further comprising implanting a third therapy implant at a location different from the locations of the first and second therapy implants.

16. The method of claim 1, wherein the first and second delivery tools are the same tool.

* * * * *